(12) United States Patent
Denmeade et al.

(10) Patent No.: US 8,772,226 B2
(45) Date of Patent: Jul. 8, 2014

(54) METHODS AND COMPOSITIONS FOR THE DETECTION OF CANCER

(75) Inventors: Samuel Ray Denmeade, Ellicott City, MD (US); John Tod Isaacs, Phoenix, MD (US); Soeren Brogger Christensen, Nivaa (DK)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 13/257,131

(22) PCT Filed: Mar. 17, 2010

(86) PCT No.: PCT/US2010/027657
§ 371 (c)(1),
(2), (4) Date: Nov. 29, 2011

(87) PCT Pub. No.: WO2010/107909
PCT Pub. Date: Sep. 23, 2010

(65) Prior Publication Data
US 2012/0093724 A1    Apr. 19, 2012

Related U.S. Application Data

(60) Provisional application No. 61/160,827, filed on Mar. 17, 2009.

(51) Int. Cl.
*A61K 38/00* (2006.01)
*A61K 49/00* (2006.01)
*A61M 36/14* (2006.01)
*A61K 51/00* (2006.01)

(52) U.S. Cl.
USPC ............ 514/1.3; 549/212; 424/9.1; 424/1.61; 424/1.69

(58) Field of Classification Search
CPC ... A61K 31/365; A61K 31/122; A61K 38/00; A61K 31/05; A61K 31/522; A61K 31/7048; C07C 39/14; C07D 243/38; C07D 295/192; C07D 311/16; C07D 403/06; C07D 403/10; C07D 513/04; C07D 307/93; C07D 313/00; C07D 487/22
See application file for complete search history.

(56) References Cited

U.S. PATENT DOCUMENTS

| | | | |
|---|---|---|---|
| 5,290,937 A * | 3/1994 | Tomasella | 548/547 |
| 6,265,540 B1 | 7/2001 | Isaacs et al. | |
| 6,410,514 B1 | 6/2002 | Isaacs et al. | |
| 6,504,014 B1 | 1/2003 | Isaacs et al. | |
| 6,545,131 B1 | 4/2003 | Isaacs et al. | |
| 7,053,042 B1 | 5/2006 | Denmeade et al. | |
| 7,468,354 B2 | 12/2008 | Isaacs et al. | |
| 7,635,682 B2 | 12/2009 | Denmeade et al. | |
| 2006/0217317 A1 | 9/2006 | Denmeade et al. | |
| 2007/0160536 A1 | 7/2007 | Denmeade et al. | |
| 2008/0247950 A1 | 10/2008 | Denmeade et al. | |
| 2009/0163426 A1 | 6/2009 | Isaacs et al. | |

FOREIGN PATENT DOCUMENTS

WO    WO 2004046169 A2 *    6/2004

OTHER PUBLICATIONS

Christensen, S.B. et al., "Thapsigargin analogues for targeting programmed death of androgen-Independent prostate cancer cells", Bioorganic & Medicinal Chemistry, 7:1273-1280; Jul. 1999.
Denmeade, S.R. et al., "Prostate-specific antigen-activated thapsigargin prodrug as targeted therapy for prostate cancer", J. Natl. Cancer Inst., 95(13); 990-1000; Jul. 2, 2003.
Bowden, E. et al., "A Synthesis of 3-(4-Hydroxycyclohexyl)-propanol-1, a Product of the Hydrogenation of Lignin", JACS, 62:2422-2423 Sep. 1940.
Cook, E.S. et al., "Antistaphylococcal and Antifibrinolytic Activities of Omega-Amino Acids and their L-Histidine Dipeptides", J. Med. Chem., 14:354-357 (1971).
Puech, P. et al., "Imaging of Organ-Confined Prostate Cancer: Functional Ultrasound, MRI and PET/computed tomography", Curr. Opin. Urol. 19(2)168-176 (2009).
Marberger, M. et al., "New Treatments for Localized Prostate Cancer", Urology 72(6 suppl):S36-43 (2008).
Bolenz, C. et al., "Clinical Staging Error in Prostate Cancer: Localization and Relevance of Undetected Tumour Areas" BJU Int. 103; 1184-1189, Dec. 22, 2008 [Epub ahead of print].
Chandran, S.S. et al., "A prostate-specific antigen—activated N-(2-hydroxypropyl) methacrylamide copolymer prodrug as dual-targeted therapy for prostate cancer", Mol. cancer Ther. 6(11): 2928-2937 (2007).
Sohoel, H. et al., "NatuRal products as starting materials for development of second-generation SERCA inhibitors targeted towards prostate cancer cells", Bioorganic & Medicinal Chemistry 14(8) 2810-2815 (2006).
Denmeade, S.R., et al., "Prostate-specific antigen—activated thapsigargin prodrug as targeted therapy for prostate cancer", J. Natl. Cancer Inst., Jul. 2003, vol. 95(13), pp. 990-1000.
Janssen, S. et al., "Pharmacokinetics, biodistribution, and antitumor efficacy of a human glandular kallikrein 2(hK2)—activated thapsigargin prodrug" Prostate, Mar. 2006, vol. 66(4), pp. 358-368.

* cited by examiner

*Primary Examiner* — Hong Sang
(74) *Attorney, Agent, or Firm* — Johns Hopkins Technology Transfer

(57) ABSTRACT

Various embodiments of this invention relate generally to targeted activation and delivery of therapeutic drugs to cells that produce prostate specific antigen (PSA), prostate specific membrane antigen (PSMA) or human glandular kallikrein (hK2). Various further embodiments relate more specifically to PSMA-specific peptide prodrugs that become activated to yield therapeutic drugs. Further aspects of various embodiments of the present invention also relate to methods and compositions for treating or preventing cancers and methods and compositions for detecting and/or imaging cancers.

45 Claims, 21 Drawing Sheets

Compound 15

| Tissue | %ID/g |
|---|---|
| Tumor | 2.68 ± 0.20 |
| Kidney | 0.17 ± 0.014 |
| Skeletal Muscle | 0.13 ± 0.15 |
| Brain | 0.0076 ± 0.008 |
| Plasma | 0.00046 ± 0.0001 |
| Tumor/Kidney | 15.4 |
| Tumor/Skeletal Muscle | 20.5 |
| Tumor/Brain | 354.3 |
| Tumor/Plasma | 5816 |

*Fig. 4B*

STRUCTURES OF THE PSMA PRO-DRUG (JHD-9783, A), AND THE PSA PRO-DRUG (JHD-9784, C) WITH THEIR FREE-DRUG STRUCTURES (B AND D).

DETAILS
- JHD-9783:  PRO-DRUG $C_{68}H_{96}N_6O_{28}$, MW 1445.45, SEQUENCE (PhADT)-gGlu-gGlu-gGlu-Glu-OH

FREE DRUG $C_{48}H_{68}N_2O_{16}$, MW 929.01

- JHD-9784:  PRO-DRUG $C_{84}H_{129}N_{13}O_{25}$, MW 1720.99, SEQUENCE (PhADT)-Leu-Gln-Leu-Lys-Ser-Ser-His-morphelinecarbonyl

FREE-DRUG $C_{50}H_{74}N_2O_{14}$, MW 927.10

*FIG. 7*

PSMA-PRODRUG: JHD-9783

PSMA-PRODRUG: JHD-9784

*: SITE FOR RADIO LABEL

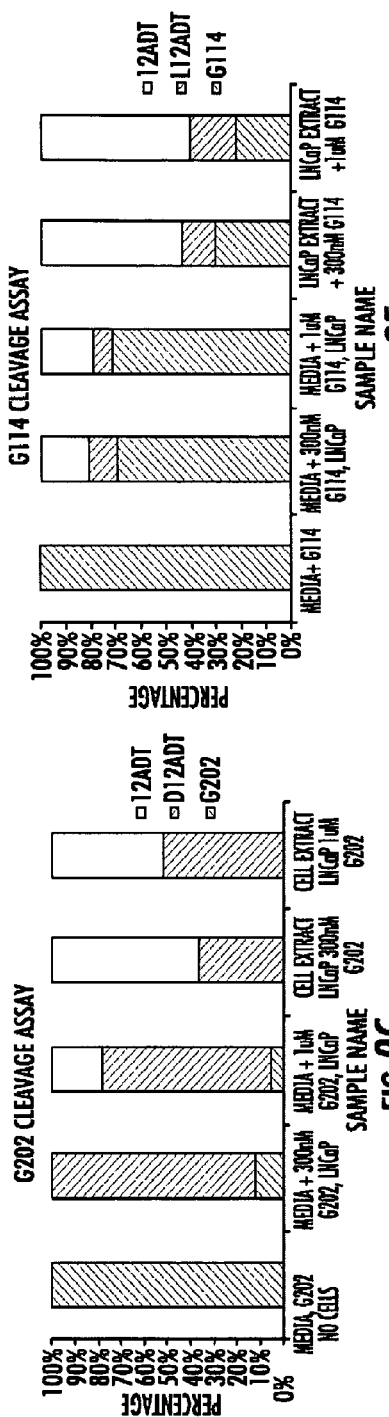
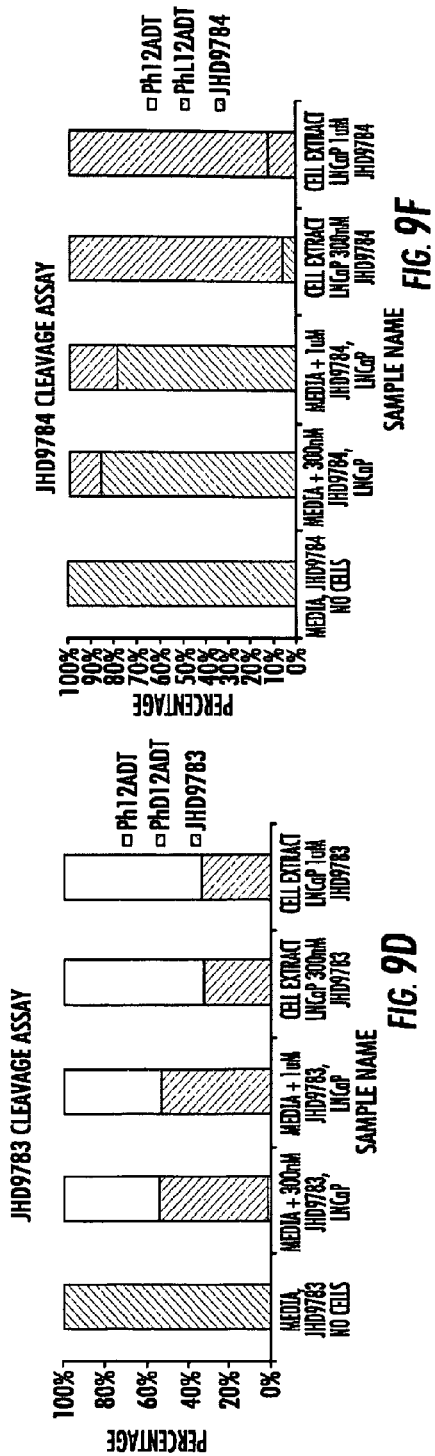
FIG. 9C
FIG. 9D
FIG. 9E
FIG. 9F

|     | P8  | P7  | P6  | P5  | P4  | P3  | P2  | P1  | P-1 | P-2 | P-3 |
| --- | --- | --- | --- | --- | --- | --- | --- | --- | --- | --- | --- |
| Semenogelin I | | | | | | | | | | | |
| 107 ... | His | Lys | Gly | Gly | Lys | Ala | His | 114 ↓ Arg | Gly | Thr | 117 Gln ... |
| 267 ... | Ser | Ser | Ser | Tyr | Glu | Glu | Arg | 274 Arg | Leu | His | 277 Tyr ... |
| 327 ... | Ser | Ser | Ser | Tyr | Glu | Glu | Arg | 334 Arg | Leu | His | 377 Tyr ... |
| 342 ... | Val | Gln | Lys | Asp | Val | Ser | Gln | 349 Arg | Ser | Ile | 352 Tyr ... |
| Semenogelin II | | | | | | | | | | | |
| 94 ... | Asp | Lys | Ser | Lys | Gly | His | Phe | 101 ↓ His | Met | Ile | 104 Val ... |
| 135 ... | Gln | Cys | Ser | Asn | Thr | Glu | Lys | 142 Arg | Leu | Trp | 145 Val ... |
| 215 ... | Leu | His | Pro | Ala | His | Gln | Asp | 222 Arg | Leu | Gln | 225 His ... |
| 262 ... | Lys | Ile | Ser | Tyr | Pro | Ser | Ser | 269 Arg | Thr | Glu | 272 Glu ... |
| 361 ... | Gly | Lys | Ser | Gln | Asn | Gln | Val | 368 Arg | Ile | Pro | 371 Ser ... |
| 447 ... | Ser | Ser | Ser | Tyr | Glu | Glu | Arg | 454 Arg | Leu | Asn | 457 Tyr ... |
| 515 ... | Leu | Ser | His | Glu | Gln | Lys | Gly | 522 Arg | Tyr | Lys | 525 Gln ... |

*Fig. 12*

METHODS AND COMPOSITIONS FOR THE DETECTION OF CANCER

FEDERALLY SPONSORED RESEARCH OR DEVELOPMENT

This invention was made with United States Government support under W81XW0710072 awarded by the Department of Defense. The Government has certain rights in the invention.

CROSS-REFERENCE TO RELATED APPLICATIONS

This application is a 35 U.S.C. 371 U.S. national entry of International Application PCT/US2010/027657 having an international filing date of Mar. 17, 2010, which claims the benefit of U.S. Provisional Application No. 61/160,827, filed Mar. 17, 2009, the content of each of the aforementioned applications is herein incorporated by reference in its entirety.

INCORPORATION-BY-REFERENCE OF MATERIAL SUBMITTED ELECTRONICALLY

The instant application contains a Sequence Listing which has been submitted electronically in ASCII format and is hereby incorporated by reference in its entirety. Said ASCII copy, created on Nov. 13, 2013, is named GENS_0006_SL.txt and is 16,438 bytes in size.

FIELD OF THE INVENTION

Various embodiments of this invention relate generally to targeted activation and delivery of therapeutic drugs to cells that produce prostate specific membrane antigen (PSMA), prostate specific antigen (PSA) or human glandular kallikrein 2 (hK2). Various embodiments relate more specifically to PSA, hK2 or PSMA-specific peptide prodrugs that become activated to yield therapeutic drugs. Further aspects of various embodiments of the present invention also relate to methods and compositions for treating or preventing cancers and methods and compositions for detecting and/or imaging cancers. More particularly, the invention relates to methods and compositions of imaging subjects using PSA, hK2 or PSMA-specific peptide prodrugs.

BACKGROUND

Contrast enhanced trans rectal ultrasound (TRUS), multi-modality 3T magnetic resonance imaging, magnetic resonance spectroscopy and nuclear bone scans are current imaging modalities used in contemporary urological practice for the diagnosis and staging of prostate cancer. Such imaging modalities may be considered prostate imaging modalities, but currently lack the prostate cancer specific imaging modalities. With an increasing number of patients with minimal prostate cancer and opting for either focal treatment or active surveillance, the need for accurate, cancer specific imaging tools for diagnosis, treatment monitoring and follow-up is needed.

Prostate specific antigen (PSA) is a 33,000 kDa single chain glycoprotein first characterized from human prostate tissue. PSA is synthesized and secreted as a unique differentiation product of the prostatic glandular cells, both from normal and cancerous cells. Low levels of PSA are detected in normal and cancerous breast tissue also.

Prostate Specific Antigen (PSA) is a chymotrypsin-like serine protease that is measurable in the blood and is used as a clinical test to detect prostate cancer and follow response to therapy. However, PSA is not active in the blood and is only active within tumor sites and in the normal prostate tissue. The concept of capitalizing upon the prostate specific expression of the protease PSA to target therapeutic agents to prostate cancer sites was first proposed in 1992. Since that time, considerable development, research and systematic effort have been applied to bring that idea to fruition. These efforts have resulted in identification of initial PSA-activated prodrugs which have been described in detail elsewhere (see, for example, U.S. Pat. No. 6,410,514).

Human Glandular Kallikrein 2 (hK2) is the protein product of the human kallikrein gene hKLK2, one of three related kallikrein genes that also include hKLK1 and hKLK3. These three genes are clustered on chromosome 19q13.2 q13.4. The protein product of hKLK3 is prostate-specific antigen (PSA). While PSA is the predominant tissue kallikrein in the prostate, hK2 is also found almost exclusively in the prostate. hK2 is a glycoprotein containing 237 amino acids and a mass of 28.5 kpa. hK2 and PSA share some properties, such as high amino acid sequence identity, prostate localization, androgen regulation and gene expression, but are quite distinct from one another biochemically.

hK2 and PSA differ most markedly in their enzyme properties. Unlike PSA, a chymotrypsin-like protease, hK2 displays the trypsin-like specificity common to most members of the kallikrein family of proteases. hK2 can cleave semenogelin proteins, with an activity that is comparable to PSA. The level of hK2 in the seminal fluid is only 1% of the level of PSA. hK2 has trypsin-like activity, similar to hK1, although it does not appear to function as a classic kininogenase.

In the normal prostate, the levels of expressed hK2 protein are lower than those of PSA. However, hK2 is more highly expressed by prostate cancer cells than by normal prostate epithelium. Comparison of immunohistochemical staining patterns demonstrated incrementally increased staining in poorly differentiated prostate cancers. The intensity of staining has been found to increase with increasing Gleason score, in contrast to PSA, which tends to show decreased staining with increasing Gleason grade, suggesting that hK2 might potentially be a better tumor marker for prostate cancer than PSA.

Recently, three independent groups reported that recombinant hK2 could convert inactive pro-PSA in to the mature PSA protease by release of the propeptide in vitro, thus establishing a possible physiologic connection between hK2 and PSA. hK2 is also secreted in an inactive precursor form. Pro-hK2 may have autocatalytic activity, but the mechanism of activation in vivo is unknown and may involve several additional enzymes. hK2 has also been shown to activate single chain urokinase-type plasminogen activator, scuPA, to the active two-chain form, uPA, which is highly correlated with prostate cancer metastasis. More recently, hK2 has been shown to inactivate the major tissue inhibitor of uPA, plasminogen activator inhibitor-1 (PAI-1). Thus hK2 may influence the progression of prostate cancer by the activation of uPA and by the inactivation of PAI-1.

Prostate Specific Membrane Antigen (PSMA) is a 100 kDa prostate epithelial cell type II transmembrane glycoprotein that was originally isolated from a cDNA library from the androgen responsive LNCaP human prostate cancer cell line (Tombal et al., *Prostate* 43:303-317, 2000). Immunohistochemical studies using monoclonal antibodies have demonstrated that PSMA is expressed by normal prostate epithelium and is even more highly expressed by a large proportion of prostate cancers, including metastatic prostate cancers (Tombal et al., *Prostate*, 43:303-317, 2000; Wright et al., *Urol. Oncol.*, 1:18-28, 1995; Lopes et al., *Cancer Res.*, 50:6423-6429, 1990). Low-level detection of the PSMA protein has also been seen in the duodenal mucosa and in a subset of proximal renal tubules (Silver et al., *Clin. Cancer Res.*, 3:81-85, 1997; Chang et al., *Cancer Res.*, 59:3192-3198, 1999). PSMA enzymatic activity is also present in the brain. In all other human tissues, including normal vascular endothelium, PSMA expression was not detectable. In two separate studies using different monoclonal antibodies, PSMA expression was also undetectable in other non-prostatic primary tumors (Silver et al., *Clin. Cancer Res.*, 3:81-85, 1997; Chang et al., *Cancer Res.*, 59:3192-3198, 1999). In a number of studies, however, PSMA expression, has been detected in the neovasculature of a large number of different tumor types including breast, renal, colon and transitional cell carcinomas (Silver et al., *Clin. Cancer Res.*, 3:81-85, 1997; Chang et al., *Cancer Res.*, 59:3192-3198, 1999). A final interesting aspect of PSMA expression is that the PSMA mRNA is upregulated upon androgen withdrawal (Israeli et al., *Cancer Res.*, 54:1807-1811, 1994; Cunha et al., *Cancer Lett.* 236:229-38, 2006). In contrast, PSA expression is downregulated by androgen deprivation (Chang et al., *Clin. Cancer Res.*, 5:2674-2681, 1999; Godeiro et al., *J. Carcinog.*, 5:21-24, 2006). Therefore, PSMA should be readily targetable in the majority of hormone refractory patients because PSMA levels are expected to remain high following androgen ablation.

Two discrete enzymatic functions for PSMA have been described. Initially, Carter et al., *Proc. Natl. Acad. Sci., USA*, 93:749-753 (1996), demonstrated that PSMA possesses the hydrolytic properties of an N-acetylated α-linked acidic dipeptidase (NAALADase). NAALADase is a membrane hydrolase activity that is able to hydrolyze the neuropeptide N-acetyl-1-aspartyl-1-glutamate (NAAG) to yield the neurotransmitter glutamate and N-acetyl-aspartate (Robinson et al., *J. Biol. Chem.*, 262:14498-14506, 1987; Pinto et al., *Clin. Cancer Res.*, 2:1445-1451, 1996). In addition to the NAALADase activity, PSMA also functions as a pteroyl poly-γ-glutamyl carboxypeptidase (folate hydrolase) (Luthi-Carter et al., *Brain Res.*, 795:341-348, 1998.). PSMA exhibits exopeptidase activity and has been classified as a glutamate carboxypeptidase II (Heston et al., *Urology* 49 (Suppl 3A): 104-112, 1997). It is able to progressively hydrolyze γ-glutamyl linkages of both poly-γ-glutamated folates and methotrexate analogs with varying length glutamate chains (Luthi-Carter et al., *Brain Res.*, 795:341-348, 1998, Mhaka et al., *Cancer Biol. Ther.*, 3:551-8, 2004).

The observation that the PSMA protein continually internalizes, even in the absence of bound antibody, indicates that labeled small molecule inhibitors of PSMA's activity may be used to image prostate cancer. Recently it was demonstrated that both $^{11}C$ and $^{125}I$ radiolabeled urea derivatives with high affinity for PSMA can detect PSMA producing xenografts in nude mice with tumor/muscle ratios of 10.8 and 4.7 respectively at 30 minutes post injection (Singh et al., *J. Med. Chem.*, 48:3005-14, 2005). These agents were also readily taken up by the mouse kidney, which is known to produce the highest levels of PSMA in the mouse. The kidney uptake appeared to be due to inhibitor binding to PSMA as this binding could be blocked by coadministration of high dose of a second, unlabeled, potent PSMA inhibitor (i.e., PMPA) (Singh et al., *J. Med. Chem.*, 48:3005-14, 2005).

These inhibitory compounds, like antibodies, bind to PSMA with 1:1 stoichiometry. As an alternative approach to targeting, the unique enzymatic activity of PSMA can be exploited for signal amplification through the delivery of imaging and/or cytotoxic agents (e.g., prodrugs) that require PSMA for activation selectively within tumor sites.

Thapsigargin (TG) is a sesquiterpene-γ-lactone available by extraction from the seeds and roots of the umbelliferous plant *Thapsia garganica* L. Thapsigargin selectively inhibits the sarcoplasmic reticulum (SR) and endoplasmic reticulum (ER) $Ca^{2+}$-ATPase (SERCA) pump, found in skeletal, cardiac, muscle and brain microsomes. The apparent dissociation constant is 2.2 pM or less.

TG operates by what is believed to be a unique method of killing cells. TG induced inhibition of the SERCA pump leads to depletion of the ER $Ca^{2+}$ pool. This depletion apparently results in the generation of a signal, possibly from an ER-derived diffusible messenger, so that the plasma membrane is more permeable to extracellular divalent cations. The resulting influx of these cations is responsible for the death of cells.

SUMMARY

The presently disclosed subject matter provides a combined approach to imaging and targeted treatment of prostate cancer using a single small molecule species. A highly abundant, highly potent natural product TG with a novel mechanism of cytotoxicity is used as the single molecular species. Further, the presently disclosed subject matter provides selective targeting of PSA, hK2 or PSMA and makes use of the proteolytic activity of a protease to amplify an imaging signal.

Particular embodiments of the invention comprise a composition. The composition may be a combination of small molecule imaging agent and cytotoxin. In certain embodiments the composition may be a prodrug. In embodiments of the invention wherein the composition is a prodrug, it is envisioned that the composition may comprise TG or a TG analog, a phenolic linker and a peptide which is cleavable by a PSA, an hK2 or a PSMA protein or derivative thereof.

In such embodiments where a TG analog is contemplated, it may be any TG analog. Specific TG analogs of interest in the present invention include 8-O-(12[L-leucinoylamino]dodecanoyl)-8-O-debutanoylthapsigargin (L12ADT).

The phenolic linker of the present invention may be radiolabeled. In certain embodiments, the radiolabel is $^{125}I$, $^{124}I$ or $^{131}I$. Further, in aspects including treating a subject having or suspected of having cancer, the short range of alpha or beta irradiation makes labeling with alpha or beta emitters advantageous to gamma emitters, such as the iodine radiolabels. Tritium ($^{3}H$) is a representative beta emitter suitable for use with the presently disclosed methods and compositions.

The peptide of the present invention may be any peptide cleavable by a PSMA protein or derivative thereof. In particular embodiments, the peptide may comprise the sequence Asp-Glu*Glu*Glu*Glu (SEQ ID NO:57). In other embodiments, the peptide may comprise the sequence Asp-Glu.

Alternatively, the peptide of the present invention may be any peptide cleavable by a PSA protein or a derivative thereof. In particular embodiments the peptide may be Ser-Lys-Leu-Gln-Leu (SEQ ID NO:42), Ile-Ser-Tyr-Gln-Leu (SEQ ID NO:43), Lys-Ser-Lys-Gln-Leu (SEQ ID NO:44), Ser-Ser-Lys-Leu-Gln-Leu (SEQ ID NO:45), Lys-Ile-Ser-Tyr-Gln-Leu (SEQ ID NO:46), Thr-Lys-Ser-Lys-Gln-Leu (SEQ ID NO:47), His-Ser-Ser-Lys-Leu-Gln-Leu (SEQ ID NO:48), Asn-Lys-Ile-Ser-Tyr-Gln-Leu (SEQ ID NO:49), Ala-Thr-Lys-Ser-Lys-Gln-Leu (SEQ ID NO:50), Glu-His-Ser-Ser-Lys-Leu-Gln-Leu (SEQ ID NO:51), Gln-Asn-Lys-Ile-Ser-Tyr-Gln-Leu (SEQ ID NO:52), Glu-Asn-Lys-Ile-Ser-Tyr- Gln-Leu (SEQ ID NO:53), Ala-Thr-Lys-Ser-Lys-Gln-His-Leu (SEQ ID NO: 55), or His-Ser-Ser-Lys-Leu-Gln-Leu (SEQ ID NO:56).

Alternatively, the peptide of the present invention may be any peptide cleavable by a hK2 protein or a derivative thereof. In particular embodiments the peptide may be Lys-Arg-Arg (SEQ ID NO:1), Ser-Arg-Arg (SEQ ID NO:2), Ala-Arg-Arg (SEQ ID NO:3), His-Arg-Arg (SEQ ID NO:4), Gln-Arg-Arg (SEQ ID NO:5), Ala-Phe-Arg (SEQ ID NO:6), Ala-Gln-Arg (SEQ ID NO:7), Ala-Lys-Arg (SEQ ID NO:8), Ala-Arg-Lys (SEQ ID NO:9), Ala-His-Arg (SEQ ID NO:10), Gln-Lys-Arg-Arg (SEQ ID NO:11), Lys-Ser-Arg-Arg (SEQ ID NO:12), Ala-Lys-Arg-Arg (SEQ ID NO:13), Lys-Lys-Arg-Arg (SEQ ID NO:14), His-Lys-Arg-Arg (SEQ ID NO:15), Lys-Ala-Phe-Arg] [(SEQ ID NO:16), Lys-Ala-Gln-Arg (SEQ ID NO:17), Lys-Ala-Lys-Arg (SEQ ID NO:18), Lys-Ala-Arg-Lys (SEQ ID NO:19), Lys-Ala-His-Arg (SEQ ID NO:20), Lys-Arg-Arg-Leu (SEQ ID NO:21), Ser-Arg-Arg-Leu (SEQ ID NO:22), Ala-Arg-Arg-Leu (SEQ ID NO:23), Ala-Arg-Arg-Ser (SEQ ID NO:24), His-Arg-Arg-Ala (SEQ ID NO:25), Gln-Arg-Arg-Leu (SEQ ID NO:26), Ala-Phe-Arg-Leu (SEQ ID NO:27), Ala-Gln-Arg-Leu (SEQ ID NO:28), Ala-Lys-Arg-Leu (SEQ ID NO:29), Ala-Arg-Lys-Leu (SEQ ID NO:30), Ala-His-Arg-Leu (SEQ ID NO:31), His-Ala-Gln-Lys-Arg-Arg-Leu (SEQ ID NO:32), Gly-Gly-Lys-Ser-Arg-Arg-Leu (SEQ ID NO:33), His-Glu-Gln-Lys-Arg-Arg-Leu (SEQ ID NO:34), His-Glu-Ala-Lys-Arg-Arg-Leu (SEQ ID NO:35), Gly-Gly-Gln-Lys-Arg-Arg-Leu (SEQ ID NO:36), His-Glu-Gln-Lys-Arg-Arg-Ala (SEQ ID NO:37), Gly-Gly-Ala-Lys-Arg-Arg-Leu (SEQ ID NO:38), His-Glu-Gln-Lys-Arg-Arg-Ser (SEQ ID NO:39), Gly-Gly-Lys-Lys-Arg-Arg-Leu (SEQ ID NO:40), Gly-Gly-His-Lys-Arg-Arg-Leu (SEQ ID NO:41) or Gly-Gly-Lys-Ala-Arg-Arg-Leu (SEQ ID NO:54).

In some embodiments of the presently disclosed compositions, the peptide further comprises a capping group attached to the N-terminus of the peptide, wherein the capping group inhibits endopeptidase activity. In particular embodiments, the capping group is selected from the group consisting of acetyl, morpholinocarbonyl, benzyloxycarbonyl, glutaryl, and succinyl substituents.

In the embodiments of the present invention, the combination of small molecule imaging agent and cytotoxin may be used to treat or image subjects having or suspected of having prostate cancer. In the embodiments of the invention, methods of imaging a subject, such as a subject with prostate cancer or suspected of having prostate cancer, include the use of single photon emission computed tomography (SPECT) imaging. Still in other embodiments, the imaging is positron emission tomography (PET).

In such embodiments involving imaging, methods may include providing to a subject a prodrug comprising TG or a TG analog, a phenolic linker with a radiolabel and a peptide cleavable by a PSA, an hK2 or PSMA cleavable peptide. Still further, the radiolabel may be $^{125}$I or $^{124}$I.

In particular embodiments involving treatment of subjects, the method of treatment may also comprise providing to a subject a prodrug comprising TG or a TG analog, a phenolic linker with a radiolabel and a peptide cleavable by a PSA, an hK2 or a PSMA protein or derivative thereof. In these embodiments, the method of treatment may be combination drug/radiation therapy and the radiolabel may be $^{131}$I.

Particular embodiments of the invention comprise a composition. The composition may be a prodrug.

Certain aspects of the presently disclosed subject matter having been stated hereinabove, which are addressed in whole or in part by the presently disclosed subject matter, other aspects will become evident as the description proceeds when taken in connection with the accompanying Examples and Drawings as best described herein below.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the specific embodiments presented herein.

FIGS. 4A and 4B are (A) selective accumulation of 12ADT-Asp and 12ADT-Asp-Glu in tumor tissue compared to indicated normal tissue five days after single intravenous dose of 2 μmole (120 mg/kg) (FIG. 4A discloses "Asp-Glu*Glu*Glu*Glu" as SEQ ID NO: 57); and (B) biodistribution of TG species (sum of 12ADT-Asp, 12ADT-Asp-Glu and 12ADT-Asp-Glu*Glu*Glu*Glu (SEQ ID NO: 57)) in CWR22H tumor bearing mice. Data presented as % Initial dose (ID)/gram and tumor/tissue ratios (n=4 mice).

FIG. 7. Imaging pro-drugs: JHD-9783 (PSMA) (SEQ ID NO: 63) and JHD-9784 (PSA) (SEQ ID NO: 64) were designed on the basis of 2 therapeutic pro-drugs: G202 (PSMA) and G114 (PSA). The difference between the 2 groups is the addition of a phenol ring for imaging probe linking ($^{125}$I).

FIG. 9 Cleavage assay for 2 PSMA pro-drugs G202 (C) and JHD9783 (D) and 2 PSA pro-drugs G114 (E) and JHD9784 (F). Metabolites were detected with LC/MS. Results show that LNCaP cells can cleave all compounds. Highest amount of free-drug was found in the cell extract sample, indicating clear uptake of the activated free-drug.

FIG. 12. Peptide cleavage sites for hK2 in semenogelin I (SEQ ID NOS 65-66 and 66-67, respectively, in order of appearance) and II (SEQ ID NOS 68-72, 66 and 73, respectively, in order of appearance).

DETAILED DESCRIPTION

Figure 1:
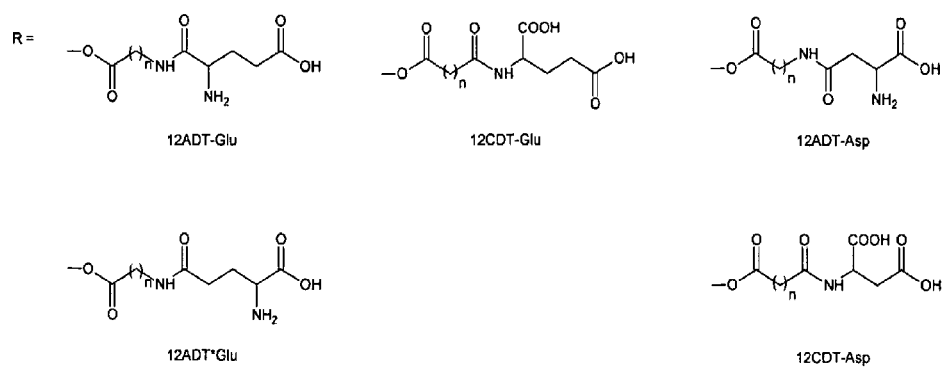
FIG. 1 provides chemical structures of representative aspartate and glutamate containing linkers suitable for use with particular embodiments of the presently disclosed PMSA-activated TG prodrug.

Various embodiments of the present invention are based in part on the discovery of the inventors of methods and compositions related to imaging the prostate and prostate cells of a subject to treat or detect a prostate hyperproliferative disease, such as cancer by developing a prodrug including a peptide sequence coupled to a cytotoxic drug. In certain embodiments of the invention, the prodrug coupled to the cytotoxic drug contains a radiolabel. In certain embodiments, the cytotoxic drug is thapsigargin (TG) or an analog thereof. TG or analogs thereof may be cleaved from the peptide carrier by the targeted protease and release active drug.

In various embodiments of the invention, the inventors have created a novel analog of TG consisting of a linker containing a phenolic ring. In particular embodiments this phenolic ring linker can be radiolabeled, e.g., iodinated, to produce a thapsigargin analog that is itself toxic to cells through inhibition of its target, but can also deliver a radiolabel to the target. In certain embodiments, the radiolabel is an isotope of iodine. In still further embodiments, the iodine can be $^{125}$I, $^{124}$I or $^{131}$I. In certain aspects of this invention, the TG or TG analog can be coupled to peptides that are protease substrates to allow for targeting of the radiolabeled drug to a prostate tissue, such as, for example, a prostate tumor tissue. In aspects of the invention, such targeting may allow for treatment and/or imaging of the tumor sites. The phenolic ring can be labeled with $^{125}$I for SPECT imaging and $^{124}$I for PET imaging and $^{131}$I for combination drug/radiation therapy.

hK2 Specific Peptide

As used herein the term "human glandular kallikrein 2" (hK2) means human glandular kallikrein 2, as well as other proteases that have the same or substantially the same proteolytic cleavage specificity as hK2. In one aspect the invention features a peptide containing an amino acid sequence that includes a cleavage site specific for hk2 or an enzyme having a proteolytic activity of hK2. The peptides of the invention are preferably not more than 20 amino acids in length, more preferably to more than ten amino acids in length. The preferred amino acid sequences of the invention are linear. In an embodiment of the invention the amino acid sequence may be cyclical such that the cyclical form of the sequence is an inactive drug that can become an activated drug upon cleavage by hK2 and linearization.

The cleavage site recognized by hK2 is flanked by at least an amino acid sequence, $X_4X_3X_2X_1$. This oligopeptide contains the amino acid arginine, histidine or lysine at position $X_1$. $X_2$ can be arginine, phenylalanine, lysine, or histidine. $X_3$ can be lysine, serine, alanine, histidine or glutamine. $X_4$ can be from 0 to 20 further amino acids, preferably at least two further amino acids. Some preferred embodiments include a sequence for $X_4$ that is substantially identical to the 20 amino acids in the wild type semenogelin I or semenogelin II sequence that are the from fourth to twenty fourth amino acids to the N-terminal side of recognized semenogelin cleavage sites. The amino acid sequence can further comprise $X_{-1}$, which is linked to the carboxy terminus of $X_1$ to create the amino acid sequence $X_4X_3X_2X_1X_{-1}$. $X_{-1}$ is up to a further 10 amino acids, and can include any amino acids. Preferably $X_1$ has leucine, alanine or serine linked to the carboxy terminus of $X_1$. $X_{-1}$ can include L- or D-amino acids.

The hK2 cleavage site is located at the carboxy terminal side of $X_1$.

In some preferred peptides, both X.sub.1 and X.sub.2 are arginine.

Some examples of preferred peptides include (Note that the symbol ][ denotes an hK2 cleavage site):

1. Lys-Arg-Arg][ (SEQ ID NO: 1)

2. Ser-Arg-Arg][ (SEQ ID NO: 2)

3. Ala-Arg-Arg][ (SEQ ID NO: 3)

4. His-Arg-Arg][ (SEQ ID NO: 4)

5. Gln-Arg-Arg][ (SEQ ID NO: 5)

6. Ala-Phe-Arg][ (SEQ ID NO: 6)

7. Ala-Gln-Arg][ (SEQ ID NO: 7)

8. Ala-Lys-Arg][ (SEQ ID NO: 8)

9. Ala-Arg-Lys][ (SEQ ID NO: 9)

10. Ala-His-Arg][ (SEQ ID NO: 10)

Additional preferred peptides of longer sequence length include:

11. Gln-Lys-Arg-Arg][ (SEQ ID NO: 11)

12. Lys-Ser-Arg-Arg][ (SEQ ID NO: 12)

13. Ala-Lys-Arg-Arg][ (SEQ ID NO: 13)

14. Lys-Lys-Arg-Arg][ (SEQ ID NO: 14)

-continued

15. His-Lys-Arg-Arg][ (SEQ ID NO: 15)

16. Lys-Ala-Phe-Arg][ (SEQ ID NO: 16)

17. Lys-Ala-Gln-Arg][ (SEQ ID NO: 17)

18. Lys-Ala-Lys-Arg][ (SEQ ID NO: 18)

19. Lys-Ala-Arg-Lys][ (SEQ ID NO: 19)

20. Lys-Ala-His-Arg][ SEQ ID NO: 20)

Additional preferred peptides that include an $X_{-1}$ amino acid are:

21. Lys-Arg-Arg][Leu (SEQ ID NO: 21)

22. Ser-Arg-Arg][Leu (SEQ ID NO: 22)

23. Ala-Arg-Arg][Leu (SEQ ID NO: 23)

24. Ala-Arg-Arg][Ser (SEQ ID NO: 24)

25. His-Arg-Arg][Ala (SEQ ID NO: 25)

26. Gln-Arg-Arg][Leu (SEQ ID NO: 26)

27. Ala-Phe-Arg][Leu (SEQ ID NO: 27)

28. Ala-Gln-Arg][Leu (SEQ ID NO: 28)

29. Ala-Lys-Arg][Leu (SEQ ID NO: 29)

30. Ala-Arg-Lys][Leu (SEQ ID NO: 30)

31. Ala-His-Arg][Leu (SEQ ID NO: 31)

Preferred peptides of still longer sequence length having $X_{-1}$ include:

32. His-Ala-Gln-Lys-Arg-Arg][Leu (SEQ ID NO: 32)

33. Gly-Gly-Lys-Ser-Arg-Arg][Leu (SEQ ID NO: 33)

34. His-Glu-Gln-Lys-Arg-Arg][Leu (SEQ ID NO: 34)

35. His-Glu-Ala-Lys-Arg-Arg][Leu (SEQ ID NO: 35)

36. Gly-Gly-Gln-Lys-Arg-Arg][Leu (SEQ ID NO: 36)

37. His-Glu-Gln-Lys-Arg-Arg][Ala (SEQ ID NO: 37)

38. Gly-Gly-Ala-Lys-Arg-Arg][Leu (SEQ ID NO: 38)

39. His-Glu-Gln-Lys-Arg-Arg][Ser (SEQ ID NO: 39)

40. Gly-Gly-Lys-Lys-Arg-Arg][Leu (SEQ ID NO: 40)

41. Gly-Gly-His-Lys-Arg-Arg][Leu (SEQ ID NO: 41)

42. Gly-Gly-Lys-Ala-Arg-Arg-Leu. (SEQ ID NO: 54)

Other embodiments of peptide sequences which are useful for cleavage by hK2 and proteases with the hydrolytic activity of hK2 are disclosed in the Examples section. Further examples of the peptides of the invention are constructed as analogs of, derivatives of and conservative variations on the amino acids sequences disclosed herein. Thus, the broader group of peptides having hydrophilic and hydrophobic substitutions, and conservative variations are encompassed by the invention. Those of skill in the art can make similar substitutions to achieve peptides with greater activity and or specificity toward hK2. For example, the invention includes peptide sequences described above, as well as analogs or derivatives thereof, as long as the bioactivity of the peptide remains. Minor modifications of the primary amino acid sequence of the peptides of the invention may result in peptides that have substantially equivalent activity as compared to the specific peptides described herein. Such modifications may be deliberate, as by site directed mutagenesis or chemical synthesis, or may be spontaneous. All of the peptides produced by these modifications are included herein, as long as the biological activity of the original peptide remains, i.e., susceptibility to cleavage by hK2. Additional information regarding hK2 cleavable peptides may be found in U.S. Pat. No. 7,053,042 which is hereby incorporated by reference in its entirety.

Further, deletion of one or more amino acids can also result in a modification of the structure of the resultant molecule without significantly altering its biological activity. This can lead to the development of a smaller active molecule without significantly altering its biological activity. This can lead to the development of a smaller active molecule which would also have utility. For example, amino or carboxy-terminal amino acids which may not be required for biological activity of the particular peptide can be removed. Peptides of the invention include any analog, homolog, mutant or isomer or derivative of the peptides disclosed in the present invention, as long as bioactivity described herein remains. All peptides described have sequences comprised of L-amino acids; however, D-forms of the amino acids can be synthetically produced and used in the peptides described herein.

The peptides of the invention include peptides which are conservative variations of those peptides specifically exemplified herein. The term "conservative variation" as used herein denotes the replacement of an amino acid residue by another, biologically similar residue. Examples of conserved variations include the substitution of one hydrophobic residue, such as isoleucine, valine, leucine, alanine, cysteine, glycine, phenylalanine, proline, tryptophan, tyrosine, norleucine or methionine for another or the substitution of one polar residue for another, such as the substitution of arginine for lysine or histidine, glutamic for aspartic acids or glutamine for asparagine, and the like. Neutral hydrophilic amino acids that can be substituted for one another include asparagine, glutamine, serine, and threonine. Such conservative substitutions are within the definitions of the classes of peptides of the invention with respect to X positions which may be any number of amino acids. The peptides that are produced by such conservative variation can be screened for suitability of use in the prodrugs of the invention according to the methods for selecting prodrugs provided herein.

A wide variety of groups can be linked to the carboxy terminus of $X_1$ or $X_{-1}$. Notably, therapeutic drugs can be linked to this position. In this way advantage is taken of the hK2 specificity of the cleavage site, as well as other functional characteristics of the peptides of the invention. Preferably, the therapeutic drugs are linked to the carboxy terminus of $X_1$ either directly or through a linker group. The direct linkage is preferably through an amide bond, in order to utilize the proteolytic activity and specificity of hK2. If the connection between the therapeutic drug and the amino acid sequence is made through a linker, this connection is also preferably made through an amide bond, for the same reason. This linker may be connected to the therapeutic drug through any of the bond types and chemical groups known to those skilled in the art. The linker may consist of the amino acid (s) comprising $X_{-1}$. The linker may remain on the therapeutic drug, or may be removed soon thereafter, either by further reactions or in a self-cleaving step. Self-cleaving linkers are those linkers which can intramolecularly cyclize and release the drug or undergo spontaneous $S^N1$ solvolysis and release the drug upon peptide cleavage.

Other materials, such as detectable labels or imaging compounds, can be linked to the peptide. Groups can be linked to the amino terminus of $X_7$, including such moieties as antibodies, and peptide toxins, including the 26 amino acid toxin, melittin and the 35 amino acid toxin cecropin B for example. Both of these peptide toxins have shown toxicity against cancer cell lines. The N-terminal amino acid of the peptide may also be attached to the C-terminal amino acid either via an amide bond formed by the N-terminal amine and the C-terminal carboxyl, or via coupling of side chains on the N-terminal and C-terminal amino acids or via disulfide bond formed when the N-terminal and C-terminal amino acids both consist of the amino acid cysteine. Further, it is envisioned that the peptides described herein can be coupled, via the carboxy terminus of $X_1$ or $X_{-1}$, to a variety of peptide toxins (for example, melittin and cecropin are examples of insect toxins), so that cleavage by hK2 liberates an active toxin. Additionally, the peptide could be coupled to a protein such that the protein is connected at the $X_1$ or $X_{-1}$ amino acid of the peptide. This coupling can be used to create an inactive proenzyme so that cleavage by a tissue-specific protease (such as hK2 or PSA) would cause a conformational change in the protein to activate it. For example, *Pseudomonas* toxin has a leader peptide sequence which must be cleaved to activate the protein. Additionally, the peptide sequence could be used to couple a drug to an antibody. The antibody could be coupled to the N-terminus of the peptide sequence (that is, $X_4$ or higher X amino acids), and the drug coupled to the carboxy terminus (that is $X_1$ or $X_{-1}$). The antibody would bind to a cell surface protein and tissue-specific protease present in the extracellular fluid could cleave the drug from the peptide linker.

The preferred amino acid sequence can be constructed to be highly specific for cleavage by hK2. In addition the peptide sequence can be constructed to be highly selective towards cleavage by hK2 as compared to purified extracellular and intracellular proteases. Highly-specific hK2 sequences can also be constructed that are also stable toward cleavage in human sera.

The peptides of the invention can be synthesized according to any of the recognized procedures in the art, including such commonly used methods as t-boc or fmoc protection of alpha-amino groups. Both methods involve stepwise syntheses whereby a single amino acid is added at each step starting from the C-terminus of the peptide. Peptides of the invention can also be synthesized by well-known solid phase peptide synthesis methods. Peptides can be characterized using standard techniques, such as amino acid analysis, thin layer chromatography, or high performance liquid chromatography, for example.

Method of Screening Tissue and Determining hK2 Activity

In another aspect the invention provides a method of detecting hK2-producing tissue using peptides of the invention, as described above. The method is carried out by contacting a detectably labeled peptide of the invention with target tissue for a period of time sufficient to allow hK2 to cleave the peptide and release the detectable label. The detectable label is then detected. The level of detection is compared to that of a control sample not contacted with the target tissue. Many varieties of detectable labels are available, including optically based labels, such as chromophoric, chemiluminescent, fluoresecent or phosphorescent labels and radioactive labels, such as alpha, beta, or gamma emitting labels. In addition a peptide label consisting of an amino acid sequence comprising $X_{-1}$ can be utilized for detection such that release of the $X_{-1}$ label by hK2 proteolysis can be detected by high pressure liquid chromatography. The peptide sequences of the invention can also be incorporated into the protein sequence of a fluorescent protein such that cleavage of the incorporated hK2 specific sequence by hK2 results in either an increased or decreased fluorescent signal that can be measured using the appropriate fluorometric measuring instrument.

The invention provides a method for detecting a cell proliferative disorder that comprises contacting an hK2-specific peptide with a cell suspected of producing hK2. The hK2 reactive peptide is labeled by a compound so that cleavage by hK2 can be detected. For purposes of the invention, a peptide specific for hK2 may be used to detect the level of enzymatically active hK2 in biological tissues, such as saliva, blood, urine, and tissue culture media. In an embodiment of the method a specific hK2 inhibitor is used to confirm that the activity being measured is solely due to peptide cleavage by hK2 and not secondary to non-specific cleavage by other proteases present in the biological tissue being assayed. Examples of hK2 inhibitors that can be employed in the method include the addition of zinc ions, or the addition of hK2 specific antibodies that bind to the catalytic site of hK2 thereby inhibiting enzymatic activity of hK2.

PSA Specific Peptides

As used herein, the term "prostate specific antigen" (PSA) means prostate specific antigen, as well as all other proteases that have the same or substantially the same proteolytic cleavage specificity as prostate specific antigen. As used herein, "sufficiently toxic" refers to therapeutic drugs which display nonspecific toxicity toward cells with an $LC_{50}$ concentration that is at least 3 times lower than the LC.sub.50 concentration of the prodrugs of the invention, more preferably at least 20 times lower, and therapeutic drugs most preferably have an $LC_{50}$ concentration that is at least 100 times lower than the LC.sub.50 concentration of the prodrugs of the invention. The term "contacting" refers to exposing tissue to the peptides, therapeutic drugs or prodrugs of the invention so that they can effectively inhibit cellular processes, or kill cells. Contacting may be in vitro, for example by adding the peptide, drug, or prodrug to a tissue culture to test for susceptibility of the tissue to the peptide, drug or prodrug. Contacting may be in vivo, for example administering the peptide, drug or prodrug to a subject with a cell proliferative disorder, such as prostate or breast cancer. By "polypeptide" is meant any chain of amino acids, regardless of length or post-translational modification (e.g., glycosylation or phosphorylation). As written herein, amino acid sequences are presented according to the standard convention, namely that the amino terminus of the peptide is on the left, and the carboxy terminus on the right. In one aspect, the invention features a peptide containing an amino acid sequence that includes a cleavage site specific for PSA or an enzyme having a proteolytic activity of PSA. The peptides of the invention are preferably not more than 20 amino acids in length, more preferably not more than 10 amino acids in length. The preferred amino acid sequences of the invention are linear.

The cleavage site recognized by PSA is flanked by at least an amino acid sequence, $X_5X_4X_3X_2X_1$. This peptide contains the amino acid glutamine, asparagine or tyrosine at position $X_1$. $X_2$ can be leucine, tyrosine, or lysine. $X_3$ can be serine or lysine. $X_4$ can be serine, isoleucine, or lysine. $X_5$ can be from 0 to 16 further amino acids. Some preferred embodiments include a sequence for $X_5$ that is substantially identical to the 16 remaining amino acids in the wild type semenogelin I or semenogelin II sequence. The amino acid sequence can further comprise $X_{-1}$ which is linked to the carboxy terminus of $X_1$ to create the amino acid sequence $X_5X_4X_3X_2X_1X_{-1}$. $X_{-1}$ is up to 10 further amino acids. Preferably, $X_{-1}$ has histidine, leucine, threonine or serine linked to the carboxy terminus of $X_1$. The PSA cleavage site is located at the carboxy terminal side of $X_{-1}$, unless $X_{-1}$ has histidine linked to the carboxy terminus of $X_1$, in which case the PSA cleavage site is to the carboxy terminal side of histidine.

Another amino acid sequence is $X_6X_5X_4X_3X_2X_1$ in which $X_5$ is serine or lysine, $X_6$ is from 0 to 15 further amino acids, and the other amino acids are as above. X.sub.-1 can also be present, as noted above. Another amino acid sequence is $X_6X_5X_4X_3X_2X_1$, in which $X_6$ is histidine or asparagine $X_7$ is from 0 to 14 further amino acids, and the other amino acids are as above. $X_{-1}$ can also be present, as noted above.

Some examples of preferred peptides include tetraamino acid sequences, such as Ser-Lys-Leu-Gln-Leu (SEQ ID NO:42), Ile-Ser-Tyr-Gln-Leu (SEQ ID NO:43), Lys-Ser-Lys-Gln-Leu (SEQ ID NO:44), Ser-Ser-Lys-Leu-Gln-Leu (SEQ ID NO:45), Lys-Ile-Ser-Tyr-Gln-Leu (SEQ ID NO:46), Thr-Lys-Ser-Lys-Gln-Leu (SEQ ID NO:47), His-Ser-Ser-Lys-Leu-Gln-Leu (SEQ ID NO:48), Asn-Lys-Ile-Ser-Tyr-Gln-Leu (SEQ ID NO:49), Ala-Thr-Lys-Ser-Lys-Gln-Leu (SEQ ID NO:50), Glu-His-Ser-Ser-Lys-Leu-Gln-Leu (SEQ ID NO:51), Gln-Asn-Lys-Ile-Ser-Tyr-Gln-Leu (SEQ ID NO:52), Glu-Asn-Lys-Ile-Ser-Tyr-Gln-Leu (SEQ ID NO:53), Ala-Thr-Lys-Ser-Lys-Gln-His-Leu (SEQ ID NO: 55), or His-Ser-Ser-Lys-Leu-Gln-Leu (SEQ ID NO:56). As noted, further amino acids can comprise $X_{-1}$.

Further examples of the peptides of the invention are constructed as analogs of, derivatives of, and conservative variations on the amino acids sequences disclosed herein. Thus, the broader group of peptides having hydrophilic and hydrophobic substitutions, and conservative variations are encompassed by the invention. The term "isolated" as used herein refers to a peptide substantially free of proteins, lipids, nucleic acids, for example, with which it is naturally associated. Those of skill in the art can make similar substitutions to achieve peptides with greater activity and/or specificity toward PSA. For example, the invention includes the peptide sequences described above, as well as analogs or derivatives thereof, as long as the bioactivity of the peptide remains. Minor modifications of the primary amino acid sequence of the peptides of the invention may result in peptides which have substantially equivalent activity as compared to the specific peptides described herein. Such modifications may be deliberate, as by site-directed mutagenesis or chemical synthesis, or may be spontaneous. All of the peptides produced by these modifications are included herein, as long as the biological activity of the original peptide remains, i.e., susceptibility to cleavage by PSA.

Further, deletion of one or more amino acids can also result in a modification of the structure of the resultant molecule without significantly altering its biological activity. This can lead to the development of a smaller active molecule which would also have utility. For example, amino or carboxy terminal amino acids which may not be required for biological activity of the particular peptide can be removed. Peptides of the invention include any analog, homolog, mutant, isomer or derivative of the peptides disclosed in the present invention, as long as the bioactivity as described herein remains. All peptides were synthesized using L-amino acids; however, D-forms of the amino acids can be synthetically produced.

The peptides of the invention include peptides which are conservative variations of those peptides specifically exemplified herein. The term "conservative variation" as used herein denotes the replacement of an amino acid residue by another, biologically similar residue. Examples of conservative variations include the substitution of one hydrophobic residue, such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic for aspartic acids, or glutamine for asparagine, and the like. Neutral hydrophilic amino acids which can be substituted for one another include asparagine, glutamine, serine, and threonine. The term "conservative variation" also includes the use of a substituted amino acid in place of an unsubstituted parent amino acid provided that antibodies raised to the substituted polypeptide also immunoreact with the unsubstituted polypeptide. Such conservative substitutions are within the definition of the classes of the peptides of the invention with respect to X positions which may be any of a number of amino acids. The peptides which are produced by such conservative variation can be screened for suitability of use in the prodrugs of the invention according to the methods for selecting prodrugs provided herein.

A wide variety of groups can be linked to the carboxy terminus of $X_1$ or $X_{-1}$. Notably, therapeutic drugs can be linked to this position. In this way, advantage is taken of the PSA-specificity of the cleavage site, as well as other functional characteristics of the peptides of the invention. Preferably, the therapeutic drugs are linked to the carboxy terminus either directly or through a linker group. The direct linkage is preferably through an amide bond, in order to utilize the proteolytic activity and specificity of PSA. If the connection between the therapeutic drug and the amino acid sequence is made through a linker, this connection is also preferably made through an amide bond, for the same reason. The linker may be connected to the therapeutic drug through any of the bond types and chemical groups known to those skilled in the art. The linker may remain on the therapeutic drug indefinitely after cleavage, or may be removed soon thereafter, either by further reactions with external agents, or in a self-cleaving step. Self-cleaving linkers are those linkers which can intra molecularly cyclized and release the drug, or undergo spontaneous $S^N1$ solvolysis and release the drug upon peptide cleavage. Such linkers are for example 2,2-dialkyl-2-(2-anisyl)acetic acid, described in Atwell et al., *J. Med. Chem.*, 37:371-380, (1994), and p-amidobenzyloxycarbonyl, described in Carl et al., *J. Med. Chem.*, 24:479-480, (1981).

Further useful examples are provided in these references. Other materials, such as detectable labels or imaging compounds can be linked to the peptide. Additionally, there can be up to 10 further amino acids at position $X_1$. In certain embodiments, the amino acids linked to $X_1$ at this position are leucine, threonine, serine or histidine. Groups can also be linked to the amino terminus of $X_5$, including such moieties as antibodies, and peptide toxins, including the 26 amino acid toxin, melittin and the 35 amino acid toxin, cecropin B, for example. Both of these peptide toxins have shown toxicity against cancer cell lines.

The length of the amino acid sequence plays a role in the ability of PSA to cleave the peptide, with at least a tetrapeptide required for activity. Tetrapeptides as recited above typically are not as soluble as hexapeptides, although PSA cleavage activity is similar. One skilled in the art will be able to readily identify specific groups to improve the water solubility of the peptides of the invention. Among the groups which should be considered are polysaccharides, including dextrans, cyclodextrins, starches and the like, including derivatives thereof. Therapeutic drugs which are water soluble may be linked to the peptides of the invention, thereby imparting water solubility to the complexes as a whole. The peptides of the invention may also contain conventional capping groups connected to the amino terminus of the peptide to prevent endopeptidase activity from degrading the peptide. Such capping groups include acetyl, succinyl, benzyloxycarbonyl, glutaryl, morpholinocarbonyl, and many others known in the art.

Amino acid sequences can be constructed that contain highly specific cleavage sites for PSA. The highly PSA-specific cleavage sites of the invention are cleaved by PSA to yield at least 5 picomoles of cleaved peptide per minute per 200 picomoles of PSA. Preferably, the peptides contain PSA-specific cleavage sites that yield at least 10 picomoles of cleaved peptide per minute per 200 picomoles of PSA. Most preferably, such cleavage sites yield at least 15 picomoles of cleaved peptide per minute per 200 picomoles of PSA.

Amino acid sequences can be constructed that are highly selective towards cleavage by PSA, so that cleavage by other purified extracellular proteases is minimized. Preferably, the peptides of the invention are cleaved by extracellular proteases other than PSA to yield not more than 4.0 picomoles of cleaved peptide per minute per 200 picomoles of purified extracellular non-PSA proteases. More preferably, the peptides are cleaved to yield not more than 2.0 picomoles of cleaved peptide per minute per 200 picomoles of purified extracellular non-PSA enzyme. Most preferably, not more than 2.0 picomole per minute of peptide are cleaved per 200 picomoles of purified extracellular non-PSA enzyme.

Highly PSA-specific amino acid sequences can be constructed that are also stable toward cleavage in sera. Preferably, the peptides containing this sequence yield at most 2.0 picomoles per minute of cleaved peptide in human serum. More preferably, the peptides containing this sequence yield at most 1.75 picomoles per minute of cleaved peptide in human serum. Most preferably, at most 1.5 picomoles per minute of cleaved peptide are yielded by enzymes found in human serum.

The preferred amino acid sequences of the invention are also highly selective towards cleavage by PSA as compared to purified intracellular proteases. Preferably, the peptides of the invention are cleaved by intracellular proteases other than PSA to yield not more than 35 picomoles of cleaved peptide per minute per 200 picomoles of purified intracellular protease. More preferably, the peptide do not yield more than 20 picomoles of cleaved peptide. Most preferably, not more than 5 picomoles of cleaved peptide are produced upon cleavage by purified intracellular proteases other than PSA. While not wishing to be bound by any particular theory, it is believed that essentially no pathogenic effects arise from cleavage of the peptides of the compositions of the invention through intracellular proteases, and that these proteases do not play a significant role in the activation of the therapeutic drugs of the invention.

PMSA Introduction

PSMA is expressed in high levels by prostate, and other, cancer cells, but not by normal cells. The specific targeting of the killing ability of therapeutic drugs to prostate, and other, cancer cells is enabled. Therapeutic drugs, for example, thapsigargins modified in the 8-position, are directly or indirectly coupled to the a-amino, or side-chain carboxyl of a peptide including dicarboxylic acid-containing amino acids or amidated analogs thereof, for example, glutamic acid, aspartic acid, glutamine or asparagine. Linking groups can be bonded between the drugs and the peptides.

In certain aspects of the invention peptides are involved that contain a cleavage site specific for prostate specific membrane antigen (PSMA). These peptides are efficiently and specifically cleaved by PSMA. These peptides are useful for substantially inhibiting the non-specific toxicity of the therapeutic agents prior to the agents coming in proximity to tissue containing PSMA. The prodrugs of the invention comprise peptides containing a cleavage site specific for PSMA, and therapeutic drugs. The presence of the peptides substantially converts the therapeutic drug into an inactive prodrug. The prodrugs do not show significant non-specific toxicity, but in environments where PSMA is found, the prodrugs become activated upon peptide cleavage, releasing the therapeutic drug, which then exhibits its inherent non-specific toxicity.

PSMA Specific Peptides

In one aspect, the invention features prodrugs including a peptide containing an amino acid sequence that includes a cleavage site specific for PSMA or an enzyme having a proteolytic activity of PSMA. Prodrugs are designed that can be activated by the pteroyl poly-γ-glutamyl carboxypeptidase (folate hydrolase) activity of PSMA. Gamma glutamyl hydrolase (GGH) is secreted by hepatocytes and by a variety of tumor cell types and GGH activity is present in human serum. Therefore, effective side chain-linked substrates are desirably specifically hydrolyzed by PSMA with minimal hydrolysis by GGH.

The PSMA cleavage site includes at least the dipeptide, $X_1X_2$. This peptide contains the amino acids Glu or Asp at position $X_1$. $X_2$ can be Glu, Asp, Gln, or Asn. Tripeptides $X_1X_2X_3$ are also suitable, with $X_1$ and $X_2$ defined as before, with $X_3$ as Glu, Asp, Gln or Asn. Tetrapeptides $X_1X_2X_3X_4$ are also suitable, with $X_1$-$X_3$ defined as above, and with $X_4$ as Glu, Asp, Gln or Asn. Pentapeptides $X_1X_2X_3X_4X_5$ are also suitable, with $X_1$-$X_4$ defined as above, and with $X_5$ as Glu, Asp, Gln or Asn. Hexapeptides $X_1X_2X_3X_4X_5X_6$ are also suitable, with $X_{1-5}$ defined as above, and with $X_6$ as Glu, Asp, Gln or Asn. Further peptides of longer sequence length can be constructed in similar fashion.

Generally, the peptides are of the following sequence: $X_1 \ldots X_n$, where n is 2 to 30, preferably 2 to 20, more preferably 2 to 15, and even more preferably 2 to 6, where $X_1$ is Glu, Asp, Gln or Asn, but is preferably Glu or Asp, and $X_2$-$X_n$ are independently selected from Glu, Asp, Gln and Asn. Some preferred peptide sequences are as above, except that $X_2$-$X_{n-1}$ are independently selected from Glu, and Asp, and $X_n$ is independently selected from Glu, Asp, Gln and Asn. The length of the peptide can be optimized to allow for efficient PSMA hydrolysis, enhanced solubility of therapeutic drug in aqueous solution, if this is needed, and limited non-specific cytotoxicity in vitro.

Among the a-linked dipeptides, Asp-Glu, Asp-Asp, Asp-Asn and Asp-Gln are preferably employed for use in the prodrugs described herein. Among the all a-linked tripeptides, Glu-Glu-Glu, Glu-Asp-Glu, Asp-Glu-Glu, Glu-Glu-Asp, Glu-Asp-Asp, Asp-Glu-Asp, Asp-Asp-Glu, Asp-Asp-Asp, Glu-Glu-Gln, Glu-Asp-Gln, Asp-Glu-Gln, Glu-Glu-Asn, Glu-Asp-Asn, Asp-Glu-Asn, Asp-Asp-Gln, and Asp-Asp-Asn are preferably employed for use in the prodrugs described herein. Tripeptides containing Gln or Asn in positions $X_2$ can also be desirably employed. Longer all a-linked peptides may also be employed for use in the prodrugs described herein, and such peptides with Gln or Asn in any positions X2-Xn can also be desirably employed.

Side Chain Linkages

Side-chain linkages PSMA is also able to hydrolyze a variety of side chain-linked peptides. Particular side chain-linked, for example, γ-linked peptides are not specific for PSMA, but can also hydrolyzed by GGH. Some preferred peptides take advantage of the dual ability of PSMA to hydrolyze certain a- and side-chain linkages between aspartyl, and glutamyl residues.

Among the side chain-linked dipeptides, Glu*Asp, Glu*Asn, Glu-'Glu, Glu*Gln, Asp*Asp, Asp*Glu, Asp*Asn, and Asp*Gln can be employed for use in the prodrugs described herein. Among the all side chain-linked tripeptides, Glu*Glu*Glu, Glu*Asp*Glu, Asp*Glu*Glu, Glu*Glu*Asp, Glu*Asp*Asp, Asp*Glu*Asp, Asp*Asp*Glu, Asp*Asp*Asp, Glu*Glu*Gln, Glu*Asp*Gln, Asp*Glu*Gln, Glu*Glu*Asn, Glu*Asp*Asn, Asp*Glu*Asn, Asp*Asp*Gln, and Asp*Asp*Asn can be preferably employed for use in the prodrugs described herein. Longer peptides which of analogous sequences can also be employed for use in the prodrugs described herein.

Mixed Peptides

Some preferred peptides include a PSMA-hydrolyzable, a-linked dipeptide "cap" that are not substrates for GGH, and are more specific PSMA substrates. Combination a- and side chain-linked PSMA substrates can be highly efficient and specific. For example, Glu*Glu*Glu*Asp-Glu (SEQ ID NO:58), and Glu*Glu*Glu*Asp-Gln (SEQ ID NO:59) have high stability in serum. Peptides containing two α-linkages and two γ-linkages, for example, Asp-Glu*Glu*Asp-Glu (SEQ ID NO:60) can be completely stable to hydrolysis in human and mouse plasma. A number of aspartate- and glutamate-containing linkers are depicted in FIG. 1. These particular linkers can be bonded to amine groups on therapeutic drugs.

The peptides listed are among those that are preferred: Glu*Glu*Glu*Asp-Glu (SEQ ID NO:58), Asp-Glu*Glu*Asp-Glu (SEQ ID NO:60), and Glu-Glu*Glu*Asp-Glu (SEQ ID NO:61). Numerous other peptides with mixed a- and side chain linkages and otherwise corresponding to the description herein can be readily envisioned and constructed by those of ordinary skill in the art.

The peptides of the invention are preferably not more than 20 amino acids in length, more preferably not more than 6 amino acids in length. Some peptides which are only two or three amino acids in length are quite suitable for use in the prodrugs described herein. Some preferred amino acid sequences of the invention are linear.

However, multiple linkage sites present on dicarboxylic amino acids may also be used to produce branched peptides. These branched peptides could include a therapeutic agent coupled to each amino acid of the peptide chain, such that cleavage of individual amino acids from the peptide chain by the enzymatic activity of PSMA releases multiple molecules of therapeutic agent.

Further examples of the peptides of the invention are constructed as analogs of, derivatives of, and conservative variations on the amino acids sequences disclosed herein. The term "isolated" as used herein refers to a peptide substantially free of proteins, lipids, nucleic acids, for example, with which it is naturally associated.

Those of skill in the art can make similar substitutions to achieve peptides with greater activity and/or specificity toward PSMA. For example, the invention includes the peptide sequences described above, as well as analogs or derivatives thereof, as long as the bioactivity of the peptide remains. Minor modifications of the primary amino acid sequence of the peptides of the invention may result in peptides which have substantially equivalent activity as compared to the specific peptides described herein. Such modifications may be deliberate, as by site-directed mutagenesis or chemical synthesis, or may be spontaneous. All of the peptides produced by these modifications are included herein, as long as the biological activity of the original peptide remains, i.e., susceptibility to cleavage by PSMA.

Further, deletion of one or more amino acids can also result in a modification of the structure of the resultant molecule without significantly altering its biological activity. This can lead to the development of a smaller active molecule which would also have utility. For example, amino or carboxy terminal amino acids which may not be required for biological activity of the particular peptide can be removed. Peptides of the invention include any analog, homolog, mutant, isomer or derivative of the peptides disclosed in the present invention, as long as the bioactivity as described herein remains. All peptides were synthesized using L-amino acids, and these amino acids are preferred; however, D-forms of the amino acids can be synthetically produced.

The peptides of the invention include peptides which are conservative variations of those peptides specifically exemplified herein. The term "conservative variation" as used herein denotes the replacement of an amino acid residue by another, biologically similar residue. Examples of conservative variations include the substitution of one hydrophobic residue, such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic for aspartic acids, or glutamine for asparagine, and the like. Neutral hydrophilic amino acids which can be substituted for one another include asparagine, glutamine, serine, and threonin. The term "conservative variation" also includes the use of a substituted amino acid in place of an unsubstituted parent amino acid provided that antibodies raised to the substituted polypeptide also immunoreact with the unsubstituted polypeptide. Such conservative substitutions are within the definition of the classes of the peptides of the invention with respect to X positions which may be any of a number of amino acids. The peptides which are produced by such conservative variation can be screened for suitability of use in the prodrugs of the invention according to the methods for selecting prodrugs provided herein.

The peptides of the invention can be synthesized according to any of the recognized procedures in the art, including such commonly used methods as t-boc or fl-noc protection of alpha-amino groups. Both methods involve stepwise syntheses whereby a single amino acid is added at each step starting from the C-terminus of the peptide. (see, Coligan, et al., *Current Protocols in Immunology*, Wiley Interscience, 1991, Unit 9). Peptides of the invention can also be synthesized by the well-known solid phase peptide synthesis methods described in Merrifield, *J. Am. Chem. Soc.*, 85: 2149,1962), and Stewart and Young, *Solid Phase Peptide Synthesis*, (Freeman, San Francisco, 1969, pp. 27-62), using a copoly (styrene-divinylbenzene) containing 0.1-1.0 mM amine/gram polymer. Polyglutamated methotrexate was purchased from Schirks Laboratories. Other analogs were constructed using APA purchased from Sigma Chemical (St. Louis, Mo.). The peptides were synthesized with the appropriate blocking groups on the carboxyl groups, and the APA was coupled to the peptide using standard coupling chemistry. Such synthetic procedures are well known to those of ordinary skill in the art.

On completion of chemical synthesis, the peptides can be deprotected and cleaved from the polymer by treatment with liquid HF-10% anisole for about ¼ to 1 hour at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as solvent. Lyophilization of appropriate fractions of the column will yield the homogeneous peptide of peptide derivatives, which can then be characterized by such standard techniques as amino acid analysis, thin layer chromatography, high performance liquid chromatography, ultraviolet absorption spectroscopy, molar rotation, solubility, and quantitated by solid phase Edman Degradation.

The invention encompasses isolated nucleic acid molecules encoding the PSMA-specific peptides of the invention, vectors containing these nucleic acid molecules, cells harboring recombinant DNA encoding the PSMA-specific peptides of the invention, and fusion proteins which include the PSMA-specific peptides of the invention. Especially preferred are nucleic acid molecules encoding the polypeptides described herein.

The PSMA-specific peptides are cleaved by PSMA to yield at least 5 picomoles, preferably at least 10 picomoles, and most preferably at least 15 picomoles of cleaved peptide per minute per milligram of PSMA. Desirably, the peptides are highly selective towards cleavage by PSMA, so that cleavage by other purified extracellular proteases is minimized. The peptides disclosed herein are cleaved by extracellular proteases other than PSMA to yield not more than 4.0 picomoles, preferably not more than 2.0 picomoles, and more preferably not more than 1.0 picomole of cleaved peptide per minute per milligram of purified extracellular non-PSMA proteases. The peptides described herein are also stable toward cleavage in sera. The peptides containing this sequence yield at most 5%, preferably at most 2.5% and more preferably at most 1.0% cleaved peptide from uncleaved peptide in human serum over a 24-hour period.

Prodrug Compositions

A wide variety of entities can be linked to the a-amino terminus, the a-carboxy terminus, or the side chain of the peptide, preferably at $X_1$, but also at any position from $X_1$ to $X_{n-1}$. In some preferred embodiments, linkage between the entities and the peptide takes place at $X_1$, at either the amino terminus, or at the side chain.

Notably, therapeutic drugs can be linked to these positions, creating prodrugs. The therapeutic drugs that may be used in the prodrugs of the invention include any drugs which can be directly or indirectly linked to the PSMA-specifically cleavable peptides of the invention. Hydrolytic processing of prodrugs by PSMA results in a final product consisting of a therapeutic drug coupled to an amino acid, such as aspartate or glutamate. Preferred therapeutic drugs incorporate aspartic, glutamic acid or some other dicarboxylic acid into their structure and still maintain their therapeutic effect, for example, cytotoxicity. In this way, advantage is taken of the PSMA-specificity of the cleavage site, as well as other functional characteristics of the peptides of the invention. Preferred drugs are those that contain an acidic amino acid, for example Asp or Glu. The presence of an amino acid in the drug allows the formation of an amide bond between the drug and the peptide. This bond serves as the cleavage site for PSMA. As noted above, the peptides of the invention can be used to activate therapeutic drugs at PSMA producing tissue. The peptides which are useful in the prodrugs of the invention are those described above.

Other therapeutic drugs are required to have acidic amino acids introduced by chemical or biochemical synthesis, for example, sesquiterpene-γ-lactones, in particular sesquiterpene-γ-lactones, such as those belonging to the guaianolide, isoguaianolide, inuchineolide, germacranolide, illudins, and eudesmanolide families of sesquiterpenoids. Alpha-methylene sesquiterpenoids in these families are of particular interest. These include estafiatin, grossheimin, inuchinenolide, arglabin, artemisinin, illudin A-S, parthenin, and parthenolide, thapsigargin and their derivatives, such as thapsigargicin and many others known to those skilled in the art. Thapsigargin and its derivatives are believed to act by inhibiting the SERCA pump found in many cells.

Preferably, therapeutic drugs are linked to the peptide either directly or indirectly, through a linker group. The direct linkage can be made conveniently through an amide bond, for example. If therapeutic drugs are linked to the peptide through the a-amino group of $X_1$, an amide bond is conveniently created with a carboxyl present on the therapeutic drug, or with a carboxyl present on any linker. If therapeutic drugs are linked to the peptide through the side chain- or α-carboxyl of $X_1$, or any other amino acid in the peptide, an amide bond is conveniently created with an amino group present on the therapeutic drug, or with an amino group present on any linker.

The linker may be connected to the therapeutic drug through any of the bond types and chemical groups known to those skilled in the art. Therapeutic drugs can also be coupled directly to the α-amine of an amino acid of peptides via a linker.

The linker can either remain attached to the drug or be cleaved. In embodiments in which the linker remains attached to the drug, the linker can be any group which does not substantially inhibit the non-specific toxicity of the drug after cleavage from the peptide. Suitable linkers are primary amine containing alkanol, alkenyl, and arenoyl substituents. Examples of such linkers are $CO-(CH=CH)_{n1}-(CH_2)_{n2}-Ar-NH_2$, $CO-(CH_2)n2-(CH=CH)_{n1}-Ar-NH_2$, $CO-(CH_2)_{n2}-(CH=CH)_{n1}-CO-NH-Ar-NH_2$ and $CO-(CH=CH)_{n1}-(CH_2)n_2-CO-NH-Ar-NH_2$, $CO(CH_2)_n-Ar-(CH_2)_m-NH_2$, and substituted variations thereof, where n1 and n2 are from 0 to 5, and Ar is any substituted or unsubstituted aryl group. Substituents which may be present on Ar include short and medium chain alkyl, alkanoxy, aryl, aryloxy, and alkenoxy groups, nitro, halo, and primary secondary or tertiary amino groups, as well as such groups connected to Ar by ester or amide linkages. Amino acids can also serve as linkers. A dicarboxylic acid linker can be used, such as the 12-carbon linker 12-carboxydodecanoate for (12-CDT-Asp). This analog can then be linked via either the α-carboxyl or side-chain carboxyl to a longer peptide chain.

Figure 2A:
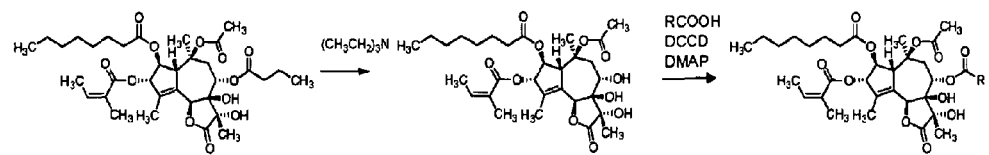
FIG. 2A is an illustration of a method developed for selective cleavage of thapsigargin to give the debutanoyl derivative, which can be selectively reesterified with appropriate acids and is used for introducing phenolic acid containing side chains.
Figure 2B:
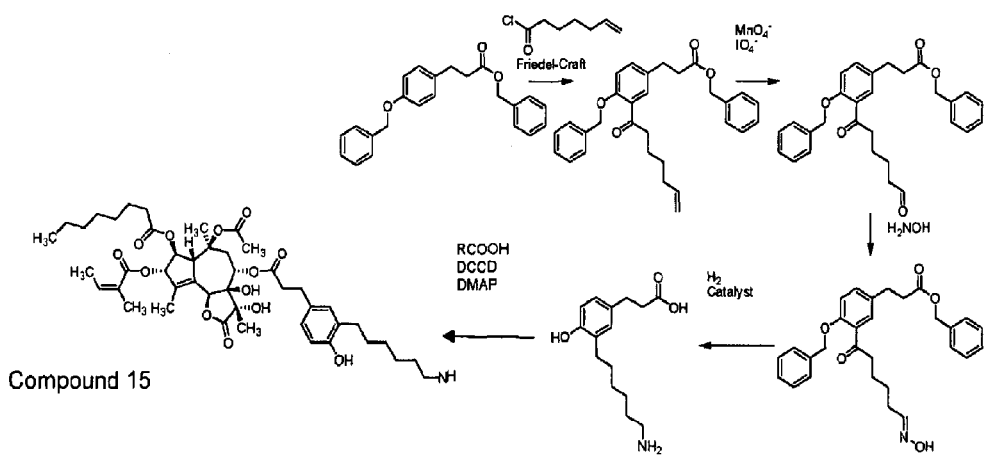
FIG. 2B is an illustration of a method for introduction of a phenol group. More specifically, in the case of TG, a phenolic group can be introduced into the linker to generate a TG compound labeled 15.
Figure 2C:
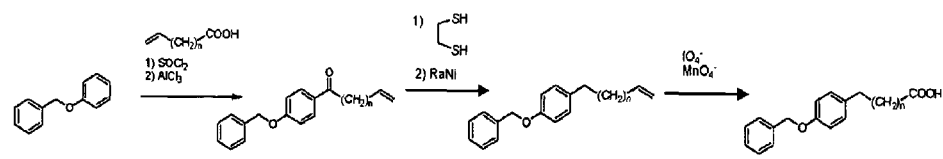
FIG. 2C is a method for development of a synthetic method for preparing the starting ω-(4-benzoxyphenyl)alkanoic acid to position the phenolic group which can be varied to produce optimal linker for PSMA hydrolysis.
Figure 2D:
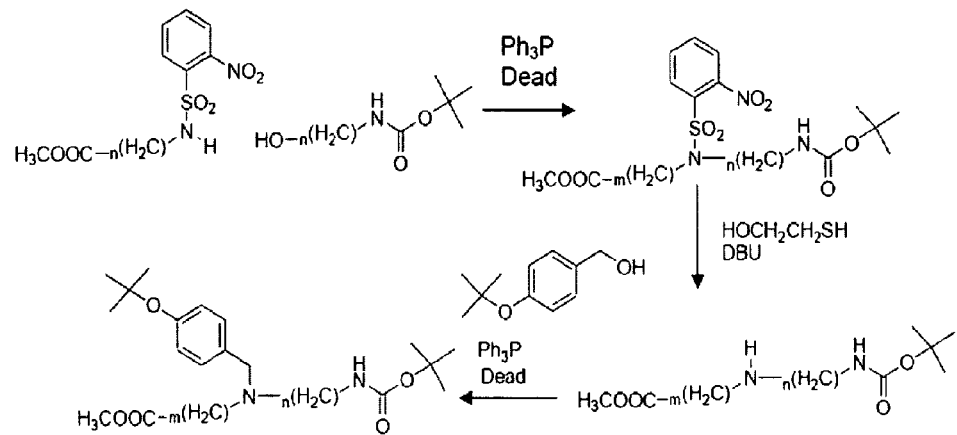
FIG. 2D is an alternative strategy for inclusion of the phenolic ring in the 8-O-acyl group. More specifically, the methyl ester is cleaved to give the carboxylic acid, which is coupled to DBTG according to the method shown in FIG. 4A. Finally the tert-butoxygroup is cleaved with acid to give the phenolic thapsigargin analog.

More particularly, the inventors have previously established that the O-8 acyl group is located between the transmembrane moieties of the SERCA pump. Accordingly the 12ADT has been found to inhibit SERCA as efficiently as does TG. The advantage of 12ADT is that this molecule contains an amino group enabling condensation with a peptide which is a substrate for PSMA. This location of the O-8 acyl group between the transmembrane moieties offers some possibilities for introduction of a voluminous and stiff phenolic group that can be iodinated. The inventors have also previously developed a method for selective cleavage of thapsigargin to give the debutanoyl derivative, which can be selectively reesterified with appropriate acids as indicated in FIG. 2A. This is used for introducing the phenolic ring acid containing side chains. The flexibility of the methods mentioned below enables an arbitrary location of the phenolic group in the O-8 acyl group of the class I analogs. In the following figures (FIG. 2B-2E) some methods of introduction of a phenol group are suggested. In the case of TG, a phenolic group might be introduced into the linker according to the procedure given in FIG. 2B. Compound 15 is an example of this class of analogs. A dicarboxylic acid linker can be used, such as the 12-carbon linker 12-carboxydodecanoate, shown, for example, for (12-ADT-Asp) in FIG. 3. This analog can then be linked via either the α-carboxyl or side-chain carboxyl to a longer peptide chain.

In certain embodiments, the linker is self-cleaving. Self-cleaving linkers are those which are disposed to cleave from the drug after the cleavage of the peptide by PSMA. The linkers generally contain primary amines which form amide bonds to the carboxy terminus of the peptide sequence. The linkers can also contain a carboxylic acid which forms an amide bond to a primary amine found on the drug. In such embodiments, the linker is not required to be non-interfering with the non-specific toxicity of the drug, as long as it is cleaved within a period of time short enough to allow the drug to remain localized where it has been activated, or within a period of time short enough to prevent inactivation by any means.

The linker may remain on the therapeutic drug indefinitely after cleavage, or may be removed soon thereafter, either by further reactions with external agents, or in a self-cleaving step. Self-cleaving linkers are those linkers which can intramolecularly cyclize and release the drug, or undergo spontaneous $S_N1$ solvolysis and release the drug upon peptide cleavage. Such linkers are for example 2,2-dialkyl-2-(2-anisyl) acetic acid, described in Atwell et al., *J. Med. Chem.*, 37: 371-380, (1994), and p-amidobenzyloxycarbonyl, described in Carl et al., *J. Med. Chem.*, 24: 479-480, (1981). Further useful examples are provided in these references. Other materials, such as detectable labels or imaging compounds, can be linked to the peptide. Groups can also be linked to the carboxy side chains of $X_1$, to $X_{n-1}$, including such moieties as antibodies, and peptide toxins, including the 26 amino acid toxin, melittin and the 35 amino acid toxin, cecropin B, for example. Both of these peptide toxins have shown toxicity against cancer cell lines.

The longer-length, negatively-charged, substrates can serve two additional purposes: first, they help to make highly lipophilic toxins, for example, TG analogs, more water soluble; second, the highly charged prodrug will be less likely to cross the plasma membrane, further limiting non-specific cytotoxicity.

The following prodrugs are representative:

(1) 12ADT-Glu*Glu*Glu*Asp-Glu; (SEQ ID NO: 58)

(2) 12ADT*Glu-Glu*Glu*Asp-Glu (SEQ ID NO: 61)

(3) 12CDT-Glu*Glu*Glu*Asp-Glu (SEQ ID NO: 58)

(4) 12ADT-Asp-Glu*Glu*Asp-Glu (SEQ ID NO: 60)

(5) 12CDT-Asp-Glu*Glu*Asp-Glu (SEQ ID NO: 60)

The prodrugs are hydrolyzed by PSMA and release the corresponding Asp- or Glu-containing TG analogs or the TG analog itself, and also lack potent cytotoxicity when not metabolized by PSMA. Non-PSMA producing TSU-PrI human prostate cancer cell line is exposed to each of the prodrugs at doses that are approximately 50 times the $LD_{50}$ for the corresponding free TG analog. Against the TSU prostate cancer cell line, 12ADT-Glu has an $LD_{50}$ value for killing of around 50 nM. The prodrugs are hydrolyzed by PSMA and have a dose-responsive ability to kill PSMA-producing LNCaP and CWR22R cells in vitro, based upon loss of clonogenic abilities. The activity of these cell lines is approximately 13 pmoles NAAG hydrolyzed/min/mg protein for LNCaP and approximately 20 pmoles NAAG hydrolyzed/min/mg protein for CWR22R cells, using radiolabeled $^3$H-NAAG. These prodrugs are tested against TSU cells that have been transduced with a lentiviral vector carrying the PSMA gene. This TSU-PSMA cell line produces amounts of PSMA that are similar to LNCaP as determined by Western Blot. The activity of the PSMA from this line is comparable to the LNCaP and CWR22R lines (that is, approximately 18 pmoles NAAG hydrolyzed/min/mg protein). This TSU-PSMA line is used to determine the therapeutic index by comparing cytotoxic activity of the prodrugs against this PSMA-producing line and the wild type TSU cells. Using these data, $LD_{50}$ values for all the tested compounds is calculated. To be considered selective, the preferred prodrugs have a >20-fold difference in ability to kill TSU-PSMA vs. TSU wild type cells.

The prodrugs of the invention are not taken up by the cells, but are cleaved extracellularly by PSMA to yield at least 5 picomoles, preferably at least 10 picomoles, and more preferably at least 15 picomoles of therapeutic drug per minute per milligram of PSMA. Preferably, the prodrugs of the invention are cleaved by extracellular proteases other than PSMA to yield not more than 4.0 picomoles, preferably not more than 2.0 picomoles, and more preferably not more than 1.0 picomole of therapeutic drug per minute per milligram of purified extracellular non-PSMA proteases. The prodrugs of the invention yield at most 5%, preferably at most 2.5%, and more preferably at most 1.0% of prodrug as therapeutic drug in human serum over a 24-hour period.

The prodrugs of the invention may also comprise groups which provide solubility to the prodrug as a whole in the solvent in which the prodrug is to be used. Most often the solvent is water. This feature of the invention is important in the event that neither the peptide nor the therapeutic drug is soluble enough to provide overall solubility to the prodrug. These groups include polysaccharides or other polyhydroxylated moieties. For example, dextran, cyclodextrin, starch and derivatives of such groups may be included in the prodrug of the invention.

Methods of Treatment Using Prodrugs

In certain embodiments, the present invention also provides methods of treating PSMA-producing cell proliferative disorders with the prodrugs of the invention. Hydrolytic processing of prodrugs by PSMA results in a final product consisting of a therapeutic drug or a therapeutic drug coupled to an amino acid, such as aspartate or glutamate. Preferred therapeutic drugs incorporate aspartic, glutamic acid or some other dicarboxylic acid into their structure and still maintain their therapeutic effect. Prodrugs can be tested for cytotoxicity against PSMA-producing LNCaP, CWR22R and the TSU-PSMA and wild type TSU human cancer cells.

The prodrugs of the invention and/or analogs or derivatives thereof can be administered to any host, including a human or non-human animal, in an amount effective to treat a disorder. The prodrugs of the invention can be administered parenterally by injection or by gradual infusion over time. The prodrugs can be administered intravenously, intraperitoneally, intramuscularly, subcutaneously, intracavity, or transdermally. Preferred methods for delivery of the prodrug include intravenous or subcutaneous administration. Other methods of administration will be known to those skilled in the art.

Preparations for parenteral administration of a prodrug of the invention include sterile aqueous or non-aqueous solutions, suspensions, and emulsions. Examples of non-aqueous solvents are propylene glycol, polyethylene glycol, vegetable oils, such as olive oil, and injectable organic esters, such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present, such as, for example, antimicrobials, anti-oxidants, chelating agents, and inert gases, and the like.

The term "cell-proliferative disorder" denotes malignant as well as non-malignant cell populations which often appear to differ from the surrounding tissue both morphologically and genotypically. Malignant cells (i.e., cancer) develop as a result of a multistep process. The PSMA-specific prodrugs of the invention are useful in treating malignancies of the various organ systems. Essentially, any disorder which is etiologically linked to PSMA expression could be considered susceptible to treatment with a PSMA-specific prodrug. One such disorder is a malignant cell proliferative disorder, for example. The term "therapeutically effective amount" as used herein for treatment of cell proliferative disorders refers to the amount of prodrug sufficient to cause a reduction in the number of unwanted cells. The term "therapeutically effective" therefore includes the amount of prodrug sufficient to prevent, and preferably reduce by at least 25%, and more preferably to reduce by 90%, the number of unwanted cells. The dosage ranges for the administration of prodrug are those large enough to produce the desired effect. Generally the dosage will vary with age, condition, sex, and extent of the disorder in the subject, and can be determined by one skilled in the art. The dosage can be adjusted by the individual physician in the event of any contraindications. In any event, the effectiveness of treatment can be determined by monitoring tumor ablation.

Methods of producing Prodrugs

The invention, in another aspect, provides a method of producing the prodrugs of the invention. This method involves linking a therapeutically active drug to a peptide of the invention. Such peptides are described above. After the drug and peptide are linked to produce a therapeutic prodrug composition, the non-specific toxicity of the drug is substantially inhibited. In certain embodiments, the peptide is linked directly to the drug. In other embodiments, the peptide is indirectly linked to the drug, the linkage occurring through a linker. In each case the amino terminus of the peptide is used for linking. The drug can be linked to the α-amine of the amino terminal amino acid or it can be linked to a carboxyl side-chain of an acidic amino acid at the amino terminus of the peptide, or at any position from $X_2$ to $X_{n-1}$, except when n is 2. That is, in an amino acid sequence $X_1 X_2 \ldots X_n$, the link is established through $X_1$ or $X_2$ to $X_{n-1}$ preferably through $X_1$. The therapeutic drug can contains a primary amine group or a carboxyl group to facilitate the formation of an amide bond with the peptide. Many acceptable methods of coupling carboxyl and amino groups to form amide bonds are knows to those of skill in the art.

The bonds of the amino acids in the peptide are sequentially cleaved by PSMA, releasing the therapeutic drug. Suitable linkers include any chemical group which contains a primary amine or carboxyl group. The linkers for use in the present invention include amino acids, primary amine- or carboxyl-containing alkyl, alkenyl or arenyl groups.

The connection between the linker and the therapeutic drug may be of any type known in the art, preferably covalent bonding. The linker group may remain attached to the therapeutic drug if its attachment does not significantly reduce the non-specific toxicity of the drug. In certain embodiments, the linker is a cleavable linker, which may be cleaved either by an external agent, or it may be a self-cleaving linker. External agents, which may affect cleavage of the linker, include enzymes, proteins, organic or inorganic reagents, protons and any other agents which do not affect the non-specific toxicity of the drug or prodrug.

In certain embodiments, the linker comprises an amino acid sequence. The sequence may be of any length, but is preferably between 1 and 10 amino acids, most preferably between 1 and 5 amino acids in length. Preferred amino acids are glutamate, aspartate, glutamine, asparagine, or amino acid sequences containing these amino acids, especially at their amino termini, although conservative variations of these amino acids may also be utilized. More preferably, the linker includes glutamate or aspartate.

Other groups may be added to the prodrugs of the invention, including those which render the prodrug soluble in water. These groups include polysaccharides or other polyhydroxylated moieties. For example, dextran, cyclodextrin and starch may be included in the prodrug of the invention.

Methods of Screening Tissue

In another aspect the invention provides a method of detecting PSMA-producing tissue using the peptides of the invention, as described above. The method is carried out by contacting a detectably labeled peptide of the invention with target tissue for a period of time sufficient to allow PSMA to cleave the peptide and release the detectable label. The detectable label is then detected. The level of detection is then compared to that of a control sample not contacted with the target tissue. Many varieties of detectable label are available, including optically based labels, such as chromophoric, chemiluminescent, fluorescent or phosphorescent labels, and radioactive labels, such as alpha, beta or gamma emitting labels. Examples of fluorescent labels include amine-containing coumarins, such as 7-amino-4-methylcoumarin, 7-amino-4-trifluoromethyl, and other amine-containing fluorophores, such as 6-aminoquinoline, and rhodamines, including rhodamine 110. Other examples of fluorescent labels include those containing carboxyl moieties, such $^{125}$I, $^{124}$I and $^{132}$I. Examples of chromophoric labels (those that have characteristic as FITC. Examples of radioactive labels include beta emitters, such as $^3$H, absorption spectra) include nitroaromatic compounds, such as p-nitroaniline. Examples of chemiluminescent labels include luciferins, such as 6-amino-6-deoxyluciferin.

Preferably, the choice of detectable label allows for rapid detection and easily interpretable determinations. Detectable labels for use in the invention preferably show clearly detectable differences between detection from the cleaved and uncleaved state.

The invention provides a method for detecting a cell proliferative disorder which comprises contacting a PSMA-specific peptide with a cell suspected of having a PSMA-production associated disorder and detecting cleavage of the peptide. The peptide reactive with PSMA is labeled with a compound which allows detection of cleavage by PSMA. For purposes of the invention, a peptide specific for PSMA may be used to detect the level of enzymatically active PSMA in cell membranes, and potentially in saliva, blood, or urine. Any specimen containing a detectable amount of antigen can be used. The level of PSMA in the suspect cell can be compared with the level in a normal cell to determine whether the subject has a PSMA-production associated cell proliferative disorder. Preferably the subject is human.

Methods of Screening Prodrugs

The invention also provides a method of selecting potential prodrugs for use in the invention. The method generally consists of contacting prodrugs of the invention with PSMA-producing tissue and non-PSMA producing tissue in a parallel experiment. "PSMA-producing tissue" as used herein is tissue that produces at least 1 ng enzymatically active PSMA per gram of tissue, or at least 1 ng of enzymatically active PSMA/10 cells/24 hours from cells. The prodrugs which exert toxic effects in the presence of PSMA-producing tissue, but not in the presence of non-PSMA producing tissue are suitable for the uses of the invention. In other words, the $LC_{50}$ concentration of the prodrug in the presence of PSMA-producing tissue is at least 3 times lower, more preferably at least 20 times lower, and most preferably at least 100 times lower than the $LC_{50}$ concentration of the prodrug in the presence of non-PSMA producing tissue.

Method of Determining PSMA Activity

The invention also provides a method of determining the activity of PSMA. The method generally consists of contacting detectably labeled prodrugs of the invention with samples may come from fluid drawn from PSA-producing tissue, from tissue culture media, from serum, saliva or urine, or any source which contains PSMA. The cleavage of peptide which takes place by PSMA results in the release of a detectable label, which is subsequently detected. This detection level is compared to the detection level which is found upon performing a parallel experiment in which the PSMA-containing sample is a standard solution made up from purified PSMA as described, for example, in Lapidus et al, *Prostate*, (2000) 45: 350-354. This comparison results in a determination of the activity of the PSMA which is present in the sample, given a correction for any differences in PSMA concentration which may exist. Such correction may be accomplished directly by adjusting the concentrations of the standard and sample solutions to match each other or by mathematical correction means.

Methods of Imaging Tissue

The invention in another aspect, provides a method of imaging soft tissue or bone metastases by providing peptides of the invention linked to lipophilic imaging labels that can be detected by imaging techniques, for example, positron emission tomography (PET). This method is accomplished generally by administering a peptide of the invention linked to a primary amine-containing lipophilic label to a subject having or suspected of having a PSMA-producing associated cell proliferative disorder. The peptide is selectively cleaved from the lipophilic imaging label where enzymatically active PSMA occurs in the subject (i.e., PSMA producing tissues). The lipophilic imaging label is then drawn into the membranes of cells in the vicinity.

After a period of time sufficient to allow cleavage of the peptide by PSMA, and to allow the uncleaved peptide to be sufficiently cleared from the subject to allow reliable imaging, the subject is imaged. The lipophilic label accumulates in the soft tissue or bone that produces PSMA, and allows a diagnosis of the subject. Suitable labels for PET scanning are radionuclides, such $^{18}F$, $^{11}C$, $^{13}N$ and a $^{15}O$, and any other positron emitters known in the art. Lipophilicity can be engineered into the label by introducing the label into lipophilic fragments or moieties known to those in the art, by methods known to those skilled in the art.

Radiolabeled Thapsigargin Analogs Incorporated into Protease Activated Prodrugs

In certain embodiments of the present invention, the core of the presently disclosed drugs is thapsigargin, which is a non-specific, highly cytotoxic agent. As noted earlier thapsigargin acts on the SERCA-pump of the cell, initiating a cellular influx of Ca2+ and subsequently apoptosis. Thapsigargin, can be inactivated by the binding of an amino acid sequence thus making an inactivated pro-drug. The amino acid sequence can be modeled so that it can be recognized and subsequently cleaved by proteases, such as PSA or PMSA. Although normal prostate tissue has adequate amounts of both PSA and PMSA, the concentration is considerable higher in malignancy high grade malignancy and even metastasis. Therefore, PSA and PSMA are favorable to use as targets for treating and diagnosing cancer.

To facilitate imaging, a phenol ring is added to the free-drug molecule and it can be used to link radio tracers, including, but not limited to, $^{125}I$. When the amino acid sequence is clipped by PSA or PSMA, the now activated free-drug is taken up by the prostate cancer cells, making it possible to perform targeted imaging of the cancer cells. Although the dosage for imaging is much lower than a therapeutically dose the imaging drugs still hold some cell killing properties, resulting in targeted therapy.

Figure 4A:
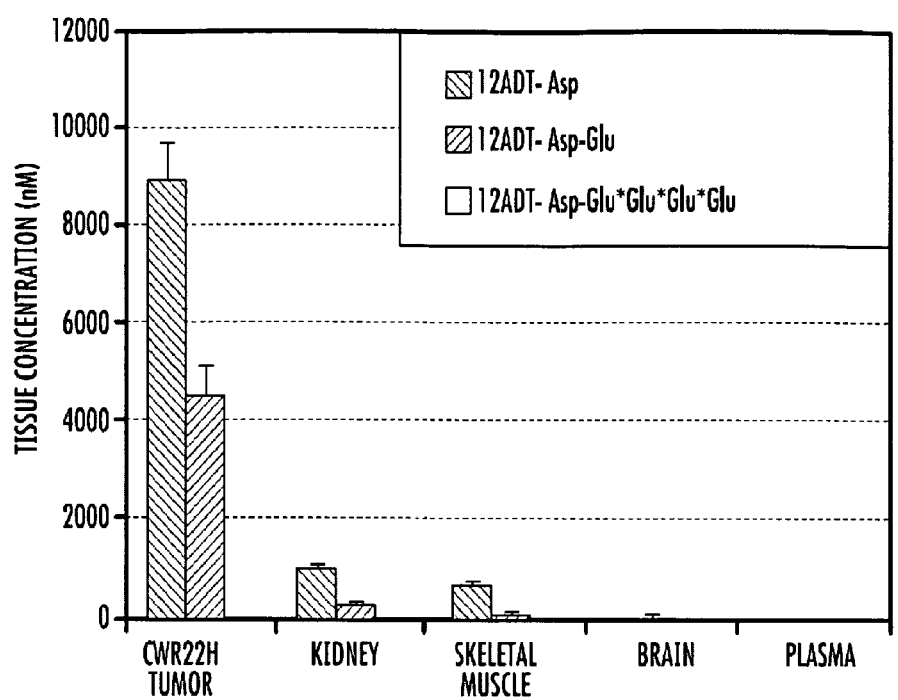
Figure 5A:
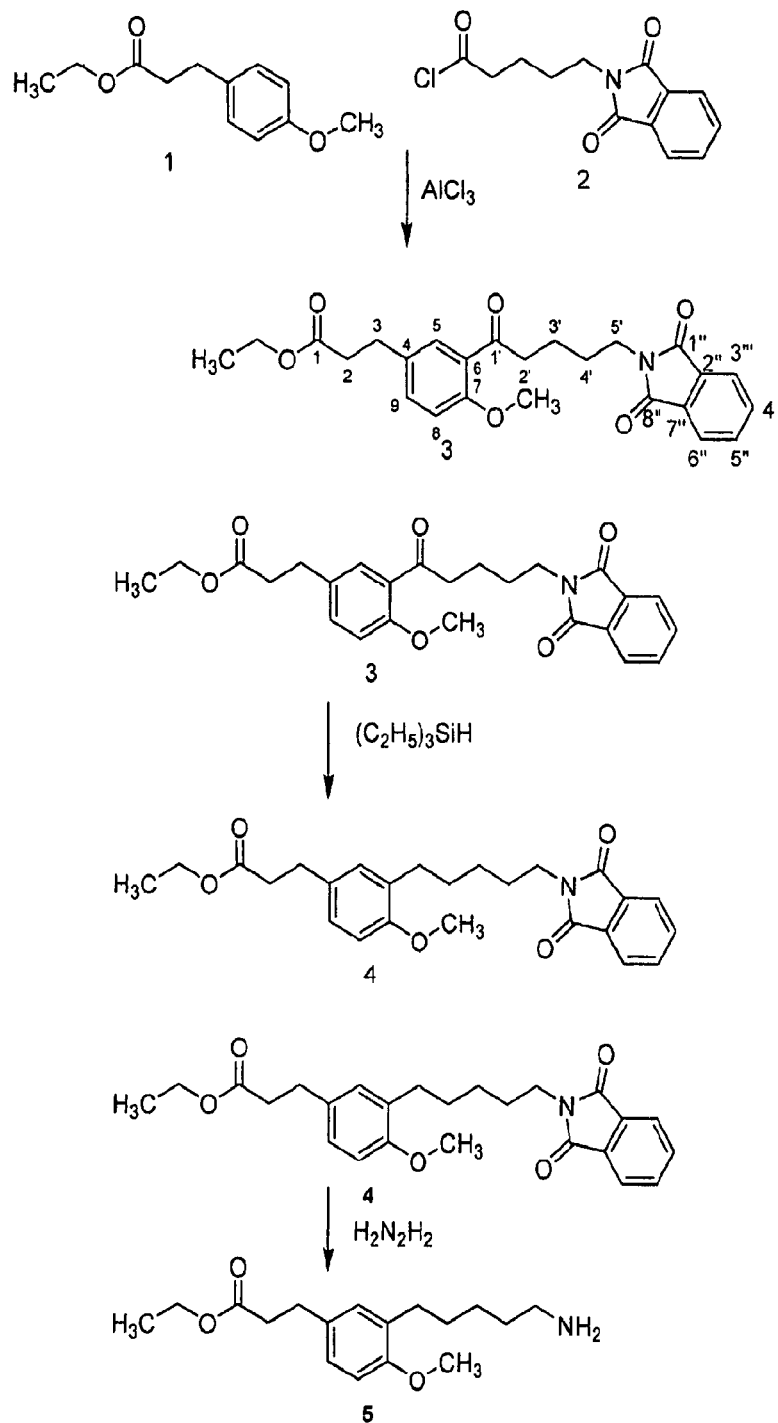
FIG. 5A-5E. Schematic diagrams for the synthesis of compound 14.
Figure 5B:
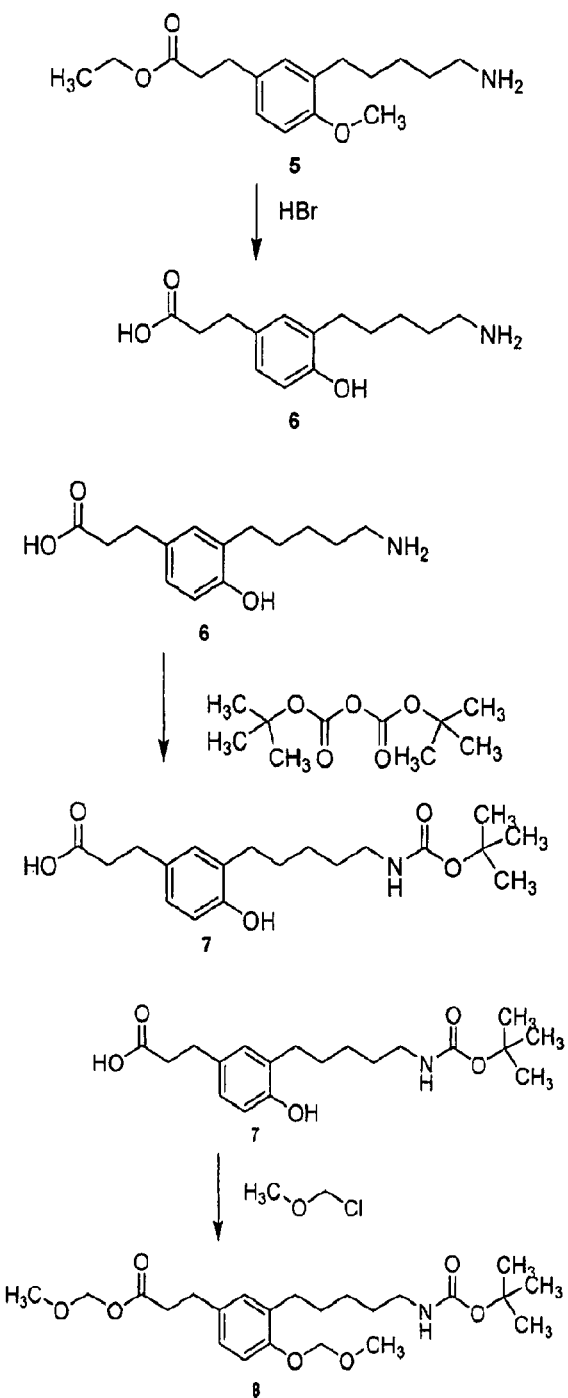
Figure 5C:
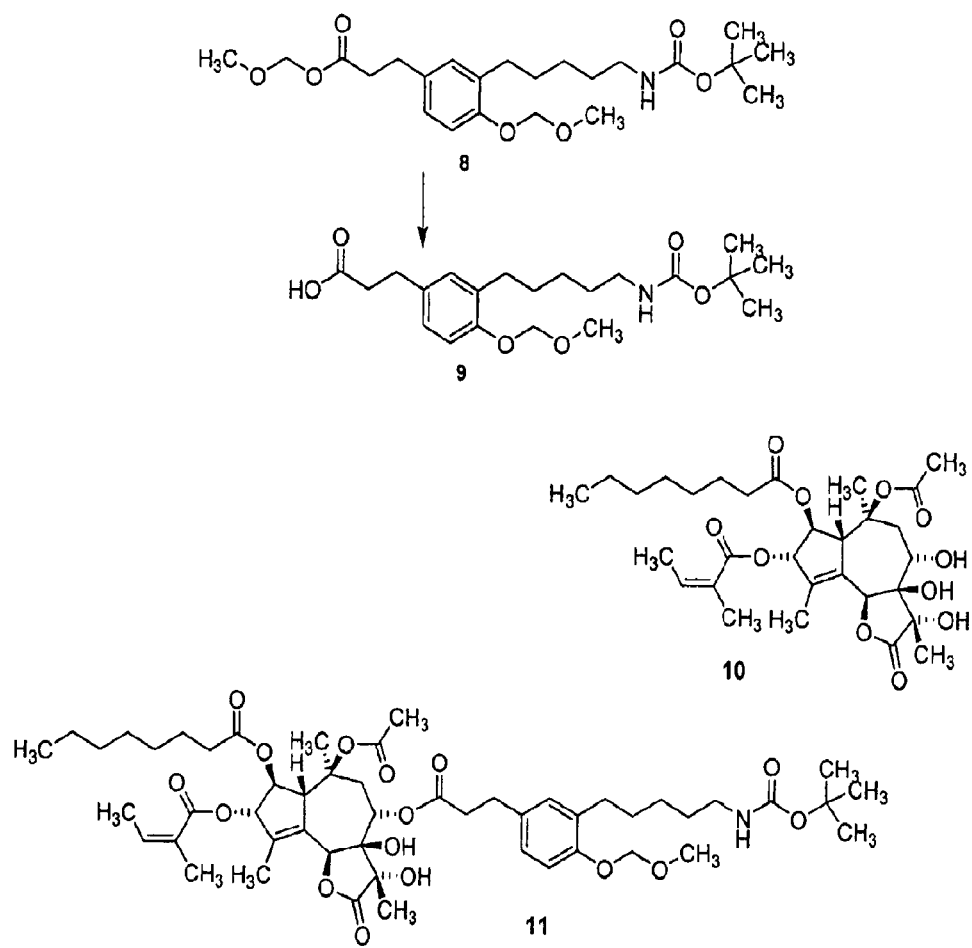
Figure 5D:
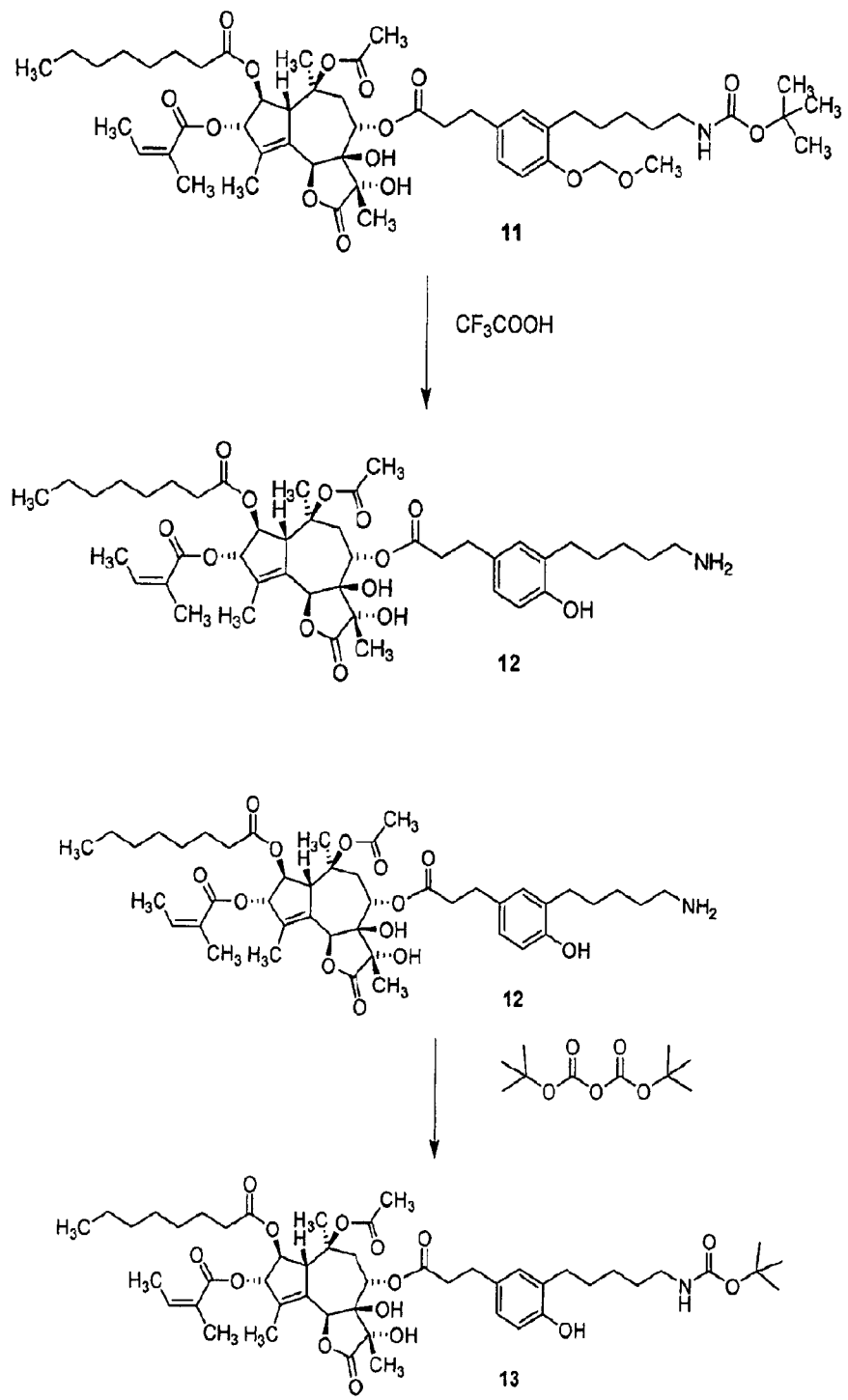
Figure 5E:
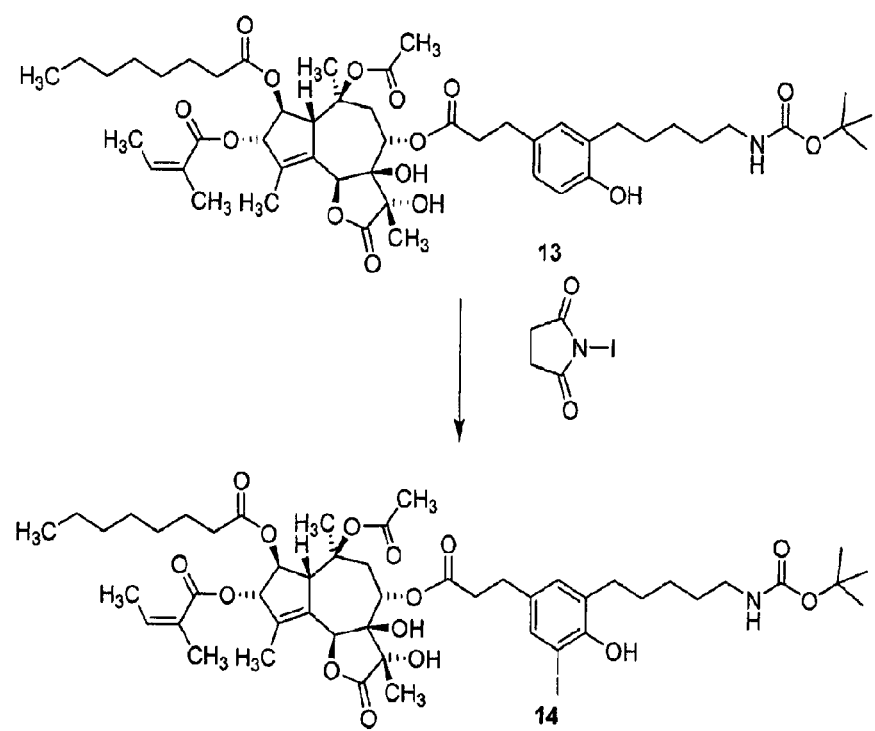

In the course of developing a PSMA-activated TG therapy, a prodrug that was readily hydrolyzed by PSMA and selectively toxic to PSMA-producing human prostate cancers in vitro and in vivo was identified. Tissue levels of the TG analog (12ADT-Asp) that is released from the peptide carrier by PSMA were analyzed. See, for example, FIG. 4A.

The characterization of 12ADT-Asp is described in detail below. This TG analog is even more lipophilic than TG due to substitution of the butanoyl side chain of TG with a 12 carbon aminododecanoyl side chain. While it might have been expected to see accumulation of this highly lipophilic 12ADT-Asp in tumor tissue due to PSMA activation, the magnitude of accumulation of the free drug compared to plasma was unexpected. See FIG. 4A. In additional studies, levels of prodrug and free drug were analyzed in two tissues (i.e., brain and kidney) known to express PSMA in the mouse, and one tissue, skeletal muscle, that did not. See FIGS. 4A and 4B. These studies documented much higher levels of 12ADT-Asp in tumor tissue on a % Injected Dose/gram tissue with Tumor/Kidney ratio of 15.4 and Tumor/Skeletal muscle of 20.5. These Tumor/Tissue ratios were more favorable than that previously reported in anti-PSMA antibody and labeled PSMA inhibitor studies.

Accordingly, in some embodiments, the presently disclosed subject matter provides a PSMA-activated imaging agent can be achieved by coupling a radiolabeled TG analog to a peptide carrier that is a substrate for prostate specific membrane antigen (PSMA). This substrate can be readily cleaved by PSMA within prostate cancer sites resulting in the release of a radiolabeled cytotoxin (e.g., thapsigargin or a thapsigargin analog) that can selectively accumulate in prostate cancer tissue over time. Such accumulation allows for imaging of the PSMA-positive prostate cancers. In addition, if the radiolabeled TG analog maintains its ability to elevate intracellular calcium and activated apoptosis, prostate tumor selective imaging and targeted delivery of a potent cytotoxin in a single molecular species can be achieved, while at the same time minimizing toxicity to normal tissues.

Using a combination of biochemical, cell biology and molecular approaches, the mechanism of action of TG's cytotoxicity has been defined. In summary, this cytotoxicity is due to TG's dose response ability to elevate intracellular calcium to sufficient levels to activate apoptosis in all of the rodent and human androgen independent prostate cancer cell lines without requiring the cells to be proliferating. This perturbation in intracellular calcium is initiated by the passive entrance of TG into the cell due to its high lipophilicity. Once inside the cell, TG diffuses within the intracellular membranes until it interacts with the ATP-dependent Ca2+ pump in the endoplasmic reticulum, termed the SERCA pump. At low nanomolar concentrations TG binds to the transmembrane portion of the SERCA protein inhibiting its ATP hydrolysis dependent pumping ability needed to sequester Ca2+ in the internal cristae of the ER. Once the SERCA pump is inhibited, there is a dissipation of the sequestered Ca2+ pool due to its passive leakage out of the ER. This depletion of the Ca2+ pool of the ER generates a signal that causes changes in the plasma membrane permeability to Ca2+ allowing an influx of the 1-3 mM extracellular free Ca2+. This "capacitance" entrance of extracellular Ca2+ causes a sustained elevation in intracellular calcium eventually to μmolar levels resulting in activation of apoptotic pathways in the nucleus, ER and mitochondria.

While TG is more effective than most antiproliferative chemotherapeutic agents against rapidly proliferating cells in culture, what makes this agent interesting is its equally potent ability to kill non-proliferating cells. This proliferation independent induction of cell death is of particular importance for agents targeting prostate cancer cells. In previous studies, it has been demonstrated that prostate cancer cells, including metastatic androgen independent prostate cancer cells, have a remarkable low rate of cell proliferation (i.e., <5% cells proliferating/day). In a more recent study, the growth fraction in 117 metastatic sites of prostate cancer obtained from 11 androgen ablation failing patients at "warm" autopsy was analyzed. In these metastatic sites the growth fraction was 7.1±0.8%. This low proliferative rate could explain the relative unresponsiveness of prostate cancer cells in humans to standard anti-proliferative chemotherapy, while highly proliferative androgen independent prostate cancer cell lines remain exquisitely sensitive to apoptosis induction in vitro.

Synthesis and Characterization of Iodide-Labeled Asp- or Glu-Containing TG Analogs The presently disclosed subject matter, in some embodiments, provides the synthesis and characterization of the cytotoxicity and stability of a series of iodide labeled Asp- or Glu-containing TG analogs; the synthesis of iodinated PSMA prodrugs and characterization of PSMA-selective activation and cytotoxicity to PSMA-producing prostate cancer cells in vitro; and the determination of the in vivo toxicity, pharmacokinetics and biodistribution of $^{125}$I labeled PSMA-activated prodrugs in non-tumor bearing mice and mice bearing PSMA-positive tumor human prostate cancer xenografts.

Iodinated and non-iodinated analogs can be evaluated for (1) stability of the analog in human plasma by LC-MS analysis; (2) degree of uptake by panel of human prostate cancer cells in vitro (androgen sensitive, PSMA positive LNCaP and CWR22R and androgen independent, PSMA negative PC-3 and DU145); (3) cytotoxicity to this prostate cancer cell line panel in MTT proliferation assays. Analogs that are stable in plasma and good cellular uptake can be radiolabeled with $^{125}$I and exposed to cell panel to evaluate for release of $^{125}$I label from analog by intracellular degradation. Analogs that would accumulate in prostate cancer cell lines and maintain iodine label for prolonged periods of time that could be used for imaging applications can be identified in this way. Analogs that readily accumulate, are stable to degradation, and loss of iodine label and maintain cytotoxicity to prostate cancer cells will be considered potential lead compounds.

Methods of Synthesis of Iodide-Labeled Asp- or Glu-Containing TG Analogs

One way to introduce radiolabeled iodine into drugs for whole-body imaging is to take advantage of a phenolic group present in the molecule. To accomplish iodination the so-called "iodogen method" can be used. This method has been used for labeling of monoclonal antibodies. Accordingly, to introduce an iodine label into the molecule, a phenolic group must be introduced into the structure of TG. To accomplish this, a series of modified Aspartyl or Glutamyl 12ADT analogs containing an iodinatable phenolic substituent at various positions directly within the 12 aminododecanoyl side chain can be generated (Class I analogs). A second series of modified Aspartyl or Glutamyl 12ADT analogs containing an iodinatable phenolic side chain coupled to an amine group at various positions within the 12 aminododecanoyl side chain also can be generated (Class II analogs). These analogs can be synthesized and then iodinated using a standard chloramine-T method. After Boc protection of the amino group and TBDS protection of the phenol group, the linker can be attached to debutanoylthapsigargin according to established procedures. The position of the phenolic group should be varied to produce optimal linker for PSMA hydrolysis. Only 4-hydroxypropanoic acid is readily commercially available. Consequently a change of the location of the phenolic group in the linker needs development of a synthetic method for preparing the starting ω-(4-benzoxyphenyl)alkanoic acid. A general procedure for preparing such acids is provided in FIG. 2C.

A prolongation of the chain between the aromatic ring and the carboxylic acid can be followed by a reduction of the length of the chain between the amino group and the aromatic ring keeping the sum m+n=8, as shown in the following structure:

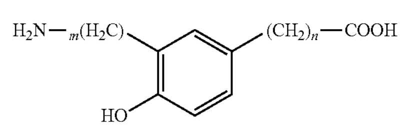

The flexibility of the presently disclosed protocol, however, also enables changes in the lengths of the different chains.

The inclusion of the phenolic ring in the 8-O-acyl group could generate significant alteration in ability of TG to bind to SERCA target. Therefore, an alternative strategy to the method disclosed immediately hereinabove for introducing a phenolic group into the molecule is provided in FIG. 2D. In FIG. 2D, the methyl ester is cleaved to give the carboxylic acid, which is coupled to DBTG according to the method shown in FIG. 2A. Finally the tert-butoxygroup is cleaved with acid to give the phenolic thapsigargin analog.

Figure 2E:
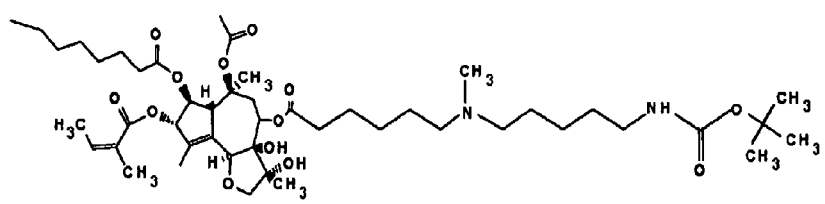
FIG. 2E is a chemical structure of compound 16, which exhibitsSERCA inhibition that was equipotent to TG and an IC50 against PSMA+LNCaP cells of 100 nM.
Figure 3:
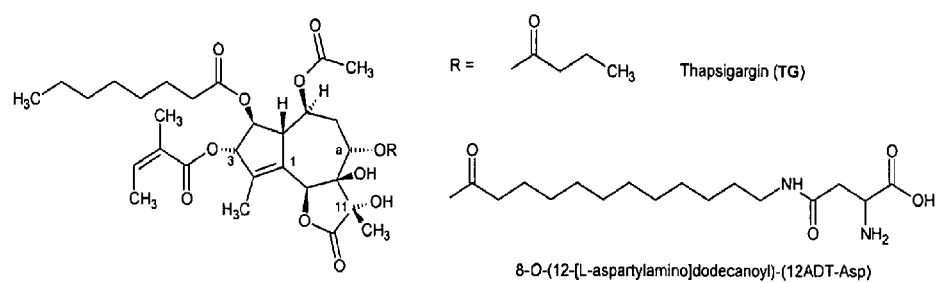
FIG. 3 is the chemical structure of 12ADT-Asp.

This strategy is based on preliminary data with compound 16 demonstrating SERCA inhibition that was equipotent to TG and an IC50 against PSMA+LNCaP cells of 100 nM. FIG. 2E.

Iodination Procedure

Iodination is performed using the so-called "Iodogen method." Briefly, the TG analog in PBS is added to a vial coated with 100 μg Iodogen. [$^{195}$I]NaI 91-5 mCi; MP Biomedicals, Costa Mesa, Calif.) is then added to the vial and the reaction proceeds at room temperature for 15 minutes. The solution is then withdrawn and purified on preparative HPLC in line with a radioactive flow detector. The product is collected and concentrated under vacuum.

Prodrugs can be synthesized by coupling non-iodinated TG analogs, as disclosed hereinabove, to PSMA substrates Asp*Glu*Glu*Glu*Glu (SEQ ID NO:57) or Glu*Glu*Glu*Glu*Glu (SEQ ID NO:62). Peptides can be synthesized by solid phase coupling of appropriately tert-butoxy blocked Asp or Glu amino acids using standard Fmoc coupling protocols on a PS-3 solid phase synthesizer. Such peptide syntheses are known in the art. Primary amine-containing TG analogs can be coupled to the PSMA peptides and purified using HOBt, DIC activation methods known in the art. Tert-butoxy protecting groups can be removed from final product by TFA. Prodrugs can be iodinated by the Iodogen method.

PSMA hydrolysis can be determined by incubation of prodrugs with purified enzymatically active His-tagged PSMA. Sequential hydrolysis of prodrugs can be determined by HPLC analysis. Intracellular uptake of PSMA-liberated TG analogs can be assayed in acetonitrile extracted prostate cancer cell homogenates.

Methods of Synthesis of Tritium Labeled TG Analogs

The phenolic thapsigargin analog can be dissolved in an appropriate solvent, such as $CH_3O^3H$, or another suitable solvent, followed by addition of an acid, such as $CF_3COO^3H$. After a period of time, tritium will substitute the ortho $^1H$ with $^3H$.

Animal Studies

Iodinated prodrugs that are hydrolyzed by PSMA and demonstrate selective uptake and cytotoxicity to PSMA-positive cell lines can be selected as "leads" for further in vivo analysis. Iodinated prodrugs that are hydrolyzed by PSMA and demonstrate selective uptake by PSMA-producing prostate cancer cells in vitro, but are not cytotoxic, can be selected as back-up compounds and/or can be used for imaging. Sufficient quantities of these prodrugs can be synthesized to complete in vivo studies. These prodrugs can be labeled with $^{125}$I. Initial studies can be carried out to determine the toxicity of a single intravenous injection of prodrug and establish maximally tolerated dose (MTD) for further studies. Non-tumor bearing nude mice can be given a single injection at the MTD. Animals (e.g., n=3/group) can be sacrificed at varying time points and plasma and tissues (i.e., liver, spleen, kidney, skeletal muscle, brain, heart, and/or lungs) can be harvested.

Subsequently, mice PSMA-positive Luciferase tagged LNCaP xenografts inoculated subcutaneously, orthotopically into the prostate and intratibially can be injected with $^{125}$I-labeled prodrug over a range of concentrations (MTD and ⅓ log reductions of MTD). Mice can be imaged at defined intervals (1, 2, 4 and 6 days post injection) using an X-SPECT small animal scanner (Gamma Medica, Inc, Northridge, Calif.) using either single-head, high resolution (1-3 mm) parallel hole or pinhole collimator. Images can be obtained according to standard protocols. Following these images, animals can be injected with luciferin and imaged using bioluminescent detector (Xenogen) to evaluate sensitivity of detection of labeled TG analog in tumor tissue compared to previously characterized luminescence approach. Finally, after these imaging modalities are complete, tumor, plasma and normal tissue can be harvested, homogenized and extracted in acetonitrile. Extracts can be evaluated for levels of PSMA-cleavage products to assess extent of PSMA-hydrolysis in tumor tissue and non-specific non-PSMA hydrolysis in normal tissue.

As a final step, animals with PSMA-positive CWR22H tumors implanted SQ, orthotopically and intratibially can receive, for example, five daily intravenous injections of the lead non-labeled iodinated prodrug and antitumor efficacy evaluated by serial measurement of tumor volumes over time.

Luciferase tagged LNCaP cells have been previously generated using methods known in the art. Tissue levels of total $^{125}$I label can be determined by placing tissue homogenates in gamma counter (Beckman). Mice can be imaged as described hereinabove according to published methods. Orthotopic and intratibial inoculations will be performed using sterile technique on anesthetized mice (ketamine/xylazine) according to established procedures.

In Vitro Cytotoxicity Assays

In vitro cytotoxicity assays can be performed by exposing prostate cancer cell lines to increasing doses of iodinated and non-iodinated analog for 3, 5, and 7 days and then assessing cell growth using 96-well MTT-based proliferation assay (Promega Corporation, Madison, Wis.).

To assess cellular uptake and stability of iodinated analogs, compounds can be incubated with prostate cancer cells or in human and mouse plasma for 24 hrs then extracted with 100% acetonitrile to precipitate proteins. Extracts of plasma and cells can then be evaluated by LC-MS analysis (PE Sciex). Degradation of the compound over time can be analyzed by comparing the extract to similarly extracted plasma spiked standards with internal standard (S-12ADT).

To assess release of $^{125}$I, labeled compounds can be exposed to prostate cancer cell lines at $IC_{50}$ doses for 24 hrs. Cells can be washed with Hanks Balanced Salts Solution×2 and then fresh media added. After 24 hrs, media will be collected and analyzed for $^{125}$I levels using gamma counter (Beckman).

TERMINOLOGY

Treatment, Therapeutics, Diseases and Conditions

In certain aspects of the invention, the terms "treat" or "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (e.g., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented. The terms "treating", "treat", or "treatment" embrace both preventative, e.g., prophylactic, and palliative treatment.

In other aspects of the invention, the phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (e.g., slow to some extent and preferably stop) cancer cell infiltration into peripheral organs; inhibit (e.g., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic.

In particular aspects of the invention, the terms "cancer" and "cancerous" refer to or describe the physiological condition in mammals that is typically characterized by unregulated cell growth, (e.g., neoplastic growth). A "tumor" comprises one or more cancerous cells. Examples of cancer include, but are not limited to, carcinoma, lymphoma, blastoma, sarcoma, and leukemia or lymphoid malignancies. More particular examples of such cancers include prostate, breast, colon, lung, brain, kidney, and bladder cancer.

As used herein, the term "subject" refers to any animal (e.g., a mammal), including, but not limited to, humans, non-human primates, rodents, and the like (e.g., which is to be the recipient of a particular treatment, or from whom cancer stem cells are harvested). Typically, the terms "subject" and "patient" are used interchangeably, unless indicated otherwise herein.

As used herein, the term "subject is suspected of having cancer" refers to a subject that presents one or more signs or symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received a preliminary diagnosis (e.g., a CT scan showing a mass) but for whom a confirmatory test (e.g., biopsy and/or histology) has not been done or for whom the stage of cancer is not known. The term further includes people who once had cancer (e.g., an individual in remission). A "subject suspected of having cancer" is sometimes diagnosed with cancer and is sometimes found to not have cancer.

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention. A "preliminary diagnosis" is one based only on visual (e.g., CT scan or the presence of a lump) and antigen tests.

As used herein, the term "subject at risk for cancer" refers to a subject with one or more risk factors for developing a specific cancer. Risk factors include, but are not limited to, gender, age, genetic predisposition, environmental expose, and previous incidents of cancer, preexisting non-cancer diseases, and lifestyle. As used herein, the term "cancer cells" refers to individual cells of a cancer. Such cells may include, for example, cells that express prostate specific membrane antigen (PSMA).

As used herein, the term "effective amount" refers to the amount of a composition sufficient to effect beneficial or desired results. An effective amount can be administered in one or more administrations, applications or dosages and is not intended to be limited to a particular formulation or administration route.

As used herein, the term "administration" refers to the act of giving a drug, prodrug, or other agent, or therapeutic treatment (e.g., compositions of the present invention) to a subject (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), oral mucosa (buccal), ear, by injection (e.g., intravenously, subcutaneously, intratumorally, intraperitoneally, etc.) and the like.

As used herein, the term "co-administration" refers to the administration of at least two agent(s) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, coadministration is especially desirable in embodiments where the co-administration of the agents or therapies lowers the requisite dosage of a potentially harmful (e.g., toxic) agent(s). "Amino acid sequence" and terms, such as "polypeptide" or "protein," are not meant to limit the amino acid sequence to the complete, native amino acid sequence associated with the recited protein molecule.

Pharmaceutical Compositions

In some embodiments, the presently disclosed subject matter provides a pharmaceutical composition comprising a therapeutically effective amount of the presently disclosed compounds. The presently disclosed compounds and prodrugs thereof are referred to herein as "active compounds." Pharmaceutical compositions comprising the aforementioned active compounds also are provided herein. These pharmaceutical compositions comprise the presently disclosed active compounds in a pharmaceutically acceptable carrier. The term "pharmaceutically acceptable" with respect to a component, such as a salt, carrier, excipient or diluent of a composition according to the presently disclosed subject matter refers to a component that is compatible with the other ingredients of the composition in that it can be combined with the presently disclosed compounds without eliminating the therapeutic efficacy of the compounds and is suitable for use with subjects as provided herein without undue adverse side effects (including, but not limited to, toxicity, irritation, and allergic response) to the subject to which the particular compound is administered. Examples of pharmaceutically acceptable components include, without limitation, any of the standard pharmaceutical carriers, such as phosphate buffered saline solutions, water, emulsions, such as oil/water emulsion, microemulsions, and various types of wetting agents.

Pharmaceutical formulations can be prepared for oral, intravenous, or aerosol administration as discussed in greater detail herein below. Also, the presently disclosed subject matter provides such active compounds that have been lyophilized and that can be reconstituted to form pharmaceutically acceptable formulations for administration, as by intravenous or intramuscular injection.

Useful injectable compositions include sterile suspensions, solutions or emulsions of the active compound(s) in aqueous or oily vehicles. The compositions also can contain formulating agents, such as suspending, stabilizing and/or dispersing agent. The compositions suitable for injection can be presented in unit dosage form, e.g., in ampules or in multidose containers, and can contain added preservatives. Alternatively, an injectable composition can be provided in powder form for reconstitution with a suitable vehicle, including, but not limited to, sterile water, buffer, dextrose solution, and the like, before use. To this end, the active compound(s) can be dried by any art-known technique, such as lyophilization, and reconstituted prior to use.

For oral administration, the pharmaceutical compositions can take the form of, for example, lozenges, tablets or capsules prepared by conventional means with pharmaceutically acceptable excipients, such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art with, for example, sugars or enteric coatings.

Liquid preparations for oral administration can take the form of, for example, elixirs, solutions, syrups or suspensions, or they can be presented as a dry product for constitution with water or other suitable vehicle before use. Such liquid preparations can be prepared by conventional means with pharmaceutically acceptable additives, such as suspending agents (e.g., sorbitol syrup, cellulose derivatives or hydrogenated edible fats); emulsifying agents (e.g., lecithin or acacia); non aqueous vehicles (e.g., almond oil, oily esters, ethyl alcohol or fractionated vegetable oils); and preservatives (e.g., methyl or propyl p-hydroxybenzoates or sorbic acid). The preparations also can contain buffer salts, preservatives, flavoring, coloring and sweetening agents as appropriate. Preparations for oral administration can be suitably formulated to give controlled release of the active compound or prodrug, as is well known.

For prolonged delivery, the active compound(s) or prodrug(s) can be formulated as a depot preparation for administration by implantation or intramuscular injection. The active ingredient can be formulated with suitable polymeric or hydrophobic materials (e.g., as an emulsion in an acceptable oil) or ion exchange resins, or as sparingly soluble derivatives, e.g., as a sparingly soluble salt.

Alternatively, transdermal delivery systems manufactured as an adhesive disc or patch which slowly releases the active compound(s) for percutaneous absorption can be used. To this end, permeation enhancers can be used to facilitate transdermal penetration of the active compound(s) and compositions. Suitable transdermal patches are described in for example, U.S. Pat. No. 5,407,713; U.S. Pat. No. 5,352,456; U.S. Pat. No. 5,332,213; U.S. Pat. No. 5,336,168; U.S. Pat. No. 5,290,561; U.S. Pat. No. 5,254,346; U.S. Pat. No. 5,164,189; U.S. Pat. No. 5,163,899; U.S. Pat. No. 5,088,977; U.S. Pat. No. 5,087,240; U.S. Pat. No. 5,008,110; and U.S. Pat. No. 4,921,475, each of which is incorporated herein by reference in its entirety.

In addition to compounds of the present invention or their salts or prodrugs, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain anti-microbial preservatives. Useful anti-microbial preservatives include methylparaben, propylparaben, and benzyl alcohol. The anti-microbial preservative is typically employed when the formulation is placed in a vial designed for multi-dose use.

The pharmaceutical formulations described herein can be lyophilized using techniques well known in the art. In such embodiments, the compound or salt is provided in the form of a lyophilizate, which is capable of being reconstituted with a suitable pharmaceutically acceptable carrier to form a liquid formulation suitable for injection thereof into a subject.

In yet another aspect of the subject matter described herein, there is provided a stable, sterile formulation comprising the presently disclosed compositions. The pharmaceutical compositions can, if desired, be presented in a pack or dispenser device (individually or collectively referred to as "a kit"), which can contain one or more unit dosage forms containing the active compound(s) and compositions. The kit can, for example, comprise metal or plastic foil, such as a blister pack. The kit can be accompanied by instructions for administration.

Peptides

In particular aspects of the invention "peptide" or "polypeptide" is meant any chain of amino acids, regardless of length or post-translational modification (e.g., glycosylation or phosphorylation). As written herein, amino acid sequences are presented according to the standard convention, namely that the amino-terminus of the peptide is on the left, and the carboxy terminus on the right. A "detectable label" refers to a reporter molecule or enzyme that is capable of generating a measurable signal and is covalently or non-covalently joined to a polynucleotide or polypeptide.

Prodrugs

As used herein the term "prodrug" refers to a pharmacologically inactive derivative of a parent "drug" molecule that requires biotransformation (e.g., either spontaneous or enzymatic) within the target physiological system to release, or to convert (e.g., enzymatically, mechanically, electromagnetically, etc.) the "prodrug" into the active "drug." "Prodrugs" are designed to overcome problems associated with stability, toxicity, lack of specificity, or limited bioavailability. Exemplary "prodrugs" comprise an active "drug" molecule itself and a chemical masking group (e.g., a group that reversibly suppresses the activity of the "drug"). Some preferred "prodrugs" are variations or derivatives of compounds that have groups cleavable under metabolic conditions. Exemplary "prodrugs" become pharmaceutically active in vivo or in vitro when they undergo solvolysis under physiological conditions or undergo enzymatic degradation or other biochemical transformation (e.g., phosphorylation, hydrogenation, dehydrogenation, glycosylation, etc.). Prodrugs often offer advantages of solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, Calif. (1992)). Exemplary prodrugs of the invention comprise a PSMA specific peptide and an anticancer agent.

Chemical Terminology

While the following terms in relation to compounds found throughout this application are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

A named "R" or group will generally have the structure that is recognized in the art as corresponding to a group having that name, unless specified otherwise herein. For the purposes of illustration, certain representative "R" groups as set forth above are defined below.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

A structure represented generally by the formula:

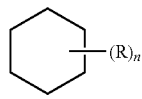

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

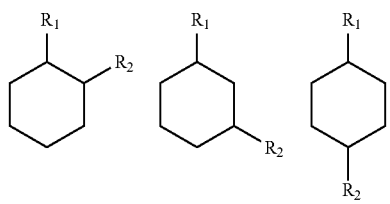

and the like.

The terms "halo", "halide", or "halogen" as used herein refer to fluoro, chloro, bromo, and iodo groups.

The term "nitro" refers to the $-NO_2$ group.

Throughout the specification and claims, a given chemical formula or name shall encompass all tautomers, congeners, and optical- and stereoisomers, as well as racemic mixtures where such isomers and mixtures exist. Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

The invention will be further described in the following examples, which do not limit the scope of the invention described in the claims.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

The presently disclosed subject matter demonstrates that a PSMA-Activated Imaging Agent can be achieved by radiolabeling a TG analog that can be converted to an inactive prodrug by coupling to a peptide carrier that is a substrate for Prostate Specific Membrane Antigen (PSMA). This substrate can be cleaved by PSMA within prostate cancer sites resulting in the release of a radiolabeled cytotoxin (TG analog) that would selectively accumulate in prostate cancer tissue over times. This would then allow PSMA positive prostate cancers to be imaged.

Example 1

Synthesis of TG analogs

Schemes for the synthesis of compounds 3-14 are provided in FIGS. 5A-5E.

Compound 1 (5 g, 24 mmol) (Bowden and Adkins, 1940) was drop wise added to a solution of compound 2 (7.1 g, 26.7 mmol) (Fujii et al., 1971) in $CH_2Cl_2$ (20 mL). After stirring at room temperature under $N_2$ for 15 min. $AlCl_3$ (9.9 g, 75 mmol) was added portion wise over a period of 10 min. The reaction mixture, which turned to reddish to orange, was stirred at room temperature under $N_2$ for 2 h, and water (100 mL) was added. The mixture was adjusted to pH 7 with 5% aqueous $NaHCO_3$, and extracted three times with $CH_2Cl_2$ (100 mL). The organic phases were combined and concentrated. The residue was purified by flash chromatography using EtOAc/toluene (1:9) as an eluent to give 3 (5 g, 66.7%). $^1$H NMR (300 MHz, $CDCl_3$): δ 7.84 (m, 2H, H3",6"), 7.70 (m, 2H, H4",5"), 7.48 (d, J2.4 Hz, H5), 7.27 (dd, J8.4, 2.4 Hz, H9), 6.86 (d, J 8.4 Hz, H8), 4.10 (q, J 7.5 Hz, 2H, $CH_2O$), 3.86 (s, 3H, $CH_3O$), 3.72 (t, J 6.6 Hz, 2H, H5"), 3.01 (t, J 6.9 Hz, 2H, H2'), 2.90 (t, J 8.1 Hz, 2H, H3), 2.59 (t, J 8.5 Hz, 2H, H2), 1.74 (m, 4H, H3',4'), 1.24 (t, J7.5 Hz, 3H, $CH_3CH_2$). $^{13}$C NMR (75 MHz, $CDCl_3$): δ 202.4 (C1') 173.0 (C1), 168.6 (C1",8"), 157.2 (C7), 134.1 (C4",5"), 133.4 (C9), 133.0 (C4), 132.3 (C2",7"), 130.1 (C5), 128.5 (C6), 123.4 (C3",6"), 111.9 (C8), 60.7 ($CH_2O$), 55.8 ($CH_3O$), 43.4 (C2), 38.1 (C2'), 36.2 (C5'), 30.1 (C3), 28.5 (C4'), 21.8 (C3'), 14.5 ($CH_2CH_3$).

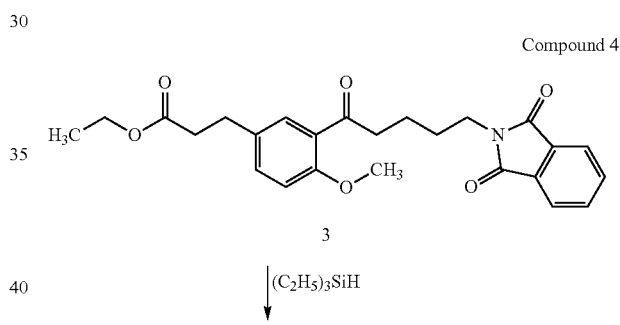

Compound 4

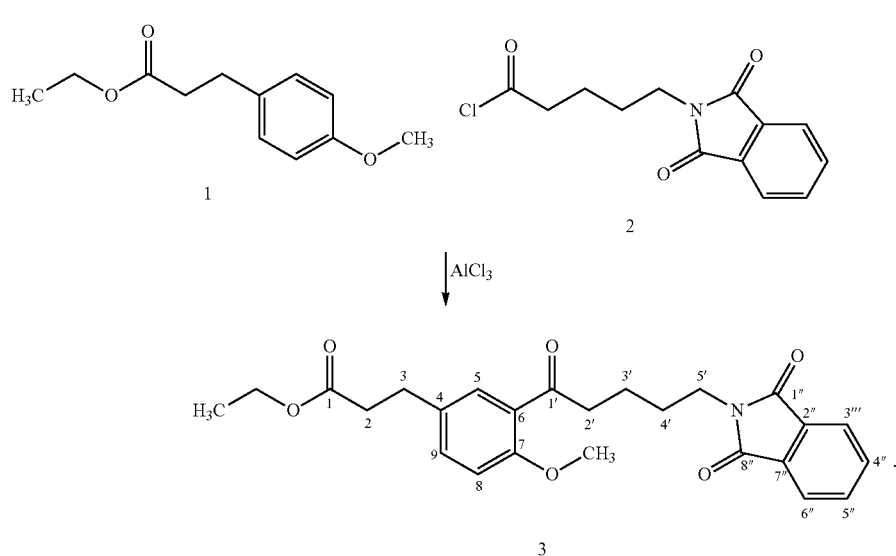

Compound 3

-continued

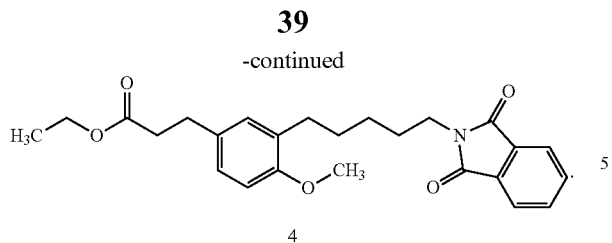
4

Triethylsilane (2.6 g, 5.9 mmol) was added to a solution of 3 (2.6 g, 5.9 mmol) in trifluoroactic acid (10 mL) and the solution was stirred for 3 h. The reaction mixture was concentrated and the residue was purified by flash chromatography on silica gel with toluene/ethyl acetate (1:9) as eluent to give 4 (2 g, 80%). $^1$H NMR (300 MHz, CDCl$_3$): δ 7.84 (m, 2H, H3",6"), 7.71 (m, 2H, H4",5"), 6.98 (dd, J 8.1, 1.8 Hz, H9), 6.95 (d, J 1.8 Hz, H5), 6.74 (d, J 8.1 Hz, H8), 4.13 (q, J 6.9 Hz, 2H, CH$_2$O), 3.78 (s, 3H, CH$_3$O), 3.71 (t, J 7.5 Hz, 2H, H5'), 2.86 (t, J 8.1 Hz, 2H, H3), 2.57 (two overlapping t, J 8.4 Hz, 2H, H2,1'), 1.72 (m, 2H, H2'), 1.60 (m, 2H, H4'), 1.39 (m, 2H, H3'), 1.24 (t, J 6.9 Hz, 3H, CH$_3$CH$_2$). $^{13}$C NMR (75 MHz, CDCl$_3$): δ 173.4 (C1), 168.7 (C1",8"), 156.1 (C7), 134.1 (C4",5"), 132.5 (C4), 132.4 (C2",8"), 130.1 (C5), 126.7 (C6), 126.7 (C9), 123.4 (C2",7"), 128.5 (C6), 123.4 (C3",6"), 110.5 (C8), 60.6 (CH$_2$O), 55.6 (CH$_3$O), 38.4 (C2), 36.7 (C5'), 30.5 (C4'), 30.4 (C1'), 29.9 (C3), 28.8 (C2'), 27.1 (C3'), 14.6 (CH$_2$CH$_3$).

Compound 5

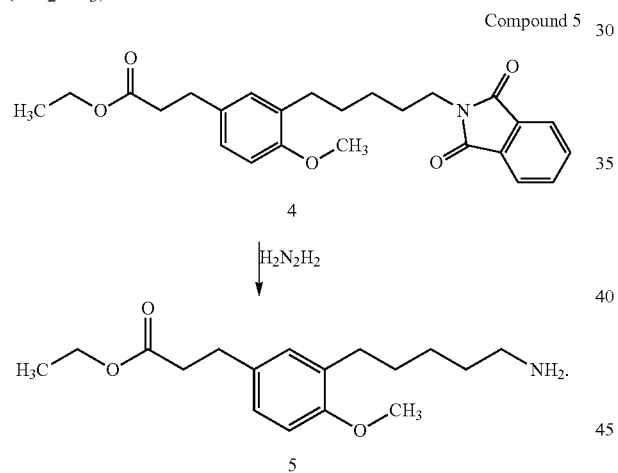

Hydrazine hydrate (120 mg, 2.4 mmol) was added to a stirred solution 4 (1 g, 2.4 mmol) in 15 mL of MeOH. After stirring for 3 h 15 mL of NH$_4$OH. were added, and the mixture was extracted three times with CH$_2$Cl$_2$ (20 mL). The organic phases were combined and concentrated to give the 5 (650 mg, 94%).

Compound 6

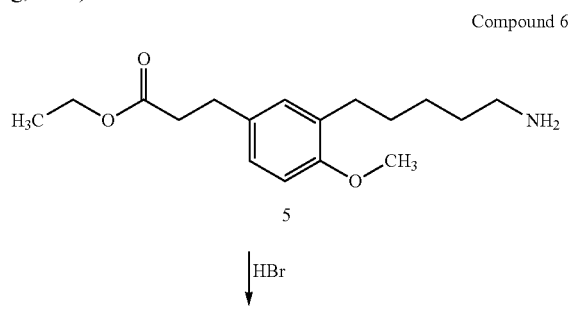

-continued

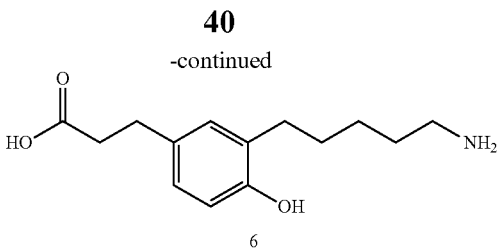
6

The crude compound 6 was dissolved in 10 mL of 48% aqueous HBr. The reaction mixture was heated to reflux for 4 h and added iced water (50 mL). The aqueous solution was washed twice with ether (50 mL) and the aqueous phase concentrated to give 6 (600 mg).

Compound 7

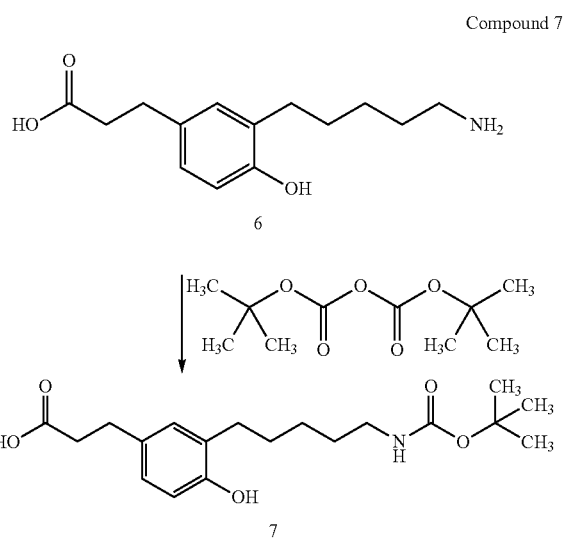
7

The crude 6 (600 mg, 2.4 mmol) was dissolved in acetone (7.5 mL) and water (2.5 mL) and to the solution was added added NaHCO$_3$ (900 mg) and Boc$_2$O (900 mg, 4.1 mmol). The reaction mixture was stirred for 2 h and concentrated in vacuo to half volume and the precipitate removed by filtration. The filtrate was concentrated in vacuo and the residue chromatographed on RP 18 to give 7 (500 mg, 51%) using methanol-water (5:1) added 1% of acetic acid as an eluent. $^1$H NMR (300 MHz, CD$_3$OD): δ 6.89 (d, J 1.8 Hz, H5), 6.85 (dd, J 8.1, 1.8 Hz, H9), 6.64 (d, J 8.1 Hz, H8), 3.00 (t, J 6.0 Hz, 2H, H5'), 2.77 (t, J 8.1 Hz, 2H, H3), 2.51 (t, J 6.0 Hz, 2H, H2) 2.47 (t, J 8 Hz, 2H, H1'), 1.50 (m, 2H, H2'), 1.47 (m, 2H, H4'), 1.33 (m, 2H, H3') 1.41 (s, 9H, CH$_3$). $^{13}$C NMR (75 MHz, CD$_3$OD): δ 177.9 (C1), 157.3 (CON), 153.1 (C7), 132.0 (C4), 129.7 (C5), 128.7 (C6), 126.2 (C9), 114.7 (C8), 78.7 (CO), 40.3 (C5'), 37.8 (C3), 31.0 (C1'), 30.2 (C2), 29.8 (C2'), 29.8 (C4'), 27.8 (CH$_3$), 26.7 (C3').

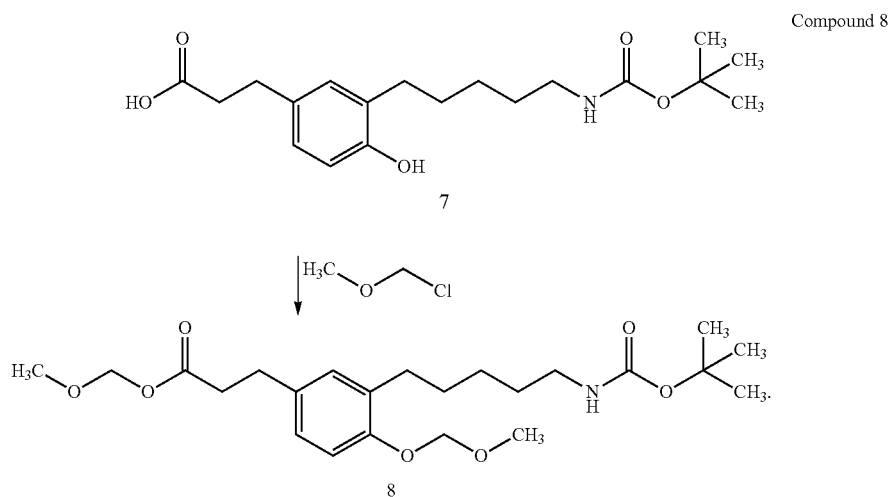

Compound 8

Chloromethyl methyl ether (230 mg, 2.9 mmol) and N,N-diisopropylethylamine (370 mg, 2.9 mmol) were added to a refluxed solution of 7 (500 mg, 1.7 mmol) in 20 mL of acetonitrile. After reflux for 30 min three additional protions of chloromethyl methyl ether (each times 230 mg) and N,N-diisopropylethylamine (each times 370 mg) followed by reflux for additional 30 min after each addition. After reflux for 30 min after addition of the fourth portions of reagents the mixture was cooled to room temperature and added water (30 mL) and a saturated aqueous solution of $NaHCO_3$ (20 mL). The reaction mixture was extracted three times with ether (20 mL). The extracts were concentrated in vacuo. The residue was purified by CC to give compound 8 (220 mg, 30%). $^1$H NMR (300 MHz, $CDCl_3$): δ 6.96 (s, 3H, H5,8,9), 5.20 and 5.15 (s, each 2H, $OCH_2O$), 3.47 and 3.41 (s, each 3H, $CH_3O$), 3.10 (m, 2H, H5'), 2.88 (t, J 8.1 Hz, 2H, H3), 2.63 (t, J 8.1 Hz, 2H, H2) 2.58 (t, J8 Hz, 2H, H1'), 1.58 (m, 2H, H2'), 1.47 (m, 2H, H4'), 1.35 (m, 2H, H3') 1.43 (s, 9H, $CCH_3$). $^{13}$C NMR (75 MHz, $CDCl_3$): δ 172.7 (C1), 155.8 (CON), 153.3 (C7), 133.1 (C4), 131.4 (C8), 129.8 (C9), 126.3 (C5), 113.8 (C8), 94.3 and 90.3 ($CH_2O$), 78.9 (CO), 57.6 and 56.0 ($CH_3O$), 40.6 (C5'), 36.2 (C1'), 30.3 (C3), 31 (C4'), 30.0 (C2'), 29.8 (C2), 28.5 ($CH_3$), 26.8 (C3').

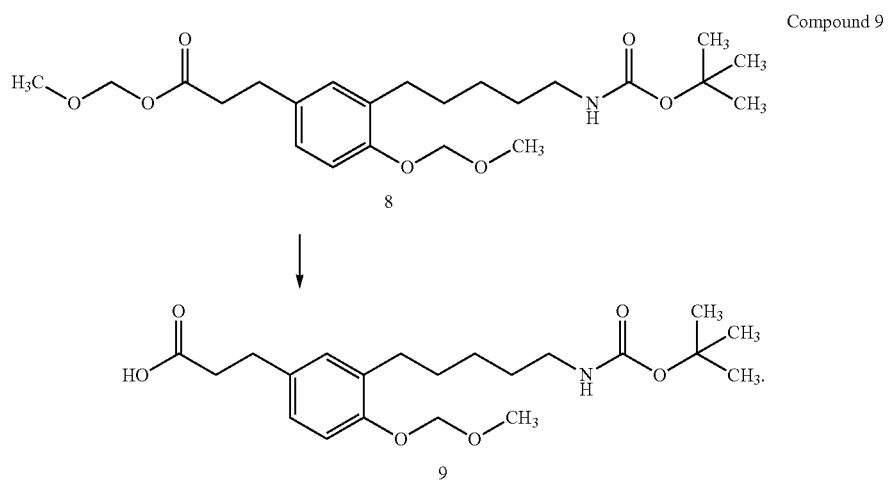

Compound 9

Lithium hydroxide hydrate (100 mg) was added to a solution of 8 (400 mg) in 10 mL of methanol-water (1:1). The mixture was stirred for 3 h at room temperature and concentrated in vacuo. The residue was dissolved in 10 mL of water and acidified with hydrochloric acid (6 M) to pH 2. The mixture was extracted three times with $CH_2Cl_2$ (20 mL). The combined organic phases were washed with brine, dried over $Na_2SO_4$, and concentrated in vacuo to give compound 11 (300 mg, 92%)

3H, H13), 1.32 (s, 3H, H14). Angeloate 6.10 (qq, J 6, 3 Hz, 1H, H3), 1.98 (dq, J6, 3 Hz, 3H, H4), 1.90 (q, J 3 Hz, 3H, Me2). Acetate 1.87 (s, 3H, Me). Octanoate 2.29 (m, 2H, H2), 1.56 (m, 2H, H3), 1.26 (m, 8H, H4-7), 0.86 (t, J 6 Hz, 3H, H8). Linker 6.95 (s, 3H, H5-9), 5.15 (s, 2H, $OCH_2O$), 3.46 (s, 3H, $CH_3O$), 3.09 (m, 2H, H5'), 2.84 (t, J 6 Hz, 2H, H3), 2.59 (t, J 8 Hz, 2H, H2) 2.56 (t, J 8 Hz, 2H, H1'), 1.60 (m, 2H, H2'), 1.47 (m, 2H, H4'), 1.35 (m, 2H, H3') 1.41 (s, 9H, $CCH_3$). $^{13}C$ NMR (75 MHz, $CDCl_3$): δ Guaianolide 176 (C12), 141.1 (C5), Compound 10 and 11

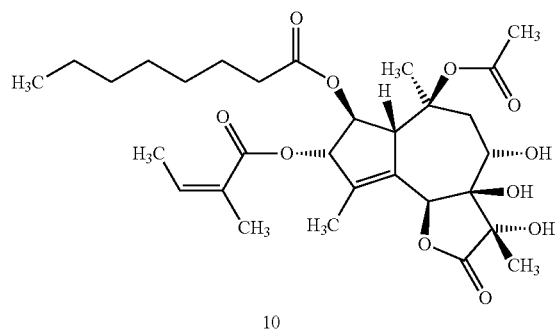

10

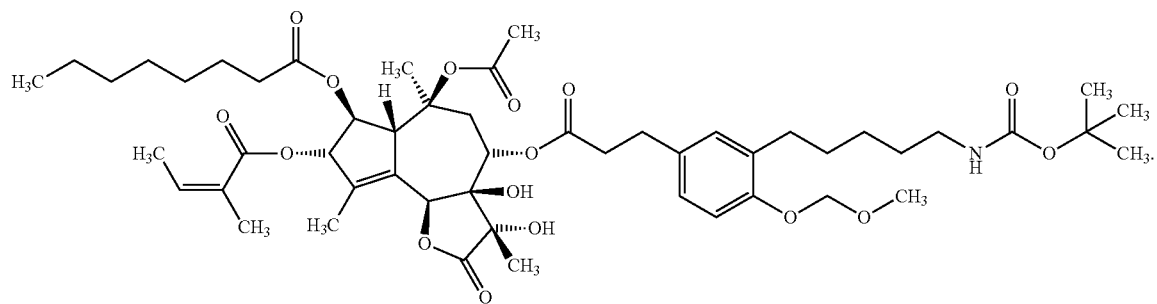

11

Dicyclohexylcarbodiimide (230 mg, 1.1 mmol) was added to a solution of 9 (400 mg 1.1 mmol), DBTg (10) (607 mg, 1.1 mmol), and DMAP (50 mg) in dry $CH_2Cl_2$ (5 mL). After stirring for 4 h at room temperature the reaction mixture was filtered and the filtrate was concentrated in vacuo. The residue was purified by Chromatography on RP18 using $CH_3OH$/$H_2O$ (4:1) added 0.1% AcOH as eluent to give compound 12 (650 mg, 55%). $^1H$ NMR (300 MHz, $CDCl_3$): δ Guaianolide 5.66 (s, 1H, H3), 5.64 (brs, 1H, H8), 5.62 (s, 1H, H6), 5.42 (t, J 3 Hz, 1H, H2), 4.32 (brs, 1H, H1), 2.90 (dd, J 15, 3 Hz, 1H, H9a), 2.20 (overlapped, H9b), 1.84 (brs, 3H, H15), 1.40 (s, 130.4 (C4), 84.3 (C10), 84.1 (C3), 79.4 (C11), 78.4 (C7), 77.3 (C2), 66.1 (C8), 57.7 (C1), 38.3 (C9), 22.7 (C14), 15.9 (C13), 13.0 (C15). Angeloate 166.9 (C1), 138.6 (C3), 126.3 (C2), 20.6 (Me2), 16.1 (C4). Acetate 170.1 (C1), 22.6 (C2). Octanoate 172.4 (C1), 34.3 (C2), 24.9 (C3), 30.1 (C4), 29.1 (C5), 31.7 (C6), 26.4 (C7), 14.1 (C8). Linker 171.5 (C1), 155.9 (CON), 153.3 (C7), 132.9 (C4), 131.1 (C6), 130.3 (C5), 127.3 (C9), 115 (C8), 94.3 ($CH_2O$), 77.7 (CO), 56.0 ($CH_3O$), 40.7 (C5'), 36.7 (C1'), 30.1 (C3), 29.9 (C2), 29.9 (C2'), 29.7 (3'), 28.5 ($CH_3$), 22.6 (C4'). HRMS m/z 980.4994, calc. for $C_{51}H_{75}NNaO_{16}^+$ 980.4978.

Compound 12
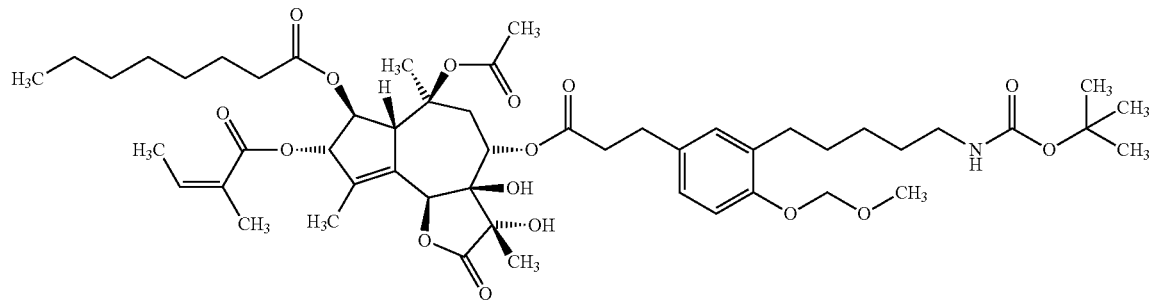
11
↓ CF₃COOH
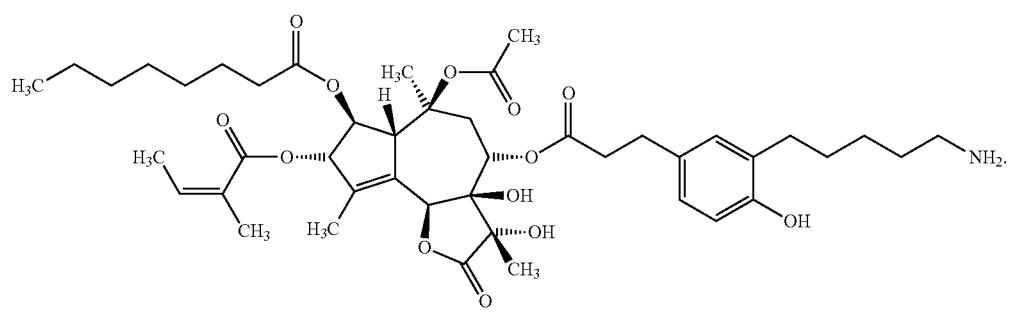
12
Trifluoroacetic acid (2 mL) was added to a solution of 11 (300 mg, 0.31 mmol) in dichloromethane (6 mL) and the mixture was stirred for 3 h. The solution was concentrated in vacuo to give 12. ¹H NMR (300 MHz, CDCl₃): δ Guaianolide 5.63 (s, 2H, H3,6), 5.58 (brs, 1H, H8), 5.43 (t, J3 Hz, 1H, H2), 4.19 (brs, 1H, H1), 2.90 (overlapped, H9a), 2.20 (overlapped, H9b), 1.75 (brs, 3H, H15), 1.37 (s, 3H, H13), 1.28 (s, 3H, H14). Angeloate 6.07 (brq, J 6 Hz, 1H, H3), 1.94 (dq, J6, 3 Hz, 3H, H4), 1.86 (q, J3 Hz, 3H, Me2). Acetate 1.84 (s, 3H, Me). Octanoate 2.31 (m, 2H, H2),
Compound 13
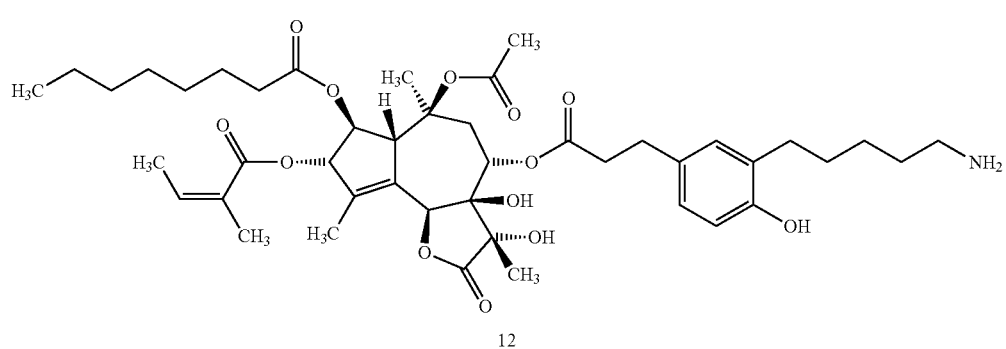
12
↓

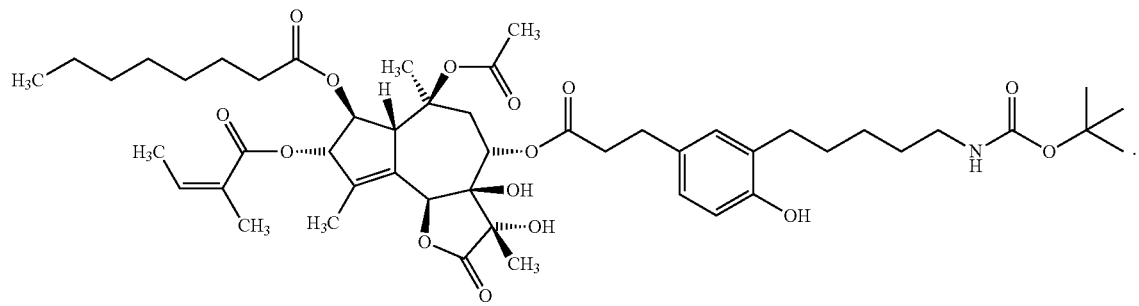

13

Di-tert-butyldicarbonate (50 mg, 0.2 mmol) and DMAP (50 mg) was added to a solution of 12 in dichloromethane (4 mL) and the mixture was stirred for 30 min. The residue after concentration was fractionated by CC over RP 18 using methanol-water (5:1) added 1% of glacial acetic acid as an eluent to give 12 (130 mg, 46%). $^1$H NMR (300 MHz, CDCl$_3$): δ Guaianolide 5.66 (s, 1H, H6), 5.63 (s, 2H, H3,8), 5.46 (t, J 3 Hz, 1H, H2), 4.23 (brs, 1H, H1), 2.90 (brd, J 12 Hz, H9a), 2.20 (overlapped, H9b), 1.82 (brs, 3H, H15), 1.42 (s, 3H, H13), 1.35 (s, 3H, H14). Angeloate 6.09 (brq, J 6.3 Hz, 1H, H3), 1.98 (brq, J 6.3 Hz, 3H, H4), 1.90 (brs, 3H, Me2). Acetate 1.88 (s, 3H, Me). Octanoate 2.27 (m, 2H, H2), 1.57 (m, 2H, H3), 1.25 (m, 8H, H4-7), 0.86 (t, J 6 Hz, 3H, H8). Linker 6.87 (brs, 1H, H5), 6.81 (brd, J 8.1 Hz, 1H, H9), 6.68 (d, J 8.1 Hz, 1H, H8), 4.75 (brt, 1H, NH), 3.06 (m, 2H, H5'), 2.78 (brt, 2H, H3), 2.54 (m, 4H, H2,1'), 1.58 (m, 2H, H2'), 1.42 (m, 2H, H4'), 1.3 (m, 2H, H3'), 1.42 (s, 9H, CCH$_3$). $^{13}$C NMR (75 MHz, CDCl$_3$): δ Guaianolide 176.1 (C12), 140.9 (C5), 130.4 (C4), 84.7 (C3), 84.1 (C10), 79.5 (C11), 78.5 (C7), 78.3 (C2), 66.2 (C8), 57.7 (C1), 38.1 (C9), 22.5 (C14), 15.8 (C13), 12.9 (C15). Angeloate 167.1 (C1), 138.7 (C3), 126.3 (C2), 20.5 (Me2), 15.8 (C4). Acetate 170.8 (C1), 22.3 (C2). Octanoate 172.7 (C1), 34.2 (C2), 24.7 (C3), 29.8 (C4), 29.3 (C5), 31.6 (C6), 26.4 (C7), 14.1 (C8). Linker 172.2 (C1), 156.2 (CON), 152.4 (C7), 131.4 (C4), 130.1 (C6), 128.7 (C5), 127.9 (C9), 115.5 (C8), 77.8 (CO), 40.5 (C5'), 36.6 (C1'), 29.8 (C3), 28.9 (C2), 28.9 (C2'), 29.8 (3'), 28.4 (CH$_3$), 22.6 (C4'). HRMS m/z 936.4692, calc. for $C_{51}H_{75}NNaO_{16}^+$ 936.4716.

Compound 14

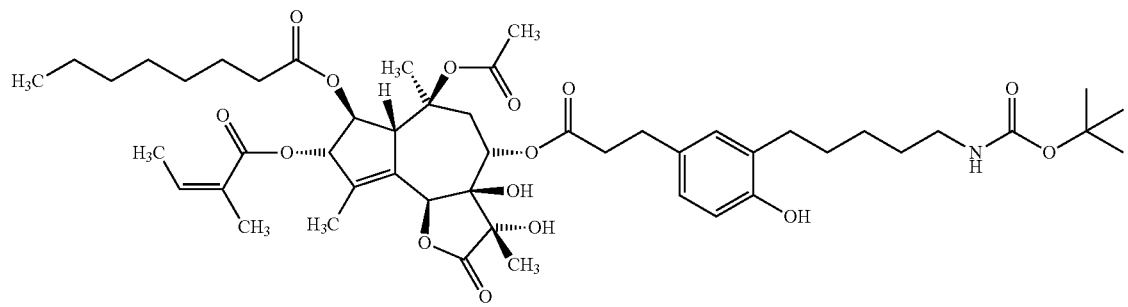

13

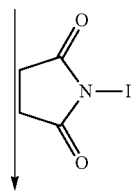

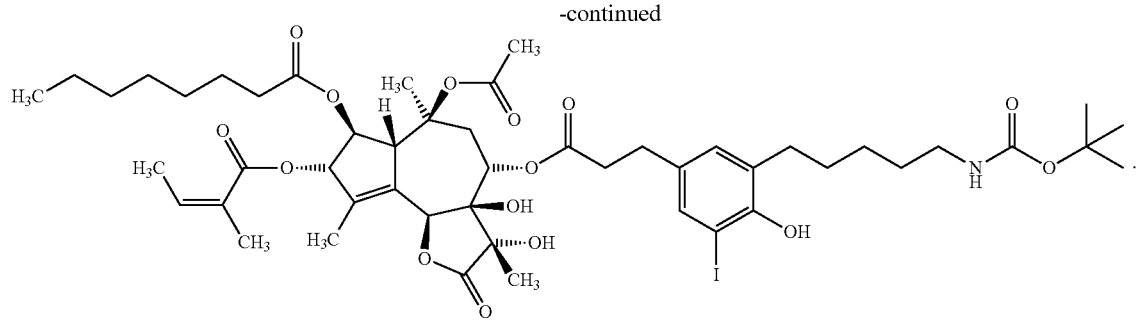

14

N-Iodosuccinimide (35 mg, 0.2 mmol) and p-toluenesulfonic acid (5 mg, 0.03 mmol) was added to a solution of 13 (70 mg, 0.1 mmol) in dry dichloromethane and the mixture was stirred for 1.5 h. A solution of aqueous sodium thiosulfate (10%, 10 mL) was added and the mixture stirred for additional 10 min. The aqueous phase was isolated and extracted twice with dichloromethane (10 mL). The combined organic phases were concentrated and the residue fractionated by CC over RP18 using methanol-water (5:1) added 1% of glacial acetic acid as an eluent to give 14 (56 mg, 70%). $^1$H NMR (300 MHz, CDCl$_3$): δ Guaianolide 5.67 (s, 2H, H6,3), 5.59 (s, 1H, H8), 5.46 (t, J3.3 Hz, 1H, H2), 4.16 (brs, 1H, H1), 2.85 (overlapped, H9a), 2.20 (overlapped, H9b), 1.84 (brs, 3H, H15), 1.42 (s, 3H, H13), 1.32 (s, 3H, H14). Angeloate 6.09 (qq, J6.3, 1.2 Hz, 1H, H3), 1.99 (brq, J6.3, 1.2 Hz, 3H, H4), 1.91 (q, J 1.2 Hz, 3H, Me2). Acetate 1.88 (s, 3H, Me). Octanoate 2.27 (m, 2H, H2), 1.57 (m, 2H, H3), 1.25 (m, 8H, H4-7), 0.86 (t, J6 Hz, 3H, H8). Linker 7.30 (d, J2.1 Hz, 1H, H5), 6.89 (brs, 1H, H9), 4.61 (brt, 1H, NH), 3.06 (m, 2H, H5'), 2.77 (brt, 2H, H3), 2.63 (m, 2H, H1'), 2.53 (t, J 7.2 Hz, 2H, H2), 1.58 (m, 2H, H2'), 1.42 (m, 2H, H4'), 1.26 (m, 2H, H3'), 1.42 (s, 9H, CCH$_3$). $^{13}$C NMR (75 MHz, CDCl$_3$): δ Guaianolide 175.5 (C12), 141.3 (C5), 130.4 (C4), 84.4 (C3), 84.1 (C10), 79.6 (C11), 78.7 (C7), 78.4 (C2), 77.2 (C6), 66.2 (C8), 57.9 (C1), 38.3 (C9), 22.4 (C14), 15.9 (C13), 13.0 (C15). Angeloate 167.0 (C1), 138.7 (C3), 127.3 (C2), 20.6 (Me2), 16.2 (C4). Acetate 170.4 (C1), 22.6 (C2). Octanoate 172.5 (C1), 34.3 (C2), 24.8 (C3), 29.8 (C4), 29.4 (C5), 31.7 (C6), 26.2 (C7), 14.1 (C8). Linker 171.6 (C1), 156.1 (CON), 151.1 (C7), 135.1 (C9), 131.4 (C6), 129.1 (C5), 84.8 (C8), 77.6 (CO), 40.5 (C5'), 36.5 (C1'), 30.1 (C3), 29.1 (C2), 29.0 (C2'), 30.5 (3'), 28.4 (CH$_3$), 22.6 (C4'). HRMS m/z 1062.3698, calc. for C$_{49}$H$_{70}$INNaO$_{15}^+$.

Figure 6:
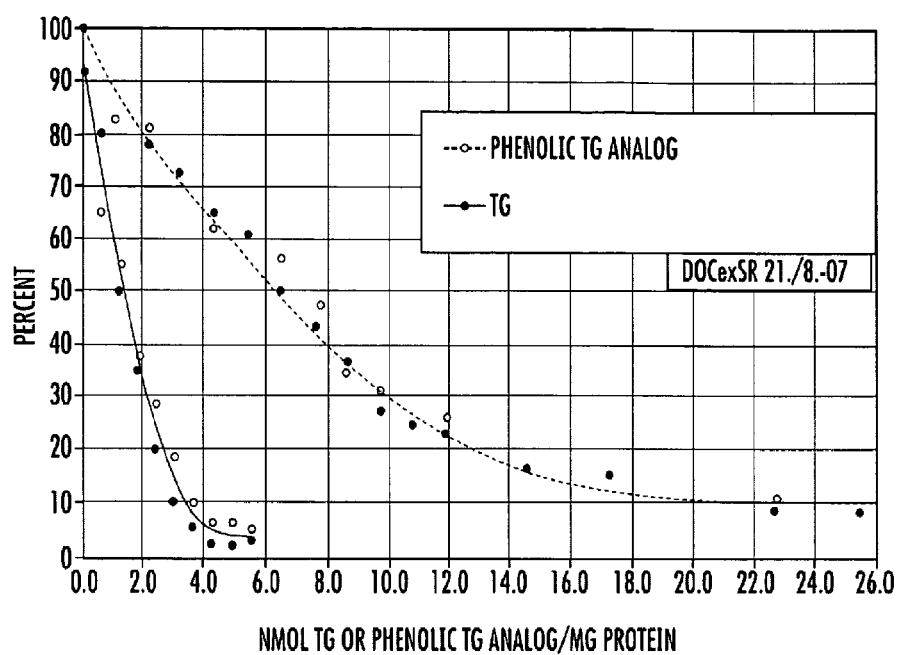
FIG. 6. Microsomal assay comparing inhibition of SERCA pump by compound 14 and TG over a range of concentrations.
Figure 7A:
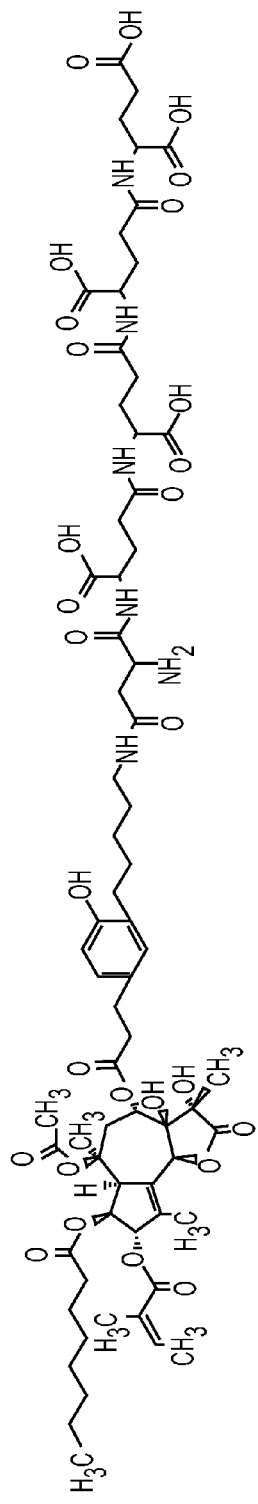
FIGS. 7A and 7B show the PSMA prodrug and free drug, respectively, for JHD-9783.
Figure 7B:
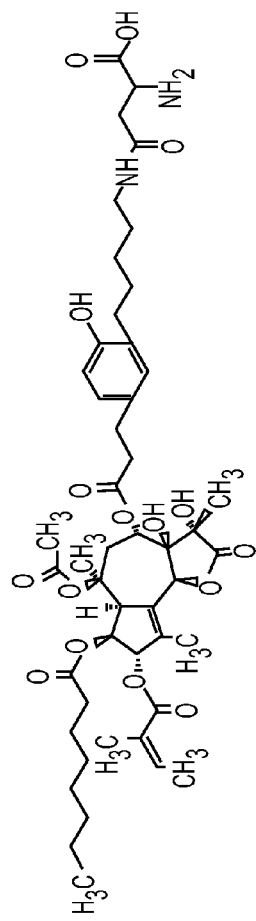
Figure 7C:
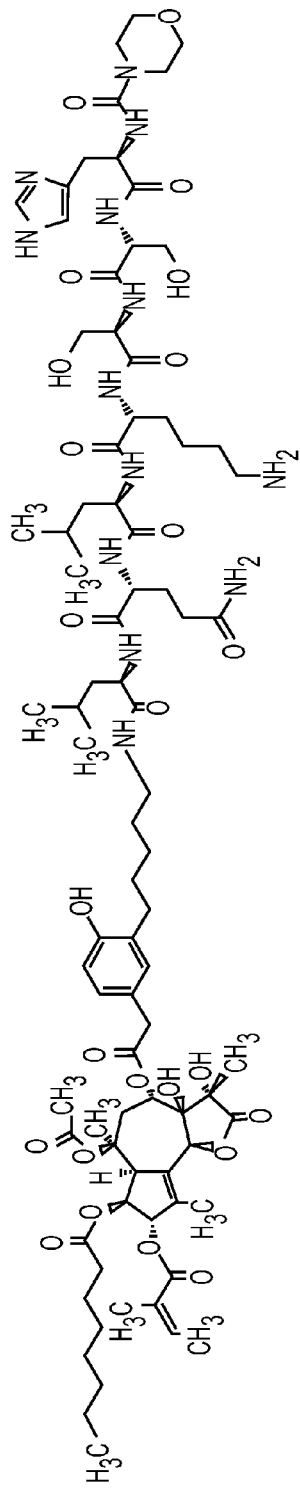
FIGS. 7C and 7D show the PSMA prodrug and free drug, respectively, for JHD-9784.
Figure 7D:
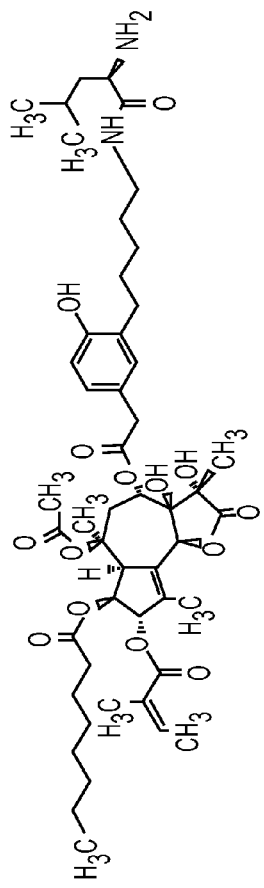

All materials were purified by column chromatography with structure confirmed by NMR analysis and mass spectroscopy. The purified phenolic TG analog 14 was then tested in a previously described microsomal assay system to assess inhibition of the SERCA pump compared to TG, FIG. 6. In this assay, compound 14 was approximately 4-fold less potent than TG but still maintained potent ability to inhibit the SERCA pump at nanomolar concentrations.

Example 2

Development of PSMA-Activated TG Prodrugs

Contrast enhanced TRUS, multimodality 3T MRI, MRSpectroscopy and nuclear bone scans are the most advanced imaging modalities used in contemporary urological practice for the diagnosis and staging of prostate cancer. All of these imaging modalities may be considered prostate imaging modalities, but lack the prostate cancer specific imaging modalities. With an increasing number of patients with minimal prostate cancer and opting for either focal treatment or active surveillance, the need for accurate, cancer specific imaging tools for diagnosis, treatment monitoring and follow-up is paramount.

The core of these drugs is thapsigargin, a non-specific highly cytotoxic agent. Thapsigargin acts on the SERCA-pump of the cell, initiating a cellular influx of Ca$^2+$ and subsequently apoptosis. Considering the lack of cancer specificity, considerable toxicity could be noted if used as a cytotoxic agent. However, Thapsigargin can be inactivated by the binding of an amino acid sequence thus making an inactivated pro-drug. The amino acid sequence can be modeled so that it can be recognized and subsequently clipped of by proteases like PSA or PSMA. Although normal prostate tissue has adequate amounts of both PSA and PSMA, the concentration is considerable higher in malignancy, high grade malignancy and even metastasis. Therefore PSA and PSMA are favorable to use as targets for treatment and diagnosis.

To facilitate imaging, a phenol ring is added in the free-drug molecule and it can be used to link radio tracers, in this study, e.g., $^{125}$I. When the amino acid sequence is clipped by PSA or PSMA, the now activated free-drug is taken up by the prostate cancer cells, making it possible to perform targeted imaging of the cancer cells. Although the dosage for imaging is much lower than a therapeutically dose, the imaging drugs still hold some cell kill properties, resulting in targeted therapy.

With the presently disclosed unique combination of a targeted imaging agent combined with a targeted therapy, a "smart bomb" for prostate cancer is disclosed. The pro-drugs could be used for diagnosis, prediction of treatment outcome, treatment monitoring and follow-up.

Example 2

Methods

Imaging pro-drugs: JHD-9783 (PSMA) and JHD-9784 (PSA) were designed on the basis of 2 therapeutic pro-drugs: G202 (PSMA) and G114 (PSA). The difference between the 2 groups is the addition of a phenol ring for imaging probe linking ($^{125}$I). See FIG. 7.

MTT analysis: performed for both drugs to establish cell-kill potential, using LNCaP cells. Standard MTT setup was used, drugs were tested for several different dosage.

Cleavage assays: establish if the addition of the phenol ring altered the cleavage of the pro-drugs by PSA or PSMA.

LNCaP cells were cultured either without or with the addition of drugs in the media. After 3 days the cells and media were collected, and prepared for LC/MS analysis.

Iodination: standard electrophilic iodination chemistry was performed for iodination. First cold NaI was used for method development. HPLC was used for separation of the non-iodinated and iodinated compound. After method development hot Na$^{125}$I was used to create the imaging drugs HPLC was used again for separation.

Imaging: in the small animal imaging core of the JHMI SPECT-CT imaging experiments were performed on nude mice bearing LNCaP, LAPC4, PC3-PIP and PC3-flu subcutaneous tumors.

Example 2

Results

Figure 8A:
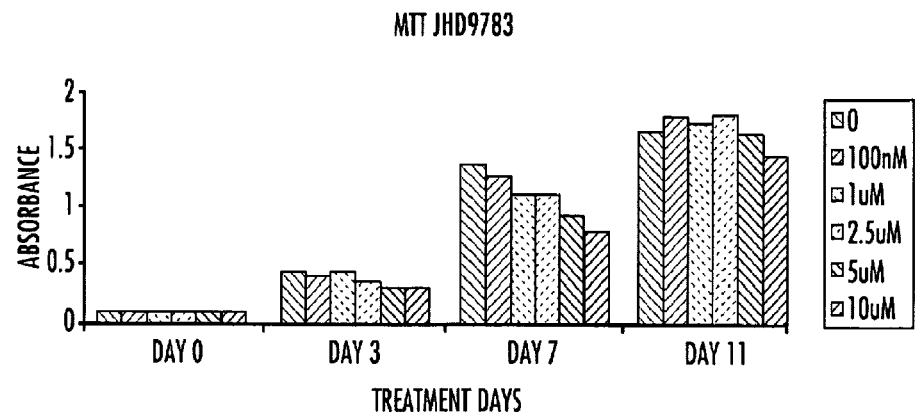
FIG. 8. MTT analysis is performed for both drugs to establish cell-kill potential using LNCaP cells. Standard MTT setup was used, drugs were tested for several different dosages (A) JHD 9783 [(PhADT)-Glu-yGlu-yGlu-yGlu] (SEQ ID NO. 63) (FIG. 8A) or (B) JHD 9784 [His-Ser-Ser-Lys-Leu-Gln-Leu-(PhADT)] (SEQ ID NO. 64) (FIG. 8B).
Figure 8B:
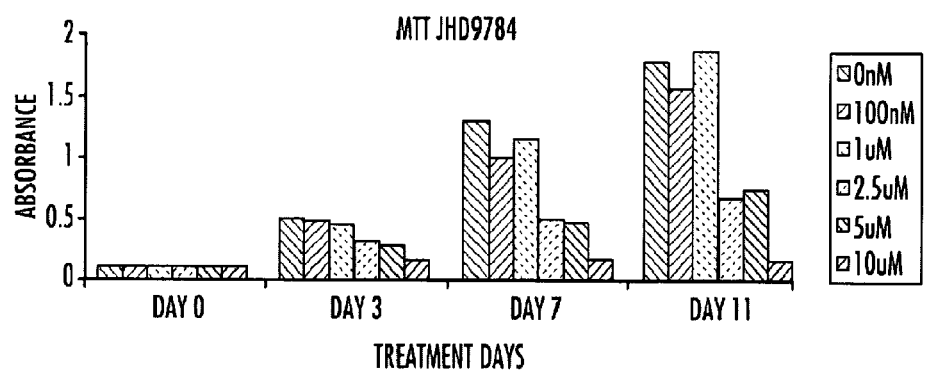

MTT analysis indicates that PMSA prodrug JHD9753 showed a IC$_{50}$ between 1 and 10 nM. MTT analysis of the PSA prodrug JHD9784 demonstrated an IC$_{50}$ at 2.5 nM concentration. (Cell kill measured on LNCaP-cells). FIG. 8.

A Cleavage assay for 2 PSMA pro-drugs G202 (C) and JHD9783 (D) and 2 PSA pro-drugs G114 (E) and JHD9784 (F) as shown in FIG. 9. Metabolites were detected with LC/MS. Results show that LNCaP cells can cleave all compounds. Highest amount of free-drug was found in the cell extract sample, indicating clear uptake of the activated free-drug.

Figure 10:
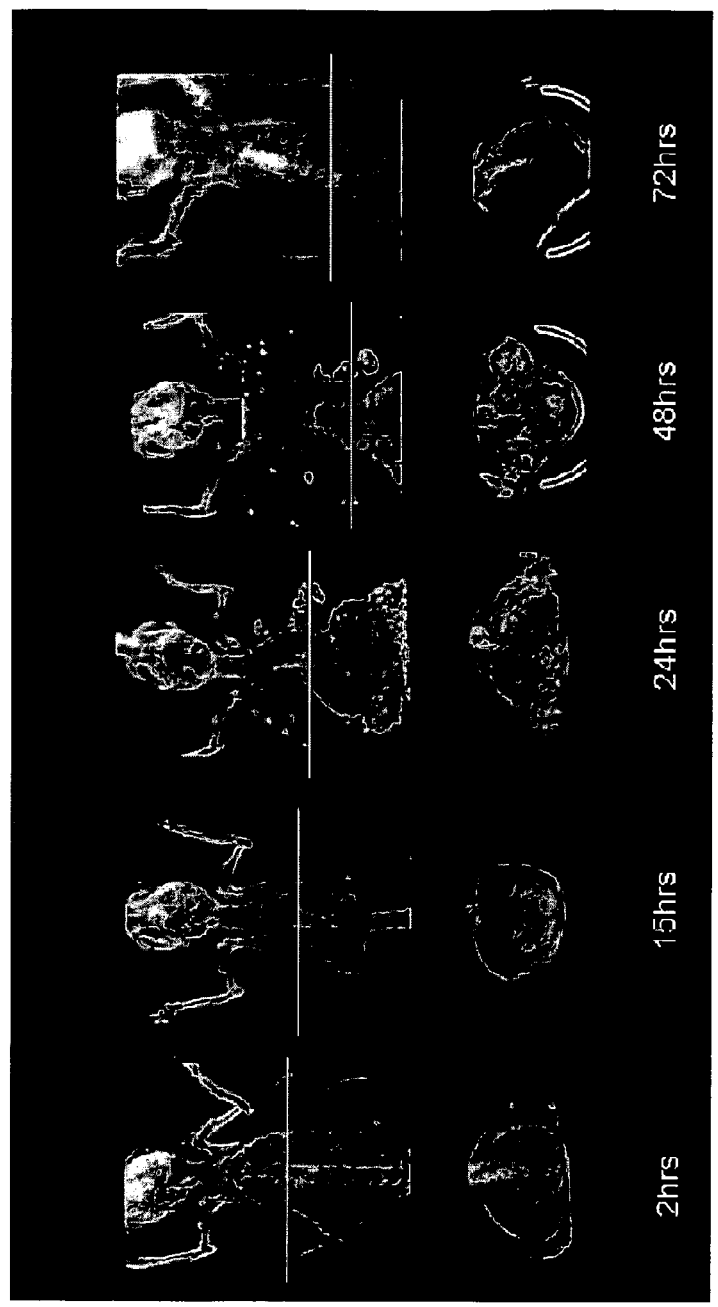
FIG. 10. SPECT/CT Imaging of PSMA thapsigargin prodrug with 125-I as a radio tracer. Top image is a 3D-reconstruction image, the bottom image is the corresponding (white line) transverse section. On the left flank of animals is a PC3-PSMA tumor (PSMS producing), on the right side a PC3-vector control (PSMA negative) tumor as a negative control. Specific tumor uptake in the PSMA positive tumor is noted >24 hrs.

Additionally, SPECT/CT images of a nude mouse with 2 tumors was performed as shown in FIG. 10. Briefly, a mouse with a PC3-PIP xenograph on the left thorax a (a PC3 cell line transfected with PSMA receptor, PSMA+) and a PC3-flu on the right thorax (a PC3 cell line transfected with a empty flu vector, PSMA−) were treated with an initial dose was 550 µCi of I$^{125}$ labeled JHD9783. The dose was administered by a tail vein injection. The animal was anaesthetized and images were mad at 2 hrs, 15 hrs, 24 hrs, 48 hrs and 72 hrs. Within the first 24 hours, no specific tumor uptake was observed. Cardiac uptake and liver uptake was observed. Cardiac uptake could be explained due to blood pooling. No notable kidney uptake was observed. At 24 hours, uptake was noted in the PSMA+ tumor, and somewhat in the rim of the PSMA− tumor. Next to liver uptake, it seemed that also intestinal uptake was noted. The intestinal uptake could be the result of excretion of the labeled agent via the bile. Kidney uptake could not be excluded. Only a remnant of cardiac uptake was noted. At 48 hours, increased uptake was noted in the PSMA+ tumor, while the PSMA− tumor remained negative. No cardiac uptake was noted, a decreased liver uptake was noted, and intestinal excretion was noted. Still no kidney uptake was noted. At 72 hrs the overall signal was very weak, but still PSMA+ tumor uptake was noted, especially compared with the PSMA− side. Some intestinal excretion was still notes, with decreasing liver uptake. At 96 hrs (not shown) the signal was too weak to detect for a proper SPECT/CT. The animal was sacrificed and the different organs and both tumors were collected and analyzed on a I$^{125}$ counter.

Figure 11:
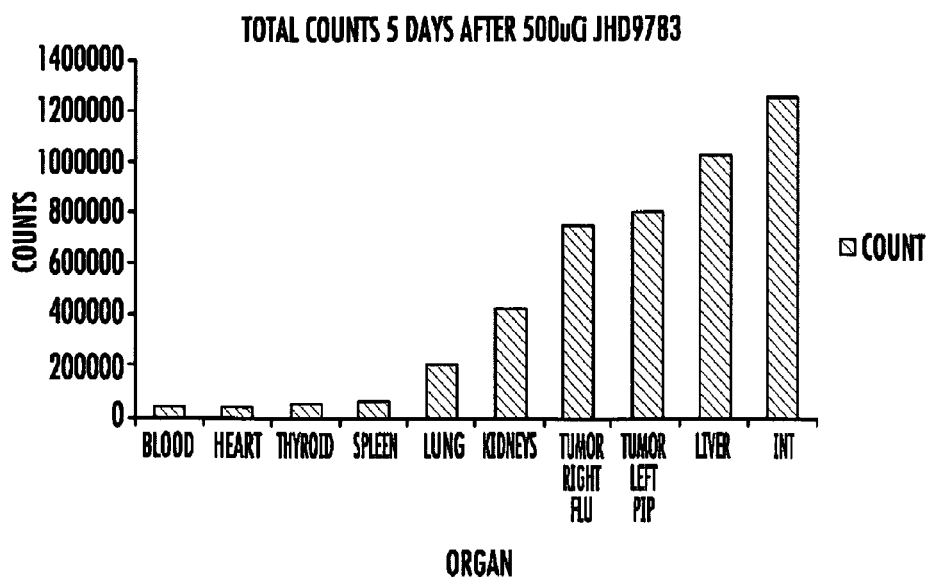
FIG. 11. $I^{125}$ count. 5 Days after the initial tail vein injection, the mouse was sacrificed and the organs were collected, together with the 2 tumors. Specimens were weighed, and counts were collected.
Figure 11:
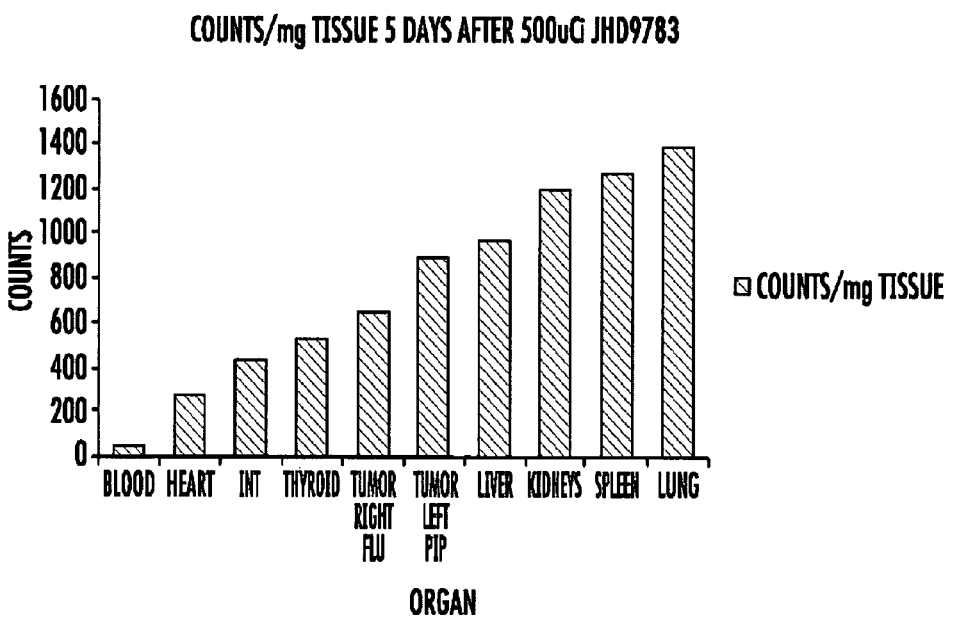

Five days after the initial tail vein injection, the mouse was sacrificed and the organs were col (SEQ ID NO:56)lected, together with the 2 tumors. Specimens were weighed, and counts were collected. Considering the total counts, the liver and both tumors were hot (PIP>flu), together with the lung. The high lung counts cannot be explained other than $^{125}$I contamination during the dissection, possible due to the proximity of the liver. When corrected for weight, the spleen, kidneys and liver are hot, together with the tumors (PIP>flu). No apparent toxicity was noted. FIG. 11.

In conclusion, the pro-drug delivery mechanism, using an inactivated pro-drug and activating to a free drug it by prostate cancer specific protease activity (PSA or PSMA) is feasible. It was noted that the cell kill properties of both imaging pro-drugs is about 10× less that the previous reported therapeutic pro drugs (G114 and G202). The inventors also noted that after 3 days of incubation with LNCaP cells, MassSpec analysis of the cell-extract and the cell media showed an almost 100% cleavage for both pro-drugs into the free-drug. It was further noted that imaging analysis, using SPECT/CT at the JHMI animal imaging core, showed selected uptake by either PSA or PSMA rich tumors. Uptake increased within the first 24 hours and decreased significant after 72 hours. Non-specific uptake was seen on the liver, thyroid, spleen and kidney.

Example 3

Determination of hK2 Cleavage Sites in Semenogelin I and II

Purified semenogelin 1 and 11 (40 µg), was incubated with hK2 (8 µg) in 50 mM Tris pH 7.5, 0.1 M NaCl, 0.15 M urea at 37° C. for 4 hours. The fragments generated were purified by reverse phase HPLC using a C-8 column. Elution was achieved with a 0-30% (0.25%/min.) linear acetonitrile gradient and fractions corresponding to individual peaks were collected. The amino terminal sequences of the individual peaks were determined by automated amino terminal sequencing with an Applied Biosystems 470 A gas-phase sequencer. Cleavage of either SgI or SgII with hK2 results in generation of a multitude of peptides. After partial separation of the peptides by reversed phase HPLC on a C-8 column sequences of four cleavage sites in SgI and seven cleavage sites in SgII were obtained. The semenogelins contain three types of internal repeats, as described in Lilja et al., *J. Biol. Chem.*, 264, 1894 2000 (1989) and Lilja et al., *PNAS USA*, 89, 4559 63 (1992). Most of the identified hK2 cleavage sites were located in different positions in these repeats. The position and sequence of the cleavage sites in SgI and SgII are shown in FIG. 11, where the cleavage sites are aligned underneath the arrows. Three identical sites of cleavage in repeat type I, which occurs twice in SgI and four times in SgII, were identified at positions 274 and 334 in SgI and position 454 in SgII. All but one of the cleavage sites contained arginine at position P1, except for one of the cleavages in Semenogelin II, which occurred on the carboxy terminal side of a histidine. It is noteworthy that no cleavages occurred on the carboxy terminal side of a lysine. Five of the eleven cleavage sites determined were double basic, the amino acid at P2 being either arginine, lysine or histidine, indicating that hK2 may cleave substrates at both mono- and di-basic sites. In one case P2 was occupied by phenylalanine which is found in the same position in PCI. In addition glycine, valine, serine, glutamine and aspartate were found at P2. In most cleavage sites P3 was occupied by a large group; in six of the cleavages it was glutamine or glutamate and in the other serine, histidine or lysine. In one case alanine was found at P3. When looking at common motifs if can be seen that in seven cases serine was found in P6. Basic amino acids were found in addition to positions P1 and P2 once in P5, twice in P3, P4, P6 and P8, and four times in P7. On the carboxy terminal side of the cleavage site leucine was found five times in P-1 and tyrosine four times in position P-3.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps of the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

U.S. Pat. No. 6,265,540 to Isaacs et al. for "Tissue Specific Prodrug," issued Jul. 24, 2001;
U.S. Pat. No. 6,410,514 to Isaacs et al. for "Tissue Specific Prodrug," issued Jun. 25, 2002;
U.S. Pat. No. 6,504,014 to Isaacs et al. for "Tissue Specific Prodrug," issued Jan. 7, 2003;
U.S. Pat. No. 6,545,131 to Isaacs et al. for "Tissue Specific Prodrug," issued Apr. 8, 2003;
U.S. Pat. No. 7,053,042 to Denmeade et al. for "Activation of Peptide Prodrugs by Human Glandular Kallikrein 2 (hK2)," issued May 30, 2006;
U.S. Pat. No. 7,468,354 to Denmeade et al. for "Tissue Specific Prodrugs," issued Dec. 23, 2008;
U.S. Pat. No. 7,635,682 to Denmeade et al. for "Tumor Activated Prodrugs," issued Dec. 22, 2009;
U.S. Patent Application Publication No. US2007/0160536 to Denmeade et al. for "Tumor-activated prodrugs," published Jul. 12, 2007;
U.S. Patent Application Publication No. US2008/0247950 to Denmeade et al. for "Activation of peptide prodrugs by hK2," published Oct. 9, 2008;
U.S. Patent Application Publication No. US2009/0163426 to Denmeade et al. for "Tissue specific prodrugs," published Jun. 25, 2009;
Christensen, S. B., et al., "Thapsigargin Analogues for Targeting Programmed Death of Androgen-Independent Prostatic Cancer Cells, Bioorg. Med. Chem. 7:1273-80 (1999);
Denmeade, S. R., et al., "Protate-Specific Antigen (PSA) Activated Thapsigargin Prodrug as Targeted Therapy for Prostate Cancer," J. Natl. Cancer Inst. 95:990-1000 (2003);
Bowden, E., Adkins, H., "A synthesis of 3-(4-hydroxycyclohexyl)-propanol-1, a product of the hydrogenation of lignin," JACS 62:2422-2423 (1940);
Cook, E. S, et al., Antistaphylococcal and Antifibinolytic Activities of Omega-Amino Acids and Their L-Histidine Dipeptides," J. Med. Chem. 14:354-357 (1971).
Puech, P., et al., "Imaging of Organ-Confined Prostate Cancer: Functional Ultrasound, MRI and PET/computed tomography," Curr. Opin. Urol. 19(2):168-176 (2009);
Marbeger, M., et al., "New Treatments for Localized Prostate Cancer," Urology 72(6 suppl):S36-43 (2008);
Bolenz, C., et al., "Clinical Staging Error in Prostate Cancer: Localization and Relevance of Undetected Tumour Areas," BJU Int. Dec. 22, 2008 [Epub ahead of print];
Chandran, S. S., et al., "A Prostate-Specific Antigen Activated N-(2-Hydroxypropyl)Methacrylamide Copolymer Prodrug as Dual-Targeted Therapy for Prostate Cancer," Mol. Cancer Ther. 6(11):2928-2937 (2007);
Søhoel, H., et al., "Natural Products as Starting Materials for Development of Second Generation SERCA Inhibitors Targeted Towards Prostate Cancer Cells," Bioorg. Med. Chem. 14(8):2810-2815 (2006).

Although the foregoing subject matter has been described in some detail by way of illustration and example for purposes of clarity of understanding, it will be understood by those skilled in the art that certain changes and modifications can be practiced within the scope of the appended claims.

What is claimed is:

1. A composition comprising:
   a) thapsigargin (TG) or a thapsigargin analog;
   b) a phenolic linker; and
   c) a peptide cleavable by a protein selected from:
      i) prostate specific membrane antigen (PSMA);
      ii) prostate specific antigen (PSA); and
      iii) human glandular kallikrein 2 (hK2)

wherein said phenolic linker is conjugated to said thapsigargin or thapsigargin analogue.

2. The composition of claim 1, wherein the phenolic linker further comprises a radiolabel.

3. The composition of claim 2, wherein the radiolabel is at least one of $^{125}$I, $^{124}$I, $^{131}$I, or $^{3}$H.

4. The composition of claim 1, wherein the peptide is cleavable by PSMA.

5. The composition of claim 4, wherein the composition has the following chemical structure:

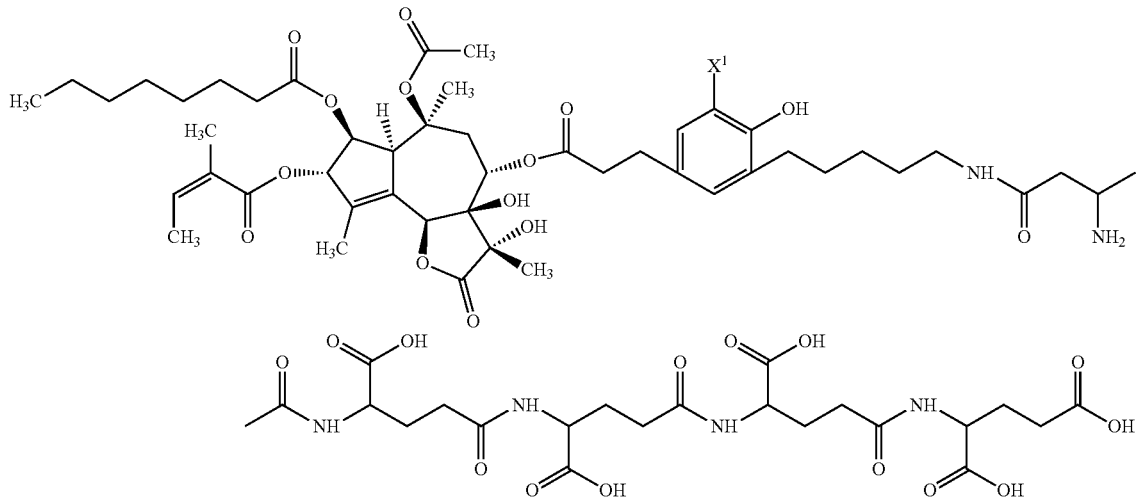

wherein $X_1$ can be present or absent and when present is selected from the group consisting of $^{124}I$, $^{125}I$, $^{131}I$, and $^3H$.

6. The composition of claim 4, wherein the peptide comprises the sequence Asp-Glu*Glu*Glu*Glu (SEQ ID NO:57).

7. The composition of claim 4, wherein the peptide consists of Asp-Glu*Glu*Glu*Glu (SEQ ID NO:57).

8. The composition of claim 4, wherein the peptide comprises Asp-Glu.

9. The composition of claim 4, wherein the peptide consists of Asp-Glu.

10. The composition of claim 1, wherein the peptide is cleavable by PSA.

11. The composition of claim 10, wherein the composition has the following chemical structure:

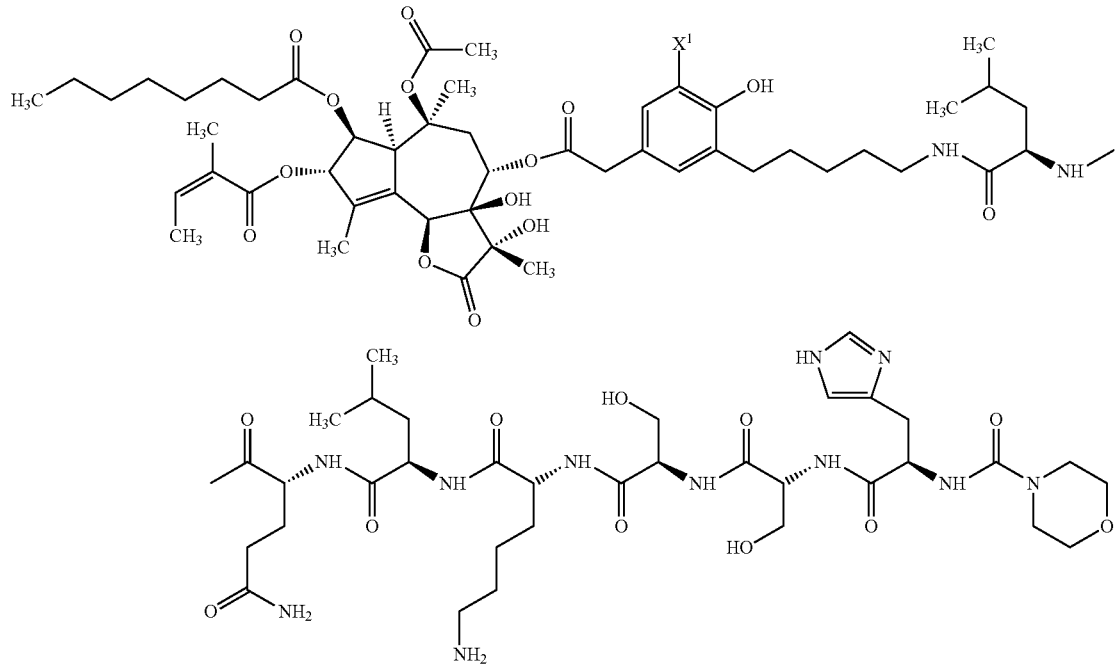

wherein $X_1$ can be present or absent and when present is selected from the group consisting of $^{124}I$, $^{125}I$, $^{131}I$, and $^3H$.

12. The composition of claim 10, wherein the peptide is selected from the group consisting of Ser-Lys-Leu-Gln-Leu (SEQ ID NO:42), Ile-Ser-Tyr-Gln-Leu (SEQ ID NO:43), Lys-Ser-Lys-Gln-Leu (SEQ ID NO:44), Ser-Ser-Lys-Leu-Gln-Leu (SEQ ID NO:45), Lys-Ile-Ser-Tyr-Gln-Leu (SEQ ID NO:46), Thr-Lys-Ser-Lys-Gln-Leu (SEQ ID NO:47), His-Ser-Ser-Lys-Leu-Gln-Leu (SEQ ID NO:48), Asn-Lys-Ile- Ser-Tyr-Gln-Leu (SEQ ID NO:49), Ala-Thr-Lys-Ser-Lys-Gln-Leu (SEQ ID NO:50), Glu-His-Ser-Ser-Lys-Leu-Gln-Leu (SEQ ID NO:51), Gln-Asn-Lys-Ile-Ser-Tyr-Gln-Leu (SEQ ID NO:52), Glu-Asn-Lys-Ile-Ser-Tyr-Gln-Leu (SEQ ID NO:53), Ala-Thr-Lys-Ser-Lys-Gln-His-Leu (SEQ ID NO:55), and His-Ser-Ser-Lys-Leu-Gln-Leu (SEQ ID NO:56).

13. The composition of claim 12, wherein the peptide consists of His-Ser-Ser-Lys-Leu-Gln-Leu (SEQ ID NO:56).

14. The composition of claim 12, wherein the peptide further comprises a capping group attached to the N-terminus of the peptide, the group inhibiting endopeptidase activity.

15. The composition of claim 14, wherein the capping group is selected from the group consisting of acetyl, morpholinocarbonyl, benzyloxycarbonyl, glutaryl, and succinyl substituents.

16. The composition of claim 1, wherein the peptide is cleavable by hK2.

17. The composition of claim 16, wherein the peptide is selected from the group consisting of Lys-Arg-Arg (SEQ ID NO:1), Ser-Arg-Arg (SEQ ID NO:2), Ala-Arg-Arg (SEQ ID NO:3), His-Arg-Arg (SEQ ID NO:4), Gln-Arg-Arg (SEQ ID NO:5), Ala-Phe-Arg (SEQ ID NO:6), Ala-Gln-Arg (SEQ ID NO:7), Ala-Lys-Arg (SEQ ID NO:8), Ala-Arg-Lys (SEQ ID NO:9), Ala-His-Arg (SEQ ID NO:10), Gln-Lys-Arg-Arg (SEQ ID NO:11), Lys-Ser-Arg-Arg (SEQ ID NO:12), Ala-Lys-Arg-Arg (SEQ ID NO:13), Lys-Lys-Arg-Arg (SEQ ID NO:14), His-Lys-Arg-Arg (SEQ ID NO:15), Lys-Ala-Phe-Arg (SEQ ID NO:16), Lys-Ala-Gln-Arg (SEQ ID NO:17), Lys-Ala-Lys-Arg (SEQ ID NO:18), Lys-Ala-Arg-Lys (SEQ ID NO:19), Lys-Ala-His-Arg (SEQ ID NO:20), Lys-Arg-Arg-Leu (SEQ ID NO:21), Ser-Arg-Arg-Leu (SEQ ID NO:22), Ala-Arg-Arg-Leu (SEQ ID NO:23), Ala-Arg-Arg-Ser (SEQ ID NO:24), His-Arg-Arg-Ala (SEQ ID NO:25), Gln-Arg-Arg-Leu (SEQ ID NO:26), Ala-Phe-Arg-Leu (SEQ ID NO:27), Ala-Gln-Arg-Leu (SEQ ID NO:28), Ala-Lys-Arg-Leu (SEQ ID NO:29), Ala-Arg-Lys-Leu (SEQ ID NO:30), Ala-His-Arg-Leu (SEQ ID NO:31), His-Ala-Gln-Lys-Arg-Arg-Leu (SEQ ID NO:32), Gly-Gly-Lys-Ser-Arg-Arg-Leu (SEQ ID NO:33), His-Glu-Gln-Lys-Arg-Arg-Leu (SEQ ID NO:34), His-Glu-Ala-Lys-Arg-Arg-Leu (SEQ ID NO:35), Gly-Gly-Gln-Lys-Arg-Arg-Leu (SEQ ID NO:36), His-Glu-Gln-Lys-Arg-Arg-Ala (SEQ ID NO:37), Gly-Gly-Ala-Lys-Arg-Arg-Leu (SEQ ID NO:38), His-Glu-Gln-Lys-Arg-Arg-Ser (SEQ ID NO:39), Gly-Gly-Lys-Lys-Arg-Arg-Leu (SEQ ID NO:40), Gly-Gly-His-Lys-Arg-Arg-Leu (SEQ ID NO:41) and Gly-Gly-Lys-Ala-Arg-Arg-Leu (SEQ ID NO:54).

18. The composition of claim 17, wherein the peptide consists of Gly-Gly-Lys-Ala-Arg-Arg-Leu (SEQ ID NO:54).

19. The composition of claim 17, wherein the peptide further comprises a capping group attached to the N-terminus of the peptide, the group inhibiting endopeptidase activity.

20. The composition of claim 19, wherein the capping group is selected from the group consisting of acetyl, morpholinocarbonyl, benzyloxycarbonyl, glutaryl, and succinyl substituents.

21. The composition of claim 13, wherein the peptide further comprises a capping group attached to the N-terminus of the peptide, the group inhibiting endopeptidase activity.

22. The composition of claim 18, wherein the peptide further comprises a capping group attached to the N-terminus of the peptide, the group inhibiting endopeptidase activity.

23. A composition for detecting a prostate cancer comprising:

a) thapsigargin (TG) or a thapsigargin analog;

b) a phenolic linker comprising a radiolabel; and c) a peptide cleavable by a protein selected from:

i) prostate specific membrane antigen (PSMA);

ii) prostate specific antigen (PSA); and iii) human glandular kallikrein 2 (hK2)

wherein said phenolic linker is conjugated to said thapsigargin or thapsigargin analogue.

24. The composition of claim 23, wherein said radiolabel is at least one of $^{125}$I, $^{124}$I, $^{131}$I, or $^{3}$H.

25. A composition for detecting a cancer comprising:

a) thapsigargin (TG) or a thapsigargin analog;

b) a phenolic linker comprising a radiolabel; and c) a peptide cleavable by prostate specific membrane antigen (PSMA), wherein said phenolic linker is conjugated to said thapsigargin or thapsigargin analogue.

26. The composition of claim 25, wherein said radiolabel is at least one of $^{125}$I, $^{124}$I, $^{131}$I, or $^{3}$H.

27. A method of imaging or treating a subject having cancer or suspected of having cancer comprising administering to the subject a composition comprising:

a) thapsigargin (TG) or a thapsigargin analog;

b) a phenolic linker comprising a radiolabel; and c) a peptide cleavable by prostate specific membrane antigen (PSMA);

wherein said phenolic linker is conjugated to said thapsigargin or thapsigargin analogue.

28. The method of claim 27, wherein the imaging the subject further comprises single photon emission computed tomography (SPECT).

29. The method of claim 28, wherein the radiolabel is $^{125}$I.

30. The method of claim 27, wherein the imaging the subject further comprises positron emission tomography (PET).

31. The method of claim 30, wherein the radiolabel is $^{124}$I.

32. The method of claim 27, wherein the treating the subject further comprises combination drug and radiation therapy.

33. The method of claim 32, wherein the radiolabel is $^{131}$I.

34. The method of claim 27, wherein the cancer is at least one of prostate cancer, breast cancer, renal cancer, colon cancer or transitional cell carcinomas.

35. The method of claim 27, wherein the radiolabel is $^{3}$H.

36. The method of claim 27, wherein the composition has a chemical structure selected from the group consisting of:

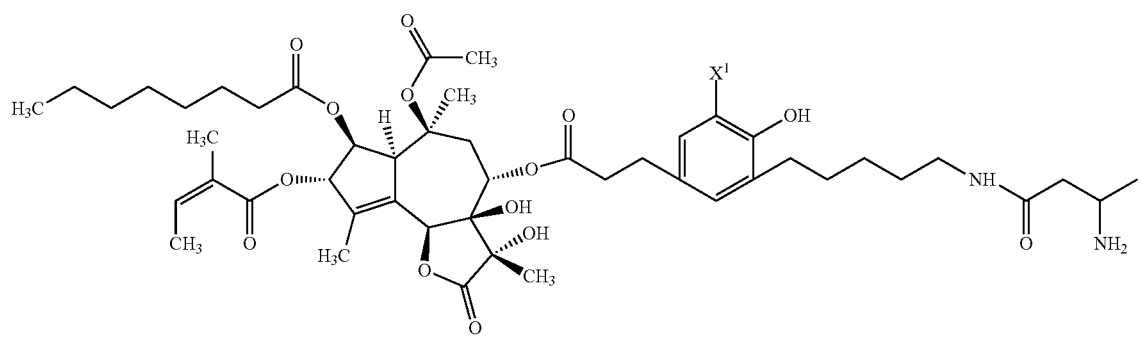

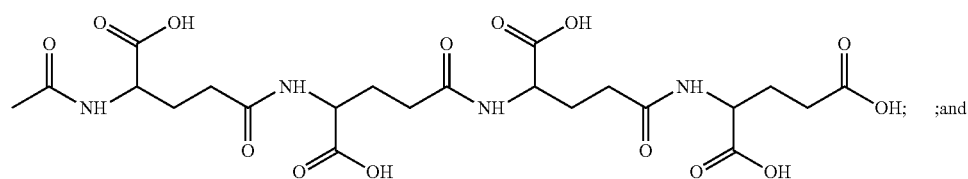

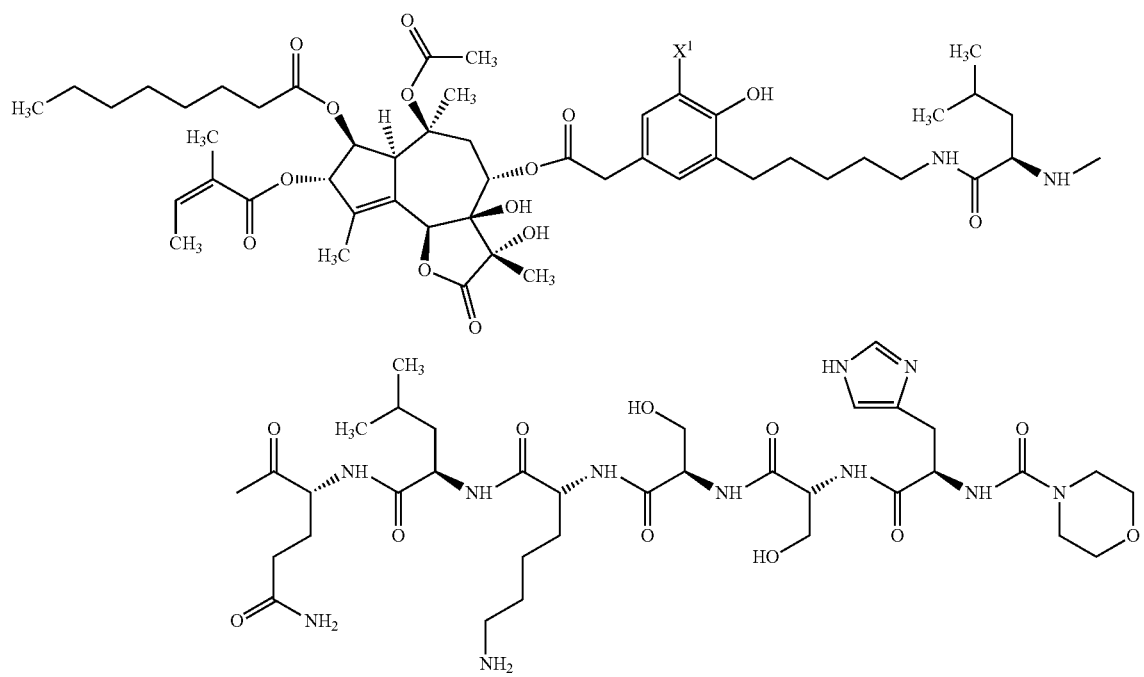

wherein $X_1$ is selected from the group consisting of $^{124}I$, $^{125}I$, $^{131}I$, and $^3H$.

37. A method of imaging or treating a subject having prostate cancer or suspected of having prostate cancer comprising administering to the subject a composition comprising:
 a) thapsigargin (TG) or a thapsigargin analog;
 b) a phenolic linker comprising a radiolabel; and
 c) a peptide cleavable by a protein selected from:
  i) prostate specific membrane antigen (PSMA);
  ii) prostate specific antigen (PSA); and
  iii) human glandular kallikrein 2 (hK2)
wherein said phenolic linker is conjugated to said thapsigargin or thapsigargin analogue.

38. The method of claim 37, wherein the imaging the subject further comprises single photon emission computed tomography (SPECT).

39. The method of claim 38, wherein the radiolabel is $^{125}I$.

40. The method of claim 37, wherein the imaging the subject further comprises positron emission tomography (PET).

41. The method of claim 40, wherein the radiolabel is $^{124}I$.

42. The method of claim 37, wherein the treating the subject further comprises combination drug and radiation therapy.

43. The method of claim 40, wherein the radiolabel is $^{131}I$.

44. The method of claim 37, wherein the radiolabel is $^3H$.

45. The method of claim 37, wherein the composition has a chemical structure selected from the group consisting of:

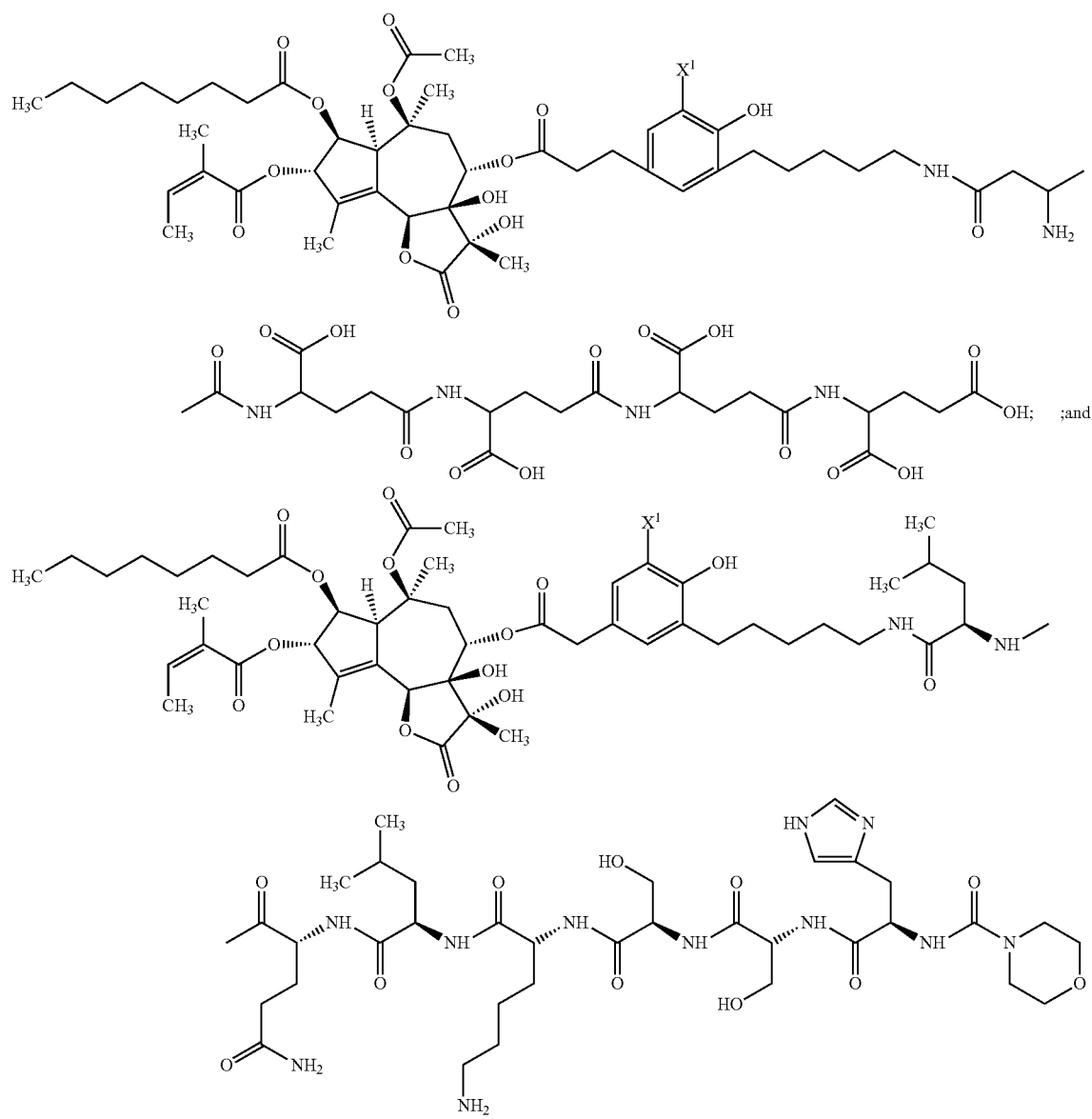
wherein $X_1$ is selected from the group consisting of $^{124}I$, $^{125}I$, $^{131}I$, and 3H.
* * * * *

SEQUENCE LISTING

```
<160> NUMBER OF SEQ ID NOS: 73

<210> SEQ ID NO 1
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Arg Arg
1

<210> SEQ ID NO 2
<211> LENGTH: 3
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 2

Ser Arg Arg
1

<210> SEQ ID NO 3
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Arg Arg
1

<210> SEQ ID NO 4
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

His Arg Arg
1

<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Arg Arg
1

<210> SEQ ID NO 6
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Phe Arg
1

<210> SEQ ID NO 7
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Gln Arg
1
```

```
<210> SEQ ID NO 8
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Lys Arg
1

<210> SEQ ID NO 9
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Arg Lys
1

<210> SEQ ID NO 10
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala His Arg
1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gln Lys Arg Arg
1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Ser Arg Arg
1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13
```

```
Ala Lys Arg Arg
1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Lys Arg Arg
1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

His Lys Arg Arg
1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Lys Ala Phe Arg
1

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Lys Ala Gln Arg
1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Ala Lys Arg
1

<210> SEQ ID NO 19
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 19

Lys Ala Arg Lys
1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys Ala His Arg
1

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Lys Arg Arg Leu
1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Arg Arg Leu
1

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Arg Arg Leu
1

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Arg Arg Ser
1
```

```
<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

His Arg Arg Ala
1

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Arg Arg Leu
1

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Phe Arg Leu
1

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Gln Arg Leu
1

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Lys Arg Leu
1

<210> SEQ ID NO 30
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 30

Ala Arg Lys Leu
1

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala His Arg Leu
1

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

His Ala Gln Lys Arg Arg Leu
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Gly Lys Ser Arg Arg Leu
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

His Glu Gln Lys Arg Arg Leu
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 35

His Glu Ala Lys Arg Arg Leu
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Gly Gln Lys Arg Arg Leu
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

His Glu Gln Lys Arg Arg Ala
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Gly Ala Lys Arg Arg Leu
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

His Glu Gln Lys Arg Arg Ser
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Gly Lys Lys Arg Arg Leu
1               5
```

```
<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Gly His Lys Arg Arg Leu
1               5

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ser Lys Leu Gln Leu
1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ile Ser Tyr Gln Leu
1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Lys Ser Lys Gln Leu
1               5

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ser Ser Lys Leu Gln Leu
1               5

<210> SEQ ID NO 46
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 46

Lys Ile Ser Tyr Gln Leu
1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Thr Lys Ser Lys Gln Leu
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

His Ser Ser Lys Leu Gln Leu
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Asn Lys Ile Ser Tyr Gln Leu
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ala Thr Lys Ser Lys Gln Leu
1               5

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Glu His Ser Ser Lys Leu Gln Leu
1               5
```

```
<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gln Asn Lys Ile Ser Tyr Gln Leu
1               5

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Glu Asn Lys Ile Ser Tyr Gln Leu
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Gly Lys Ala Arg Arg Leu
1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ala Thr Lys Ser Lys Gln His Leu
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

His Ser Ser Lys Leu Gln Leu
1               5

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: misc_feature
<222> LOCATION: (2)..(3)
<223> OTHER INFORMATION: Gamma peptide linkage
<220> FEATURE:
<221> NAME/KEY: misc_feature
<222> LOCATION: (3)..(4)
<223> OTHER INFORMATION: Gamma peptide linkage
<220> FEATURE:
<221> NAME/KEY: misc_feature
<222> LOCATION: (4)..(5)
<223> OTHER INFORMATION: Gamma peptide linkage

<400> SEQUENCE: 57

Asp Glu Glu Glu Glu
1               5

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(2)
<223> OTHER INFORMATION: Gamma peptide linkage
<220> FEATURE:
<221> NAME/KEY: misc_feature
<222> LOCATION: (2)..(3)
<223> OTHER INFORMATION: Gamma peptide linkage
<220> FEATURE:
<221> NAME/KEY: misc_feature
<222> LOCATION: (3)..(4)
<223> OTHER INFORMATION: Gamma peptide linkage

<400> SEQUENCE: 58

Glu Glu Glu Asp Glu
1               5

<210> SEQ ID NO 59
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(2)
<223> OTHER INFORMATION: Gamma peptide linkage
<220> FEATURE:
<221> NAME/KEY: misc_feature
<222> LOCATION: (2)..(3)
<223> OTHER INFORMATION: Gamma peptide linkage
<220> FEATURE:
<221> NAME/KEY: misc_feature
<222> LOCATION: (3)..(4)
<223> OTHER INFORMATION: Gamma peptide linkage

<400> SEQUENCE: 59

Glu Glu Glu Asp Gln
1               5

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
```

```
<222> LOCATION: (2)..(3)
<223> OTHER INFORMATION: Gamma peptide linkage
<220> FEATURE:
<221> NAME/KEY: misc_feature
<222> LOCATION: (3)..(4)
<223> OTHER INFORMATION: Gamma peptide linkage

<400> SEQUENCE: 60

Asp Glu Glu Asp Glu
1               5

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(3)
<223> OTHER INFORMATION: Gamma peptide linkage
<220> FEATURE:
<221> NAME/KEY: misc_feature
<222> LOCATION: (3)..(4)
<223> OTHER INFORMATION: Gamma peptide linkage

<400> SEQUENCE: 61

Glu Glu Glu Asp Glu
1               5

<210> SEQ ID NO 62
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(2)
<223> OTHER INFORMATION: Gamma peptide linkage
<220> FEATURE:
<221> NAME/KEY: misc_feature
<222> LOCATION: (2)..(3)
<223> OTHER INFORMATION: Gamma peptide linkage
<220> FEATURE:
<221> NAME/KEY: misc_feature
<222> LOCATION: (3)..(4)
<223> OTHER INFORMATION: Gamma peptide linkage
<220> FEATURE:
<221> NAME/KEY: misc_feature
<222> LOCATION: (4)..(5)
<223> OTHER INFORMATION: Gamma peptide linkage

<400> SEQUENCE: 62

Glu Glu Glu Glu Glu
1               5

<210> SEQ ID NO 63
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(2)
<223> OTHER INFORMATION: Gamma peptide linkage
<220> FEATURE:
<221> NAME/KEY: misc_feature
<222> LOCATION: (2)..(3)
```

<223> OTHER INFORMATION: Gamma peptide linkage

<400> SEQUENCE: 63

Glu Glu Glu Glu
1

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Leu Gln Leu Lys Ser Ser His
1               5

<210> SEQ ID NO 65
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

His Lys Gly Gly Lys Ala His Arg Gly Thr Gln
1               5                   10

<210> SEQ ID NO 66
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ser Ser Ser Tyr Glu Glu Arg Arg Leu His Tyr
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Val Gln Lys Asp Val Ser Gln Arg Ser Ile Tyr
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asp Lys Ser Lys Gly His Phe His Met Ile Val
1               5                   10

<210> SEQ ID NO 69

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gln Cys Ser Asn Thr Glu Lys Arg Leu Trp Val
1               5                   10

<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Leu His Pro Ala His Gln Asp Arg Leu Gln His
1               5                   10

<210> SEQ ID NO 71
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Lys Ile Ser Tyr Pro Ser Ser Arg Thr Glu Glu
1               5                   10

<210> SEQ ID NO 72
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Lys Ser Gln Asn Gln Val Arg Ile Pro Ser
1               5                   10

<210> SEQ ID NO 73
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Leu Ser His Glu Gln Lys Gly Arg Tyr Lys Gln
1               5                   10
```